US011963711B2

(12) United States Patent
Pope et al.

(10) Patent No.: US 11,963,711 B2
(45) Date of Patent: Apr. 23, 2024

(54) ELECTROSURGICAL SYSTEM WITH TISSUE AND MAXIMUM CURRENT IDENTIFICATION

(71) Applicant: Applied Medical Resources Corporation, Rancho Santa Margarita, CA (US)

(72) Inventors: Ryan Pope, Rancho Santa Margarita, CA (US); Melissa Brodsky, Rancho Santa Margarita, CA (US); Vincent Rodriguez, Rancho Santa Margarita, CA (US); Molly Marbut, Schertz, TX (US); Kevin Siazon, Rancho Santa Margarita, CA (US); Emily Koehler, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 430 days.

(21) Appl. No.: 17/138,418

(22) Filed: Dec. 30, 2020

(65) Prior Publication Data
US 2021/0196368 A1    Jul. 1, 2021

Related U.S. Application Data

(60) Provisional application No. 62/955,758, filed on Dec. 31, 2019.

(51) Int. Cl.
| | | |
|---|---|---|
| A61B 18/12 | (2006.01) | |
| A61B 18/14 | (2006.01) | |
| A61B 18/00 | (2006.01) | |

(52) U.S. Cl.
CPC ...... *A61B 18/1445* (2013.01); *A61B 18/1206* (2013.01); *A61B 2018/00297* (2013.01); *A61B 2018/0063* (2013.01)

(58) Field of Classification Search
CPC ............ A61B 18/1445; A61B 18/1206; A61B 2018/1455; A61B 2018/0072; A61B 2018/00827; A61B 2018/00666
See application file for complete search history.

(56) References Cited

U.S. PATENT DOCUMENTS

| | | | |
|---|---|---|---|
| 2,073,960 | A | 3/1937 | Crosby |
| 2,140,593 | A | 12/1938 | Pankonin |
| (Continued) | | | |

FOREIGN PATENT DOCUMENTS

| | | |
|---|---|---|
| EP | 0 251 444 A1 | 1/1988 |
| EP | 0 492 283 A1 | 7/1992 |
| (Continued) | | |

OTHER PUBLICATIONS

International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.

(Continued)

*Primary Examiner* — Daniel W Fowler
(74) *Attorney, Agent, or Firm* — Thomas Nguyen; Patrick Ikehara

(57) ABSTRACT

An electrosurgical system is provided and includes an electrosurgical instrument and an electrosurgical generator. The electrosurgical system obtains information about the tissue undergoing a sealing process in order to calculate information about the tissue undergoing the sealing process and, in real-time, modify the RF energy being provided to the electrosurgical instrument from the electrosurgical generator. In this way, the electrosurgical system manages the supply of RF energy to optimally seal different types of tissue. The electrosurgical instrument is configured to seal the tissue using the RF energy.

22 Claims, 30 Drawing Sheets

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,115 A | 11/1996 | Nicholas |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |

(56) References Cited

U.S. PATENT DOCUMENTS

| | | |
|---|---|---|
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |

(56) References Cited

U.S. PATENT DOCUMENTS

| | | |
|---|---|---|
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |

(56) References Cited

U.S. PATENT DOCUMENTS

| | | |
|---|---|---|
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0203504 A1* | 9/2005 | Wham ............... A61B 18/1442 606/34 |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0173803 A1* | 7/2007 | Wham ................ A61B 5/053 606/34 |
| 2007/0173811 A1* | 7/2007 | Couture ............ A61B 18/1445 606/45 |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |

(56) References Cited

U.S. PATENT DOCUMENTS

| | | |
|---|---|---|
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0182321 A1* | 7/2009 | McGreevy ......... A61B 18/1442 606/33 |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0168624 A1* | 7/2010 | Sliwa ................ A61N 7/02 601/3 |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Laurent et al. |
| 2011/0208183 A1* | 8/2011 | Stockert ................ A61B 18/16 606/35 |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0296238 A1* | 11/2012 | Chernov ................ A61N 7/02 601/2 |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0025061 A1* | 1/2014 | Benamou ............... A61B 18/18 606/33 |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0058382 A1* | 2/2014 | Yang .................... A61B 18/18 606/33 |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |

(56) References Cited

U.S. PATENT DOCUMENTS

| | | |
|---|---|---|
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0196349 A1* | 7/2015 | Wham ............... A61B 18/1206 606/34 |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0272657 A1* | 10/2015 | Yates ................ A61B 18/1206 606/34 |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2015/0380187 A1 | 12/2015 | Zergieebel et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0199125 A1* | 7/2016 | Jones ................. A61B 18/1445 606/49 |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0042604 A1* | 2/2017 | McFarland ......... A61B 18/1445 |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |
| 2019/0000533 A1* | 1/2019 | Messerly ........... A61B 18/1206 |
| 2019/0261984 A1 | 8/2019 | Nelson et al. |
| 2020/0268381 A1 | 8/2020 | Roberts et al. |
| 2022/0000539 A1* | 1/2022 | Shah .................. A61B 18/1445 |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 815 705 A1 | 12/2014 |
| EP | 2 923 661 A2 | 3/2015 |
| EP | 2 853 204 A1 | 4/2015 |
| EP | 2 891 462 A1 | 7/2015 |
| EP | 2 926 742 A1 | 10/2015 |
| EP | 2 942 020 A2 | 11/2015 |
| EP | 2 959 851 A1 | 12/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |

(56) References Cited

FOREIGN PATENT DOCUMENTS

| WO | WO 2004/032762 A1 | 4/2004 |
|---|---|---|
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

European Patent Office, The International Search Report and the Written Opinion of the International Searching Authority for International Application No. PCT/US2021/057278, entitled "Actuation Shaft Retention Mechanism for Surgical Stapler" dated Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" dated Feb. 11, 2022, 15 pgs.
European Patent Office, Extended European Search Report for European Application No. EP 20197859.0, entitled "Surgical Stapler with Circumferential Firing," dated Jan. 28, 2021, 13 pgs.
European Patent Office, The International Search Report and Written Opinion for International Application No. PCT/US2020/067540, dated May 3, 2021, entitled "Electrosurgical System with Tissue and Maximum Current Identification," 12 pages.
European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.
European Patent Office, Extended European Search Report for European Application No. EP 21195788.1, entitled "Surgical Stapler with Self-Adjusting Staple Height," dated Dec. 13, 2021, 9 pgs.
European Patent Office, European Search Report for European Application No. 07784007.2, entitled "Surgical Stapler," dated Jun. 15, 2012, 6 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
European Patent Office, International Search Report and Written Opinion for International Application No. PCT/US2014/028211, entitled "Surgical Stapler with Partial Pockets," dated Sep. 8, 2014, 17 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.

(56) References Cited

OTHER PUBLICATIONS

European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
European Patent Office, Extended European Search Report for European Application No. EP 20157713.7, entitled "Surgical Stapler with Expandable Jaw," dated May 11, 2020, 6 pgs.
European Patent Office, Extended European Search Report for European Application No. EP 20161294.2, entitled "Surgical Stapler with Self-Adjusting Staple Height," dated Jun. 22, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
International Preliminary Examining Authority/US, International Preliminary Report on Patentability for International Application No. PCT/US2020/067540, titled "Electrosurgical System with Tissue and Maximum Current Identification," dated Jul. 14, 2022, 9 pgs.
European Patent Office, The International Search Report and the Written Opinion of the International Searching Authority for International Application No. PCT/US2021/057365, entitled "Surgical Stapler Having a Powered Handle" dated Apr. 13, 2022, 21 pgs.
European Patent Office, The International Search Report and the Written Opinion of the International Searching Authority for International Application No. PCT/US2022/012252, entitled "Surgical Stapler Having Shaft Recognition Mechanism" dated Apr. 13, 2022, 13 pgs.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, forInternational Application No. PCT/US2021/057231, entitled "Material Combinations and Processing Methods for a Surgical Instrument," dated May 11, 2023, 10 pgs.
The International Bureau of WIPO, International Preliminary Report on Patentability, forInternational Application No. PCT/US2021/057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.

\* cited by examiner

ELECTROSURGICAL SYSTEM WITH TISSUE AND MAXIMUM CURRENT IDENTIFICATION

CROSS-REFERENCE TO RELATED APPLICATIONS

This application claims priority to and benefit of U.S. Provisional Patent Application Ser. No. 62/955,758 entitled "Electrosurgical System with Tissue and Maximum Current Identification" filed on Dec. 31, 2019 which is incorporated herein by reference in its entirety.

FIELD OF INVENTION

The present application relates generally to electrosurgical systems and methods. In particular, the present application pertains to electrosurgical systems with tissue and maximum current identification.

BACKGROUND OF THE INVENTION

Electrosurgical devices and instruments are configured to use electrical energy to perform different surgical tasks. For example, electrosurgical instruments may include graspers, scissors, tweezers, blades, and/or needles that include one or more electrodes. These electrosurgical devices and instruments may be supplied with electrical energy from an electrosurgical generator. The electrical energy can then be used by the electrosurgical instrument to coagulate, fuse, and/or cut tissue.

Electrosurgical instruments typically fall within two classifications: monopolar and bipolar. Monopolar electrosurgical instruments supply the electrical energy to one or more electrodes on the electrosurgical instrument with high current density while a separate return electrode is electrically coupled to a patient. Monopolar electrosurgical instruments are designed to minimize current density. Monopolar electrosurgical instruments can also be useful in certain procedures but can include a risk of certain types of patient injuries such as electrical burns. The patient injuries can be at least partially attributable to functioning of the return electrode. In contrast, bipolar electrosurgical instruments use one or more electrodes that are electrically coupled to a source of electrical energy of a first polarity and one or more other electrodes that are electrically coupled to a source of electrical energy of a second polarity opposite the first polarity. In this way, bipolar electrosurgical instruments are configured to operate without separate return electrodes (as in the situation with monopolar electrosurgical instruments) and can therefore deliver electrical signals to a focused tissue area with reduced risks compared to monopolar electrosurgical instruments.

Even with the relatively focused surgical effects of using bipolar electrosurgical instruments, surgical outcomes can still be highly dependent on the skill of the user (e.g., surgeon) using the electrosurgical devices and instruments. For example, thermal tissue damage and necrosis can occur in instances where the electrical energy is delivered to an area of tissue for a relatively long duration or where a relatively high-powered electrical signal is delivered to the tissue even for a short duration. The rate at which a tissue will achieve a desired fusing, sealing, and/or cutting effect via the delivered electrical energy can vary based on a variety of different factors such as the tissue (e.g., type, volume), the pressure applied to the tissue by the electrosurgical instrument, the current state of the tissue, and/or the electrosurgical instrument being used. Thus, it can be difficult for the user (e.g., surgeon) of the electrosurgical instrument (even one who is skilled and experienced) to visually assess how quickly a mass of combined tissue types grasped via the electrosurgical instrument (e.g., monopolar or bipolar electrosurgical instrument) will become sealed. Furthermore, it can be difficult for the user (e.g., surgeon) to adjust the electrical energy being generated by the electrosurgical generator based on the same factors described above (e.g., tissue type, tissue volume, pressure, state of the tissue and/or electrosurgical instrument being used).

SUMMARY OF THE INVENTION

In accordance with various embodiments, an electrosurgical system is provided that is configured to monitor various information about tissue undergoing a sealing process in order to automatically modify the RF energy being applied to the tissue. In this way, the electrosurgical system can control how the RF energy is generated and transmitted from the electrosurgical generator to the electrosurgical instrument and how the electrosurgical instrument will apply the RF energy to the tissue. Furthermore, the electrosurgical system can monitor the progress of the sealing process and modify the generation and delivery of the RF energy to correspond to the state of the sealing process. In various other embodiments, the electrosurgical system can obtain various information about the tissue undergoing the sealing process and customize the aspects (e.g., voltage ramp, duration) about the sealing process.

The various features and embodiments provided throughout can be used alone, or in combination with other features and/or embodiments other than as expressly described and although specific combinations of embodiments and features or aspects of various embodiments may not be explicitly described such combinations however are contemplated and within the scope of the present inventions. Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

DETAILED DESCRIPTION

The present application pertains to an electrosurgical system that is configured to perform a variety of different surgical procedures such as fusing, cutting, and sealing tissue. The electrosurgical system includes at least an electrosurgical generator and a removably coupled electrosurgical instrument. The electrosurgical system is configured to obtain information about tissue undergoing the sealing process, calculate (in-real time) an appropriate amount of RF energy that will be provided to the electrosurgical instrument, and modify existing RF energy being generated to transmit to the electrosurgical instrument. The electrosurgical instrument is configured to use the provided RF energy in connection with the different surgical procedures (e.g., seal tissue).

As described in further details below, the calculations and determinations performed by the electrosurgical system can be based on a variety of different factors such as the electrosurgical instrument being used, the type, volume, and/or thickness of the tissue in contact with the electrosurgical instrument, and/or the surgical procedure being performed with the electrosurgical system. With the capabilities of the electrosurgical system, a variety of benefits will be realized (e.g., balance of hemostasis reliability, seal time, and tissue adherence) and will be further described below. Although the following application will primarily reference the electrosurgical system being used in connection sealing tissue, it should be noted that the electrosurgical system may be configured to be used in any number of other surgical procedures as well as in connection with a wide range of different tissues types, conditions, thicknesses, and/or volumes.

Overview

Figure 1:
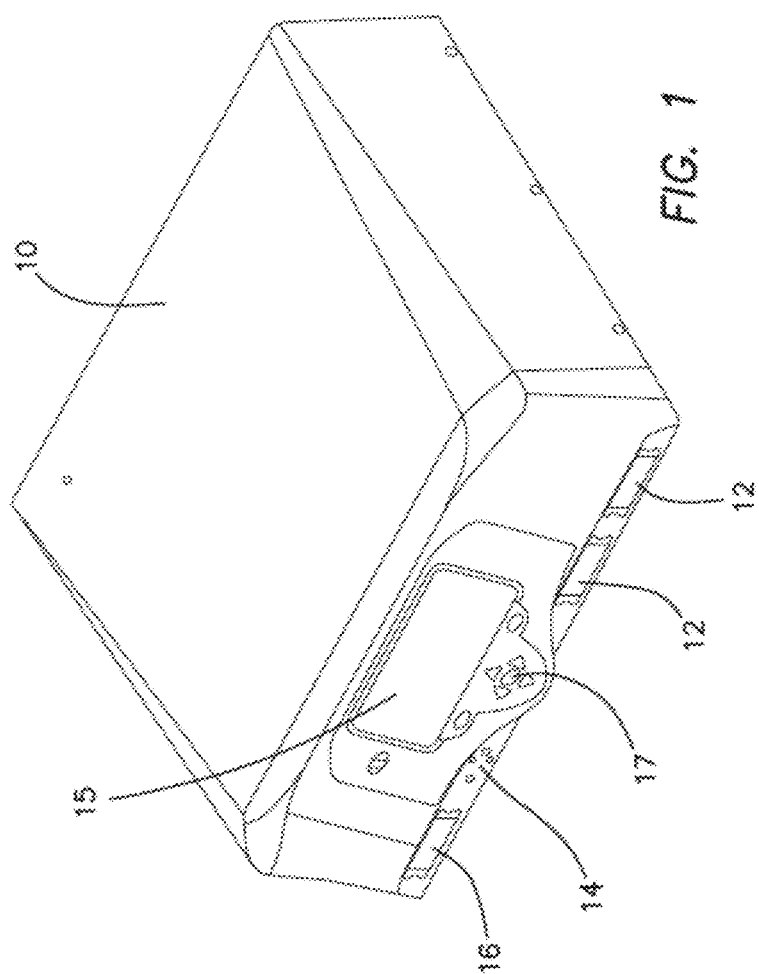
FIG. 1 is a perspective view of an electrosurgical generator in accordance with various embodiments of the present invention.
Figure 2:
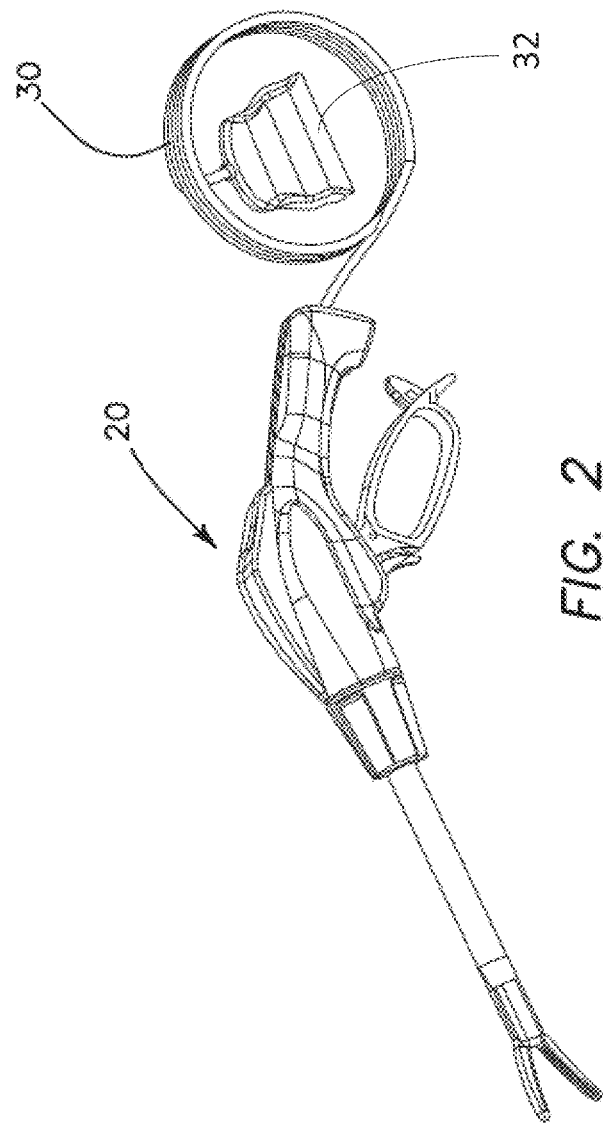
FIG. 2 and FIG. 3 are perspective views of an electrosurgical instrument in accordance with various embodiments of the present invention.
Figure 3:
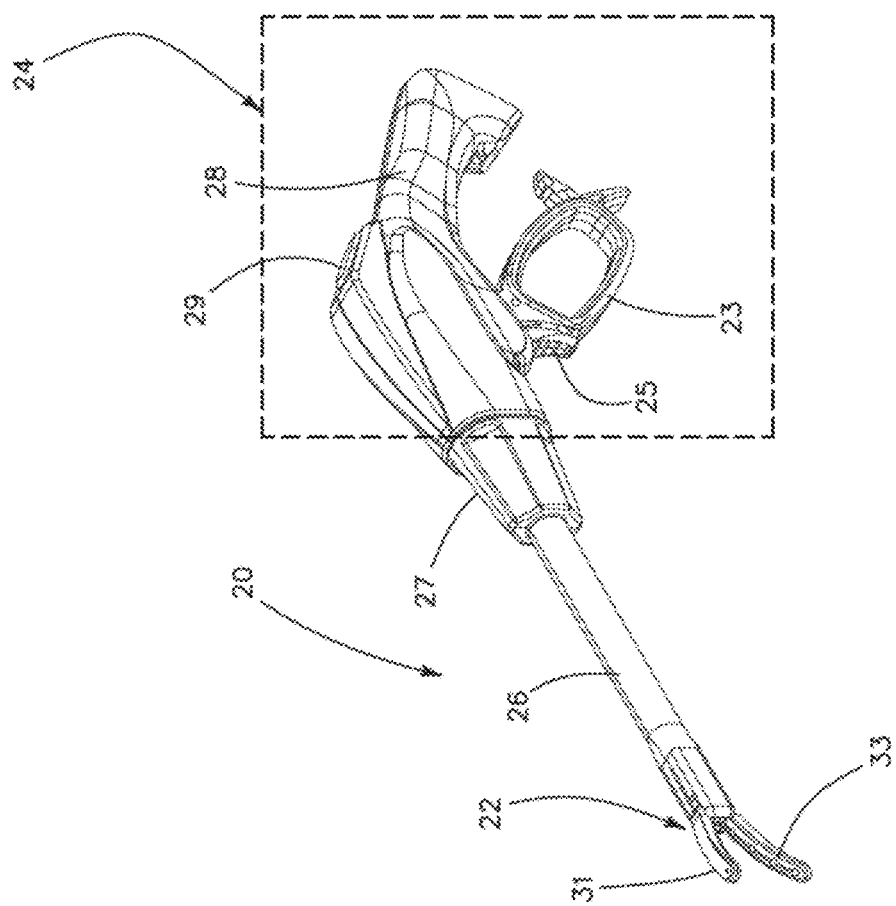

FIG. 1 to FIG. 3 illustrate components of an exemplary embodiment of an electrosurgical system. In particular, the electrosurgical system comprises an electrosurgical generator 10 (as illustrated in FIG. 1) and a removably connectable electrosurgical instrument 20 (as illustrated in FIG. 2 and FIG. 3). Details about each of the components will be provided below in further detail.

FIG. 1 is a perspective view of an electrosurgical generator 10 in accordance with various embodiments of the present invention. The electrosurgical generator 10 may be configured to 1) generate an appropriate amount of radiofrequency (RF) electrosurgical energy (referred herein as RF energy) used to carry out a surgical procedure (e.g., sealing tissue), 2) receive data or information about the tissue (e.g., from a connected electrosurgical instrument) to determine how to control/manage the generation and transmission of the RF energy in connection with the surgical procedure, and 3) modify the RF energy based on the received data or information.

In one embodiment, the electrosurgical generator 10 may be configured to output RF energy in accordance to a variety of different parameters that include voltage, current, power, and/or phase (e.g., 375 VA, 150V, 5 A at 350 kHz). To calculate how much RF energy needs to be generated and determine how to transmit that RF energy (e.g., voltage profile), the electrosurgical generator may be configured to 1) measure the current and/or voltage associated with the RF energy currently being generated, 2) calculate a power measurement of the RF energy, and/or 3) calculate a phase angle or difference between the RF output voltage and the RF output current during activation or supply of the RF energy from the electrosurgical generator 10. Based on the calculations and determinations performed by the electrosurgical system, the electrosurgical generator 10 may also be instructed to regulate voltage, current, and/or power accordingly. For example, the electrosurgical generator 10 may be instructed to stop the output of the RF energy under predefined conditions such as when a device switch is de-asserted (e.g., fuse button is released), a time value is met, and/or a measured active phase angle, current, voltage, power and/or changes thereto is greater than, less than, or equal to a stop value, threshold, or condition and/or changes thereto.

As illustrated in FIG. 1, the exemplary embodiment of the electrosurgical generator 10 used for surgical procedures (e.g., sealing tissue) comprises at least one advanced bipolar instrument port 12, a standard bipolar instrument port 16, and an electrical power port 14. In other embodiments, the electrosurgical generator 10 can comprise any different numbers of ports. For example, in some embodiments, the electrosurgical generator 10 can comprise more or fewer than two advanced bipolar instrument ports 12, more or fewer than the standard bipolar instrument port 16, and more or fewer than the electrical power port 14. In one embodiment, the electrosurgical generator 10 comprises only one advanced bipolar instrument port 12.

In accordance with various embodiments, the advanced bipolar instrument ports 12 may be configured to be coupled to an electrosurgical instrument (as illustrated in FIG. 2 and FIG. 3) having an attached or an integrated memory module. The memory module (described in further details below) can contain operational data usable by the electrosurgical instrument. The operational data can be used by the electrosurgical generator 10 to configure not only the operations of the corresponding electrosurgical instrument but also can be used to configure one or more operations performed by the electrosurgical generator 10 (e.g., performance preferences specific for the electrosurgical instrument). The standard bipolar instrument ports 16 may be configured to receive a non-specialized bipolar electrosurgical instrument that differs from the advanced bipolar electrosurgical instrument connectable to the advanced bipolar instrument port 12.

The electrical power ports 14 may be configured to receive or be connected to a direct current (DC) accessory device that differs from the non-specialized bipolar electrosurgical instrument (connected to the standard bipolar instrument port 16) and the advanced bipolar electrosurgical instrument (connected to the advance bipolar instrument port 12). Specifically, the electrical power port 14 may be configured to supply direct current voltage (e.g., 12 Volts DC). The electrical power port 14 can also be configured to provide power to a surgical accessory, such as a respirator, pump, light, or any another surgical accessory. With the feature of the electrical power port 14, the electrosurgical device 10 is capable of replacing power supplies for surgical accessories. In some embodiments, replacing presently-existing generators and power supplies with the electrosurgical generator 10 described in this application can reduce the amount of storage space required on storage racks cards or shelves (e.g., reducing a number of power cords required in a surgical workspace).

The electrosurgical generator 10 can further comprise a display 15. The display 15 can be used to display a status of the electrosurgical system including, among other information, the status of the electrosurgical generator 10 (e.g., current RF energy output, measured parameters associated with the RF energy) and one or more connected electrosurgical instruments and/or accessories, connectors, or connections thereto.

The electrosurgical generator 10 can also comprise a user interface 17 that allows user interaction with the electrosurgical generator 10 such as, for example, requesting an increase or decrease in the amount of RF energy being supplied to one or more electrosurgical instruments coupled to the electrosurgical generator 10. In some embodiments, the user interface 17 may be implemented as a plurality of buttons (e.g., keyboard, number pad, arrows). In other embodiments, the user interface 17 can be integrated with the display 15 such that the display 15 is a touch screen display. The touch screen display would allow for the display of any status-related information as well as the buttons associated with carrying out the functions of the user interface 17.

In some embodiments, electrosurgical generator 10 can further comprise of one or more memory modules. The memory module may act as computer memory associated with the electrosurgical generator 10 and be used to store operational data concerning any number of different connected electrosurgical instruments. For example, in some embodiments, the operational data stored in the memory modules may include configuration-related information that can be used by a processor to configure/re-configure electrodes for the electrosurgical instruments. Other embodiments may have the operational data include information that can be used by the electrosurgical generator 10 to configure/re-configure processes of the electrosurgical generator 10 to work with/become compatible with the electrosurgical instruments. For example, the electrosurgical generator 10 may be configured based on the operational data to adjust operational time, voltage, power, phase and/or current settings, and/or adjust operational states, conditions, scripts, processes, or procedures pertaining to the surgical procedure being performed. Furthermore, the electrosurgical generator 10 (via the processor) can initiate read processes to obtain the operational data stored in the memory module (or stored in the memory module of connected electrosurgical instruments) to configure/re-configure the operation of the electrosurgical generator 10. The electrosurgical generator 10 can also initiate write processes to update and store operational data to the memory module (or memory modules of connected electrosurgical instruments) for later use.

To facilitate in the real-time calculations of how much RF energy should be generated and the determination of how the RF energy should provided to the electrosurgical instrument, one embodiment of the electrosurgical generator 10 has the electrosurgical generator 10 monitoring various parameters (e.g., voltage, current) and calculating the phase difference or phase angle of the RF energy currently being transmitted to the connected electrosurgical instrument. As such, while tissue is undergoing the sealing cycle, the monitored parameters and phase calculations from the electrosurgical system can be used to identify a current status of the sealing process (e.g., condition of the tissue) and whether the electrosurgical system should proceed to a different state, operation or step. As described below in further detail other mechanisms/methods (aside from using phase readings) can also be used to identify the current status of the sealing process and determine when the electrosurgical system should proceed through to subsequent steps/operations/states in the seal cycle.

In an embodiment, the electrosurgical generator 10 can be configured to monitor and measure a variety of different parameters (e.g., current, power, impedance, or power) associated with the RF output and calculate information (e.g., phase, power, thresholds) based on the same. By using the calculated information, the electrosurgical generator 10 can automatically configure how much RF energy should be generated and how the RF energy is being transmitted to any connected electrosurgical instrument. As an example, the electrosurgical generator may be able to adjust one or more parameters of the RF energy (e.g., adjusting a voltage level) that can influence the amount or how the RF energy (e.g., having an associated voltage profile) is being delivered to the electrosurgical instrument. As such, the electrosurgical system can control the output of the RF energy to the electrosurgical instrument thereby influencing how the sealing is performed on the tissue without involvement by a user (e.g., surgeon).

Once the electrosurgical generator 10 starts to deliver the RF energy to the connected electrosurgical instrument, the electrosurgical generator 10 can be configured to continue delivering the RF energy continuously (e.g., every 150 ms) until a fault occurs or a specific condition (e.g., % threshold, time period) is satisfied. In the situation where the fault occurs or the specific condition is satisfied (e.g., end of the sealing cycle), the electrosurgical generator 10 may transition to the next step or operation immediately. In some embodiments, the electrosurgical generator 10 may pause or wait a predetermined period of time (i.e. time delay) before commencing the next step or operation. Further details about the operations of the electrosurgical generator 10 in connection with the sealing of tissue (e.g., seal cycle) will be provided below.

With respect to FIG. 2 and FIG. 3, the figures are perspective views of an electrosurgical instrument 20 in accordance with various embodiments of the present invention. The electrosurgical instrument 20 is adapted to receive RF energy from the electrosurgical generator via a cabled connection 30 to use in the sealing process with tissue in contact with the electrosurgical instrument 20 (specifically clamped between the jaw assembly 22). In particular, the electrosurgical instrument 20 can be coupled to the electrosurgical generator (of FIG. 1) via the cabled connection 30 that includes an adaptor 32. The adaptor 32 is designed so that the cabled connection can be used to connect the electrosurgical instrument 20 with one of the device ports (e.g., 12, 16) on the electrosurgical generator. This allows, in some embodiments, the electrosurgical instrument 20 to be reusable and/or removably connectable with a variety of different electrosurgical generators so that the electrosurgical instrument 20 can be compatible for multiple different surgical procedures. In some embodiments, a manual controller (e.g., a hand or foot switch) can be removably connected to the electrosurgical generator and/or electrosurgical instrument 20 to allow predetermined selective control over the electrosurgical instrument 20 such as when to commence a fusion or cut operation.

In some embodiments, the electrosurgical instrument 20 may include audio, tactile and/or visual indicators. The indicators allow the user (e.g., surgeon) to be apprised of information associated with the electrosurgical instrument 20 during a surgical procedure. For example, the information may include an indication (e.g., a beep, vibration, light) of a fusion, cut, and/or sealing operation being performed.

FIG. 3 provides further details of the electrosurgical instrument 20 illustrated in FIG. 2. In the figure (illustrating an exploded view of the electrosurgical instrument 20), the electrosurgical instrument 20 includes an actuator 24 coupled to an elongate rotatable shaft 26. The elongate rotatable shaft 26 has a proximal end and a distal end that defines a central longitudinal axis therebetween. At the distal end of the elongate rotatable shaft 26 is a jaw assembly 22 (which comprises a first jaw 31 and a second jaw 33) used to grasp tissue. At the proximal end of the elongate rotatable shaft 26 is the actuator 24. In one embodiment, the actuator 24 is a pistol-grip like handle.

The actuator 24 provides means for a user (e.g., surgeon) to operate the electrosurgical instrument 20. For example, the actuator 24 may comprise a movable handle 23 and a stationary handle or housing 28. The movable handle 23 may be coupled and movable relative to the stationary handle or housing 28. In some embodiments, the movable handle 23 is slidably and pivotally coupled to the stationary handle or housing 28. In operation, the movable handle 23 is manipulated by the user (e.g., a surgeon) to actuate the jaw assembly 22, for example, selectively opening and closing each of the jaws of the jaw assembly 22 to release and grasp tissue therebetween.

In accordance with various embodiments, the actuator 24 may include a latch mechanism to allows the movable handle 23 to be maintained in a second position with respect to the stationary handle or housing 28. In various embodiments, the movable handle 23 comprises a latch arm which engages a matching latch contained within the stationary handle or housing 28. The latch arm is configured to hold the movable handle 23 at a second or closed position. The latch mechanism provides a feature for the electrosurgical instrument 20 whereby the jaw assembly 22 can remain closed (i.e. locked). This allows tissue that is grasped within the jaw assembly 22 to remain between the first and second jaws 31, 33 minimizing the scenario where the first and second jaws 31, 33 are accidentally released by the user during the surgical procedure.

The actuator 24 in various embodiments also comprises a wire harness that includes insulated individual electrical wires or leads contained within a single sheath. The wire harness can exit the stationary handle or housing 28 at a lower surface thereof and form part of the cabled connection (see reference 30 of FIG. 2). The wires within the harness can provide electrical communication between the electrosurgical instrument 20 and the electrosurgical generator and/or accessories thereof.

In various embodiments, the electrosurgical instrument 20 can also include a switch that is connected to a user manipulatable activation button 29. The switch can become activated when the activation button 29 is depressed. In one aspect, once activated, the switch completes an internal circuit by electrically coupling at least two leads together. The internal circuit acts as an electrical path from an electrosurgical generator to the actuator 24 and would be used as a way to transfer a supply of RF energy from the electrosurgical generator to, for example, the electrodes associated with the jaw assembly 22.

In various embodiments, the electrosurgical instrument 20 can also comprise a translatable mechanical cutting blade. The translatable mechanical cutting blade can be coupled to a blade actuator such as a blade lever or blade trigger 25 of the actuator 24. The mechanical cutting blade is actuated by the blade trigger 25 to divide the tissue between the jaws of the jaw assembly 22. When the user actuates (e.g., presses down on) the blade trigger 25, the translatable mechanical cutting blade (which is initially sheathed internally within a blade channel) can extend or become unsheathed towards the distal end of the elongate rotatable shaft 26. The blade channel can be positioned along one of the jaws of the jaw assembly 22. The unsheathing of the mechanical cutting blade provides the movement that allows for the cutting of tissue that is grasped between the jaw assembly 22 by the translatable mechanical cutting blade. The user (e.g., surgeon) is able to control the speed and depth of the cut based on the way the blade trigger 25 is pressed. Once the cut of the tissue has been completed, the user can release the blade trigger 25 thereby allowing the mechanical cutting blade to return back to a sheathed position within the blade channel.

In one embodiment, the actuator 24 includes a rotation shaft assembly including a rotation knob 27 which is disposed on an outer cover tube of the elongate rotatable shaft 26. The rotation knob 27 allows a user (e.g., surgeon) to rotate the elongate rotatable shaft 26 of the electrosurgical instrument 20 (and in turn the jaw assembly 22) while gripping the actuator 24. In accordance with various embodiments, the elongate rotatable shaft 26 comprises an actuation tube coupling the jaws of the jaw assembly 22 with the actuator 24. This feature may allow the user (e.g., surgeon) to position the jaws in an orientation that can be used to better grasp tissue.

As described above, attached to the distal end of the elongate rotatable shaft 26 are jaws of the jaw assembly 22. In particular, the jaw assembly 22 comprises a first (or upper) jaw 31 and a second (or lower) jaw 33. One or both of the jaws of the jaw assembly 22 are movable/pivotable in response to user interaction with the actuator 24 (e.g., moving the movable handle 23 to a position proximate to the stationary handle or housing 28. In one embodiment, a jaw pivot pin pivotally couples the first jaw 31 and the second jaw 33 and allows one of the jaws (e.g., the first jaw 31) to be movable and pivotable relative to the other jaw (e.g., the second jaw 33). In other embodiments, one jaw (e.g., the first jaw 31) can be fixed with respect to the elongate rotatable shaft 26 such that the opposing jaw (e.g., the second jaw 33) pivots with respect to the fixed jaw (e.g., the first jaw 31) between an open and a closed position. In another embodiment, both the first and second jaws 31, 33 can be pivotally coupled to the elongate rotatable shaft 26 such that both the first and second jaws 31, 33 can pivot with respect to each other.

The first (or upper) jaw 31 may include an electrode (e.g., plate or pad). Similarly, the second (or lower) jaw 33 may also include an electrode (e.g., plate or pad). The electrode of the first jaw 31 and the electrode of the second jaw 33 may be electrically coupled to the electrosurgical generator via wires and connectors. The electrodes of the first and second jaws 31, 33 are arranged to have opposing polarity and to transmit RF energy therebetween. In this way, the electrosurgical generator can supply RF energy to tissue grasped between the electrodes of the first and second jaws 31, 33.

The first jaw 31 in various embodiments can also include an upper jaw support with an assembly spacer positioned between the first jaw support and the electrode connected to the first jaw 31. In some embodiments, the first jaw 31 can include an overmold while in some other embodiments, the first jaw 31 is overmolded. In addition, the second jaw 33 can include a lower jaw support and the electrode. In the illustrated embodiment, the electrode is integrated or incorporated in the lower jaw support and thus the lower jaw support and the electrode form a monolithic structure and electrical connection.

In connection with cutting tissue, the blade channel can extend longitudinally along the length of the first jaw 31, the second jaw 33, or both the first and second jaws 31, 33 through which the mechanical cutting blade operationally traverses. Surrounding a portion of the blade channel are one or more conductive posts. The conductive posts assist in strengthening the blade channel and support the tissue to be cut. The conductive posts also assist in ensuring the tissue being cut adjacent or proximate to the blade channel is fused as the conductive posts also participate in the transmission of RF energy to the tissue grasped between the first and second jaws 31, 33. Much like the first jaw 31, some embodiments may have the second jaw 33 include an overmold while other embodiments the second jaw 33 is overmolded.

In accordance with various embodiments, the electrodes associated with the first and second jaws 31, 33 may each have a generally planar sealing surface arranged to atraumatically contact and compress tissue captured between the first and second jaws 31, 33. In some embodiments, the electrodes of the first and second jaws 31, 33 have a seal surface in which the width of the seal surface is uniform, constant, or remains unchanged throughout.

In various embodiments, the first and second jaws 31, 33 may be curved to increase visualization and mobility of the first and second jaws 31, 33 at the targeted surgical site and during the surgical procedure (e.g., sealing tissue). The first and second jaws 31, 33 may have a proximal elongate portion that is denoted or aligned with straight lines and a curved distal portion denoting or defining a curve that is connected to the straight lines. In various embodiments, the proximal most portion of the proximal elongate portion has or delimits a diameter that equals or does not exceed a maximum outer diameter of the first and second jaws 31, 33 or elongate rotatable shaft 26. The first and second jaws 31, 33 in various embodiments may have a maximum outer diameter in which the proximal most portion of the jaw assembly 22 and the distal most portion of the jaw assembly 22 remains within the maximum outer diameter. The curved distal portion has or delimits a diameter that is smaller than the maximum outer diameter and the diameter of the proximal most portion of the proximal elongate portion. In various embodiments, the first and second jaws 31, 33 may have a deeper inner curve cut-out than the outer curve and in various embodiments the tip of the first and second jaws 31, 33 are tapered for blunt dissection. The jaw assembly 22 can include a blade channel having a proximal elongate channel curving to a distal curved channel in which the proximal elongate channel is parallel and offset to the longitudinal axis of the elongate rotatable shaft 26 of the electrosurgical instrument 20. As such, visibility and mobility at the first and second jaws 31, 33 are maintained or enhanced without increasing jaw dimensions as increase jaw dimensions may further reduce the surgical working area or require larger access devices or incisions into the patient's body.

In some embodiments, electrode geometry of the conductive pads of the jaw assembly 22 ensures that the sealing area or surface completely encloses the distal portion of the cutting path. In accordance with various embodiments, the dimensions of the surfaces of the first and second jaws 31, 33 are such that it is appropriately proportioned with regards to the optimal pressure applied to the tissue between the first and second jaws 31, 33 for the potential force the force mechanism can create. The surface area of the jaw assembly 22 is also electrically significant with regards to the surface area contacting the tissue. This proportion of the surface area and the thickness of the tissue have been optimized with respect to its relationship to the electrical relative properties of the tissue.

In various embodiments, the second (or lower) jaw 33 and an associated conductive pad have an upper outer surface arranged to be in contact with tissue. The upper surfaces are angled or sloped and mirror images of each other with such positioning or orientation facilitating focused current densities and securement of tissue. In various embodiments, the second jaw 33 is made of stainless steel and is as rigid as or more rigid than the conductive pad. In various embodiments, the second jaw 33 comprises rigid insulators made of a non-conductive material and are as rigid as or more rigid than the second jaw 33 or the conductive pad. In various embodiments, the second jaw 33 and the conductive pad are made of the same material.

Figure 4:
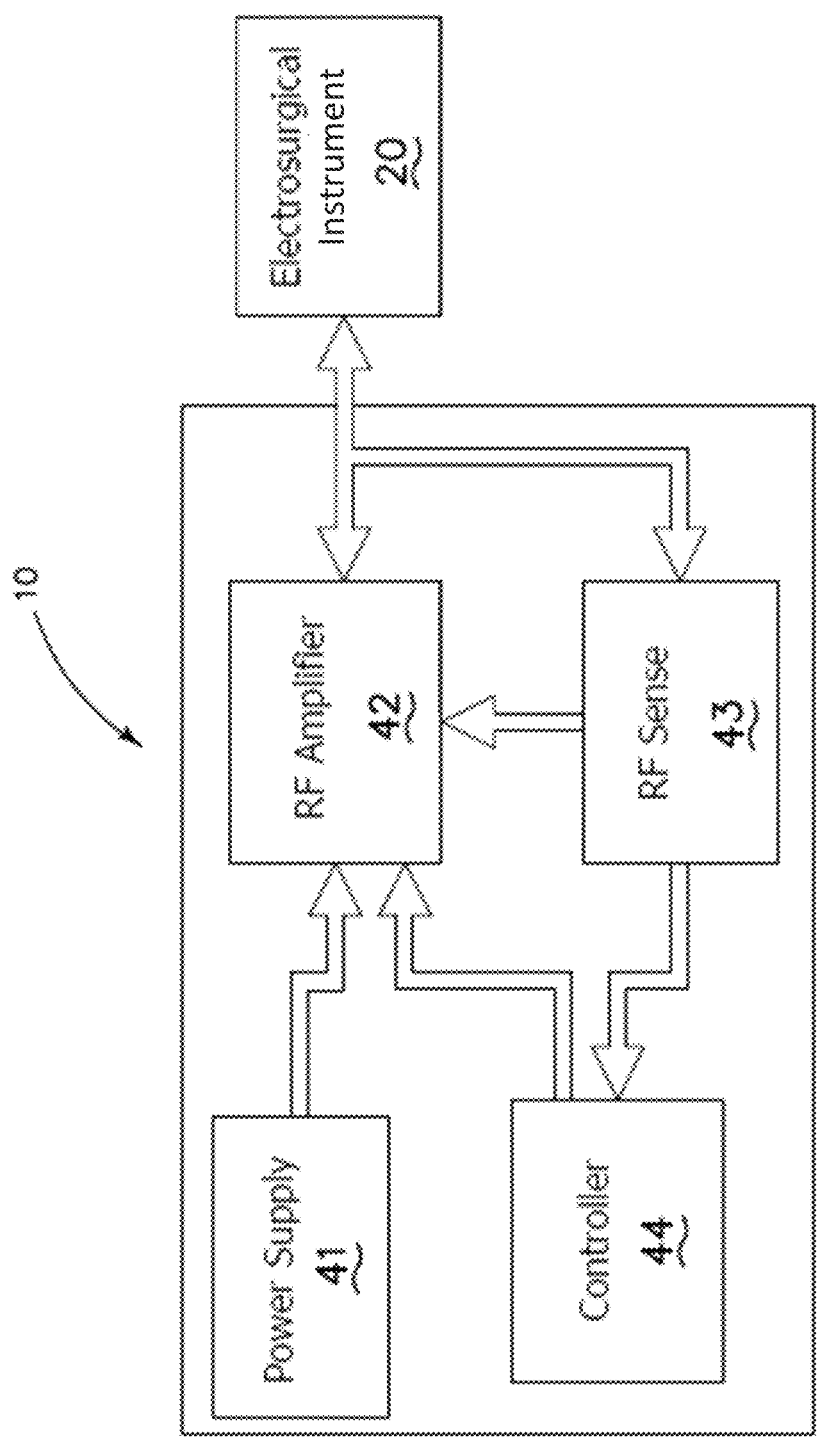
FIG. 4 is a block diagram illustrating an exemplary electrosurgical system in accordance with various embodiments of the present invention.

FIG. 4 is a block diagram illustrating an exemplary electrosurgical system in accordance with various embodiments of the present invention. As illustrated in the figure, the electrosurgical system includes the electrosurgical generator 10 (illustrated in FIG. 1) and the electrosurgical instrument 20 (illustrated in FIG. 2 and FIG. 3). The electrosurgical generator 10 can be connected to an AC (alternating current) main input. A power supply 41 associated with the electrosurgical generator 10 can then be used to convert the AC voltage from the AC main input to DC voltages. The DC voltages will be used to power various circuitry of the electrosurgical generator 10. The power supply 41 also supplies DC voltage to an RF amplifier 42.

Generally, the RF amplifier 42 can be used to generate the RF energy that will be provided to the electrosurgical instrument 20 in connection with the surgical procedures (e.g., sealing tissue). For example, the RF amplifier 42 can be configured to convert 100V DC from the power supply 41 into a sinusoidal waveform with a frequency of 350 kHz. The converted RF energy can then be delivered to the electrosurgical instrument 20 where the RF energy is applied to tissue in contact with the electrosurgical instrument in connection with a sealing process.

The electrosurgical generator 10 may also include a RF sense circuitry 43. The RF sense circuitry 43 provides the electrosurgical generator the capability to monitor and measure various different parameters (e.g., voltage, current, power, phase) of the RF energy as well as perform calculations based on the measurements. Generally, the RF sense circuitry 43 can be configured to measure parameters (e.g., voltage, current) in analog, convert the analog measurements to a digital format, process the measurements via an FPGA to calculate RMS values associated with the measured parameters, calculate apparent power and phase angle, and convert the digital data back to analog for use by the controller 44.

In art embodiment, the RF sense circuitry 43 can be configured to monitor the voltage and current of RF energy coming from the RF amplifier 42. After obtaining the measurements, the RF sense circuitry 43 can perform a number of calculations based on the measurements such as the root means square (RMS) of the voltage and current, apparent power of the RF output energy, and the phase angle between the voltage and current of the RF energy being supplied through the connected electrosurgical instrument 20. The calculations can be performed using analog circuitry associated with the RF sense circuitry 43 to generate real and imaginary components of both voltage and current. The information associated with the calculations are processed by a field-programmable gate array (FPGA). Ultimately, the RF sense circuitry 43 will aim to generate signals that can be sent to the controller 44 for further processing.

As noted above, the information produced by the RF sense circuitry 43 can be provided to a controller 44. In various embodiments, the controller 44 controls or signals to the RF amplifier 42 whether any changes to the RF energy need to be made and/or how to modify the RF energy being provided to the electrosurgical instrument 20. For example, the controller 44 can utilize the information provided by the RF sense circuitry 43 to determine if the RF energy being provided via the RF amplifier 42 should be outputted as is, adjusted, or terminated. In one embodiment, the controller 44 determines if or when a predetermined current, power, and/or phase threshold has been reached or exceeded. When a threshold has been reached or exceeded, the controller 44 can use this detected event to determine, for example, the current state of the surgical process, what how the RF energy should be adjusted to correspond to the next step of the surgical process, and whether to terminate the output of RF energy. In various embodiments, the controller 44 is configured to assist in the surgical process (e.g., sealing process of tissue) by detecting various thresholds and providing instructions that control the RF energy output based on what step of the surgical process is being performed. In other embodiments, the controller 44 can be configured to receive instructions, settings, and/or script data to assist in the performance of the surgical process (e.g., sealing process) from a memory module. The memory module may be associated with the electrosurgical generator 10. In some cases, the memory module may be associated with the electrosurgical instrument 20.

As an example, different thresholds may be associated with different conditions associated with a particular type of tissue during a sealing process. As the tissue undergoes sealing, fluid/water is removed from the tissue so that the tissue can be cut and/or fused together. As the remaining amount of fluid/water is removed from the tissue (corresponding to different stages of the sealing process), a corresponding threshold (e.g., measured current) can be used to signify when the current stage is detected. The thresholds can then be used to modify (e.g., reduce) an amount of RF energy that is provided to the tissue. For example, as the tissue becomes more desiccated, less energy would be necessary to remove the remaining fluid/water within the tissue. In controlling the RF energy, the electrosurgical generator 10 can minimize the possibility of damaging the tissue via, for example, burning thereby minimizing recovery time for the patient.

In some embodiments, the controller 44 may include an operations engine that enables the electrosurgical generator 10 to be configurable to accommodate different operational scenarios (e.g., different electrosurgical instruments, different surgical procedures, different user preferences). For example, the operations engine of the controller 44 can be configured to receive and interpret data from the memory module (e.g., pluggable memory device inserted into the electrosurgical generator 10 or associated with the electrosurgical instrument 20). Information (e.g., configuration data) stored therein can be used to configure the electrosurgical generator 10. For example, the information can define state logic used by the electrosurgical generator 10, define and/or set output levels for the RF energy, define and/or set shutoff criteria for the RF energy, identify error conditions (e.g., electrical short circuit condition, electrical open circuit condition).

The RF sense circuitry 43 and the controller 44 work together in order to ensure that parameters associated with the currently outputted RF energy are within predefined threshold ranges or windows. Example threshold ranges or windows can be delimited by predetermined maximum and minimum voltages, currents, phases, and/or power that correspond to expected conditions associated with the currently outputted RF energy. In some cases, if measurements of one or more parameters (e.g., voltage, current, phase, power) are found to be outside the predefined threshold range or window, an error can be identified and the user is subsequently notified accordingly. In other cases, measurements found to be outside of the predefined threshold range or window can be used to identify transitioning to a next step of the surgical process. Accordingly, the predefined threshold range or window can then be adjusted accordingly based on the next step being transitioned to. In another case, if the predefined threshold range or window is breached, the electrosurgical system can be instructed to terminate (e.g., end the supply of RF energy) immediately or after a predetermined period of time.

In accordance with various embodiments, the controller 44 can be configured to provide regulation control of various parameters (e.g., voltage, current, power and/or phase) or functions related to the output of the RF energy by the RF amplifier 42. For example, the controller 44 can be configured to utilize one or more of the parameters or functions in order to determine when and how to adjust the output of RF energy. In one exemplary embodiment, the controller 44 can be configured to provide regulation controls for direct regulation of one or more parameters that, when adjusted, would satisfy specific thresholds (e.g., regulation set points).

In accordance with various embodiments, the electrosurgical generator 10 can use the monitored, measured and/or calculated values of parameters (e.g., voltage, power, current and/or phase) associated with the RF energy as control indicators to identify a current state of the surgical process (e.g., condition of the tissue such as the tissue reaching a point of desiccation or an estimate amount of fluid/water that still needs to be removed from the tissue) as well as identify next steps to be performed in the surgical process (e.g., adjusting the amount of RF energy being applied to the tissue in the sealing process). In various embodiments, additional measurements or calculations based on the measured values related to RF output regulation circuitry can be provided via a script that can be used to recognize and act upon additional or different events related to or triggered by the additional measurements or calculations. The additional measurements described above may include error signals in combination with a pulse width modulation (PWM) duty cycle that is used to regulate various RF energy output parameters (e.g., voltage, current and/or power). Different or additional events or indicators that could be identified and triggered in various embodiments could be used as transitions from one regulation control to another regulation control (e.g. changing from current regulation to power regulation).

In various embodiments, the electrosurgical generator 10 can be configured to utilize many states, control points, or checks corresponding to different steps of a surgical process. The electrosurgical generator 10 can identify which state, control point, or check is present based on identifying a current parameter value (e.g., phase, current, or power) and determining whether the parameter value is expected for the present state, control point or check or for a different state, control point or check. Furthermore, the electrosurgical generator 10 can be configured to evaluate whether a change in the current parameter value has a positive or negative trend to determine whether the next state, control point, or check is to be expected to occur soon. An error can be signaled if the electrosurgical generator 10 does not identify an expected or predefined trend. The use of the multiple states, control points and checks and/or circuitry related thereto increase or enhance the resolution associated with the electrosurgical generator in identifying an expected RF output trend over different types of tissue.

The electrosurgical generator 10 can also be configured to detect the occurrence of an electrical open or short circuit condition. The electrosurgical generator 10 is able to do so by monitoring, for example, the phase or current and/or rate of change associated with the phase or current. In one example, the electrosurgical generator 10 can be configured to identify that an electrical short condition of the connected electrosurgical instrument 20 is present by monitoring the phase of the outputted RF energy and determining that the monitored phase is greater than a predefined maximum phase value. Similarly, the electrosurgical generator 10 can also identify whether an electrical open condition is present in the connected electrosurgical instrument 10 by monitoring the current of the outputted RF energy and determining that the monitored current is less than a predefined minimum current. For both scenarios, the detection of the short or open circuit condition causes the electrosurgical generator 10 to flag that an error is present. Furthermore, the electrosurgical generator 10 can terminate/halt the RF energy being supplied to the connected electrosurgical instrument 20 by, for example, signaling the RF amplifier to halt supply of RF energy or deactivating a relay or switch connected to the output port of the generator.

Up to this point, the present application has described different aspects of the electrosurgical system—in particular, the features of the electrosurgical generator and the electrosurgical instrument. Details will now be provided with respect to the use of the electrosurgical system in connection with surgical procedures (e.g., sealing tissue). Although sealing tissue will be used as the exemplary surgical procedure in connection with the electrosurgical system, one skilled in the art can configure the described electrosurgical system herein to be compatible with other surgical procedures.

During an exemplary sealing process, the user (e.g., surgeon) may visually identify/select a portion of tissue that the user intends to seal. Once the tissue has been identified/selected, the jaw assembly 22 of the electrosurgical instrument 22 (e.g., the first and second jaws 31, 33) can be placed around the identified/selected tissue. The movable handle 23 can then be maneuvered to the closed position so as to have the first and second jaws 31, 33 clamp together to effectively grasp the tissue. Once the tissue has been grasped within the jaw assembly 22, the depression of the activation button 29 by the user (e.g., surgeon) can initiate the sealing process on the tissue by allowing for the application of the RF energy coming from the electrosurgical generator 10. When the tissue has been completed sealed, the jaw assembly can be reopened thereby releasing the tissue from the jaw assembly 22. The jaws of the electrosurgical instrument 20 can be opened to relieve compression on tissue being grasped by the jaws at any time (e.g., before or after the application of the RF energy). Further details on how the electrosurgical system (e.g., the electrosurgical generator 10) manages/modifies the RF energy being generated/supplied to seal the tissue via the electrosurgical instrument 20 will be provided below.

In accordance with various embodiments, the electrosurgical instrument 20 may have a first (i.e., open) state in which the first and second jaws 31, 33 are spaced from each other and thus the movable handle 23 is also spaced from the stationary handle or housing 28. The electrosurgical instrument 20 can then be positioned to have tissue in between the first and second jaws 31, 33 thereby allowing the electrosurgical instrument to grasp tissue between the first and second jaws 31, 33. In the second (i.e., intermediate) state of the electrosurgical instrument 20, the first and second jaws 31, 33 are proximate to each other thereby grasping tissue between the first and second jaws 31, 33. In this second state, the movable handle 23 and the stational handle or housing 28 are proximate to each other. The user (e.g., surgeon) can revert back to the first state by opening the jaw assembly 22 thereby allowing the user to again position the jaw assembly 22 to grasp the same area of tissue or grasp a different area of tissue altogether. In the third (i.e., closed) state of the electrosurgical instrument 20, the movable handle 23 is moved further closer to the stationary handle or housing 28 and latches to the stationary handle or housing 28. In some embodiments, the latching of the movable handle 23 to the stationary handle or housing 28 can lock the jaw assembly 22. With the movement to the third state, the tissue grasped between the jaw assembly 22 can be held in place. In this way, movement to the third state, in which the movable handle 23 is latched to the stationary handle or housing 28, reduces the potential event of unintentionally releasing the tissue. Furthermore, the third state can allow the tissue to be cut through via the activation of the blade trigger 25. The latching of the movable handle 23 to keep the grasped tissue in place also minimizes inadvertent cutting of tissue or along the wrong tissue lines. In some embodiments, the ability to cut tissue may only be allowed when the movable handle 23 is latched to the stationary handle or housing 28. Additionally, the third (closed) state allows the application of constant, continuous, and predefined compression or range of compression on the tissue between the first and second jaws 31, 33 before, during, and after the activation of the RF energy, thereby enhancing the sealing of the tissue between the first and second jaws 31, 33. In accordance with various embodiments, the application of RF energy can occur once the movable handle 23 and the jaw assembly 22 are in at least the second state and once the activation button 29 is activated by the user (e.g., surgeon). In some embodiments, the application of RF energy may only be allowed once the electrosurgical instrument is in the third state (e.g., the movable handle is latched to the stationary handle thereby locking the tissue in between the first and second jaws 31, 33).

In various embodiments, an intermediate or unlatched position is provided in which the first and second jaws 31, 33 are in a closed or proximate position but the movable handle 23 is unlatched. As such, if the movable handle 23 is released, the movable handle 23 will return to its original or initial position. In one embodiment, while the movable handle 23 is unlatched, the blade trigger 25 may not be capable of being activated to cut tissue between the first and second jaws 31, 33 but the activation button 29 may still be capable of being activated to seal tissue between the first and second jaws 31, 33. In various embodiments, a latched position is provided in which the first and second jaws 31, 33 are in a closed or proximate position and the movable handle 23 is latched. As such, if the movable handle 23 is released, the movable handle 23 will not return to its original or initial position thereby keeping the first and second jaws 31, 33 in the closed or proximate position. In one embodiment, while the movable handle 23 is latched, the activation button 29 may be capable of being activated to seal tissue between the closed jaw assembly 22 and/or the blade trigger 25 may be capable of being activated to cut tissue between the first and second jaws 31, 33.

In another process, the user (e.g., surgeon) can cut tissue between the first and second jaws 31, 33 of the electrosurgical instrument by actuating the blade trigger 25. When the blade trigger 25 is moved proximally, a cutting blade moves distally within a blade channel to divide the tissue between the jaw assembly 22. When the user (e.g., surgeon) releases the blade trigger 25, the blade spring resets the cutting blade to its original position (e.g., sheathed position within the blade channel). In accordance with various embodiments, the actuator 24 may have a cut condition in which the first and second jaws 31, 33 are in a closed position and the movable handle 23 is closed and latched before the depressing of the blade trigger 25 will allow for the advancing of the cutting blade to its distal most position.

Figure 5:
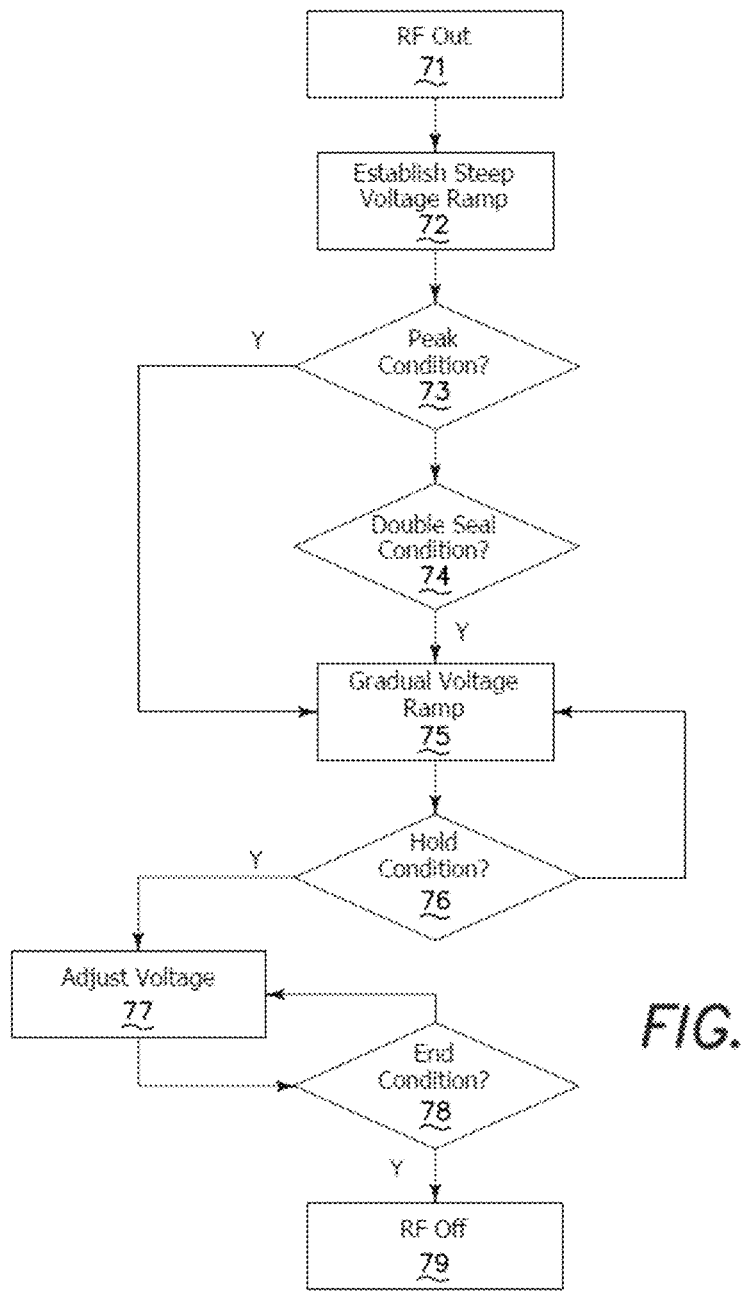
FIG. 5 is a flow chart illustrating operations of an electrosurgical system in accordance with various embodiments of the present invention.

FIG. 5 is a flow chart illustrating operations of an electrosurgical system described herein in accordance with various embodiments of the present invention. The exemplary process illustrated in the figure pertain to sealing tissue may be implemented using any number of different control processes or scripts. The control processes or scripts can be downloaded onto and executed by the electrosurgical system (e.g., via a processor contained therein). In one embodiment, the control processes or scripts can be stored and executed on the electrosurgical generator. In a different embodiment, the control processes and scripts can be stored on both the electrosurgical generator and the electrosurgical instrument. The steps described in FIG. 5, carried out by the processes or scripts, could also be implemented internally within the electrosurgical system without the need to download from an external source.

Provided below will be a general overview of the sealing process as well as a more detailed explanation in connection with the electrosurgical system described herein. Generally sealing tissue can involve first heating the tissue to an appropriate temperature where fluid/water within the tissue begins to vaporize (i.e., desiccation). The heating is carried out by providing an amount of RF energy with a high voltage ramp. This allows the temperature to be heated quickly.

Tissue fusion can generally occur around 60° C. as that's the temperature where collagen crosslinking begins to occur. To create a strong and durable seal, fluid/water must be removed from the tissue. The removal of the fluid/water allows the collagen and other protein structures in the tissue to crosslink with the rest of the biological structures of the tissue to create the durable seal. With the presence of fluid/water in the tissue, the collagen crosslinking will result in a gelatin-like substance which is less durable.

Once the vaporization of the fluid/water has been detected, the supply of the RF energy can be modified so that the temperature of the tissue is maintained at the current temperature to allow the vaporization of the fluid/water to continue at a controlled rate while preventing the possibility that the tissue becomes overheated. Furthermore, removal of the fluid/water too quickly from the tissue can create steam that can tear apart tissue and damage the seal being created.

Once all the fluid/water has been removed from the tissue, the RF energy being supplied to the tissue can be terminated. At this point, the sealing of the tissue has been completed.

With respect to the flowchart illustrated in FIG. 5, the flowchart describes an example process for sealing tissue using the electrosurgical system described in this present application. It should be noted that the process illustrated in the figure is one way the electrosurgical system can be configured to seal tissue. Other ways of sealing tissue would be possible as apparent to one skilled in the art based on the teachings of the electrosurgical system described in this application.

First, the electrosurgical system may begin with having the electrosurgical generator supply the RF energy to a connected electrosurgical instrument (71). The electrosurgical generator may initially set parameters associated with the generation of the RF energy being provided to the electrosurgical instrument. For example, the electrosurgical generator may generate the RF energy to have an initial voltage profile that has a steep voltage ramp (72). The initial parameters (e.g., voltage profile) may be default parameters for the electrosurgical generator. In some embodiments, operational data can be provided (e.g., by a user) to the electrosurgical generator that instructs how the electrosurgical system should generate the RF energy (e.g., data stored in a memory module, user input via the user interface). As an example, the RF energy may have a voltage profile that corresponds to an increase in voltage from an initial value of 40V to a maximum value of 60V over a pre-defined period of time (e.g., 75 ms). In another example, the voltage profile for the RF energy could be implemented instead by increasing current from an initial value of 2500 mA to a maximum value of 5000 mA over the same pre-defined period of time (e.g., 75 ms).

As the RF energy is being applied in the ramping manner (via 71 and 72) to the tissue during the initial period of time, the electrosurgical system can be monitoring one or more different parameters (e.g., voltage, current, phase, power) associated with the RF energy being applied to the tissue to detect when an RF output peak condition (73) has occurred. The electrosurgical system can then use the measured maximum current associated with the RF output peak condition to track a progress of the tissue undergoing the sealing process and manage the RF energy being used (as described below).

In one embodiment, the RF output peak condition can be detected by the electrosurgical system when one or more of the monitored parameters (e.g., voltage, current, phase, power) reaches a maximum value or peak. For example, the RF output peak condition can be identified (in 73) by monitoring the current being drawn into the tissue and identifying when the maximum amount of current has been drawn.

The electrosurgical system can also be configured to determine if a double seal/repeat seal condition is present (74). Double seal/repeat seal conditions correspond to situations where the tissue currently undergoing the sealing process was previously sealed. Previously sealed tissue already had some or all of the fluid/water removed from the tissue thereby requiring less RF energy to complete the seal. Therefore, the electrosurgical system is capable of identifying when to reduce the application of RF energy for the tissues that have already undergone one or more activations (e.g., previous sealing cycles). In doing so, the electrosurgical system can minimize or avoid negative effects such as eschar (sealed tissue debris) buildup, tissue adherence, and/or thermal spread.

To determine whether a double seal/repeat seal condition is present (in 74), the electrosurgical generator can monitor one or more parameters associated with the RF energy currently being applied to the tissue. A comparison can then be made by the electrosurgical system between the currently monitored parameter with a maximum value previously obtained associated with similar tissue. For example, a template may be used that stores a maximum value of similar tissue and/or pre-determined thresholds that can be compared with the currently monitored parameter. If the currently monitored parameter falls within a window or range (e.g., percentage of the maximum value), the electrosurgical system can determine that a double/repeat seal condition is present. Accordingly, the electrosurgical system can instruct the electrosurgical generator to modify the RF energy being delivered to the tissue based on the identified double/repeat seal condition (in 74). For example, since the tissue was previously sealed, a lesser amount of RF energy may instead be used to vaporize fluid/water from the tissue. Furthermore, the electrosurgical generator can also be instructed to move onto the next stage/step (e.g., 75) of the sealing cycle thereby limiting the amount of RF energy being provided to the tissue.

Once the electrosurgical system identifies the RF output peak condition (73) or identifies that a double/repeated seal condition is present (74), the electrosurgical system can modify the RF energy being provided to the tissue (in 75). In particular, the electrosurgical generator will aim to provide RF energy that can be used to continue/maintain the vaporization of the fluid/water from the tissue at a constant rate. As an example, the electrosurgical generator can adjust the voltage profile of the RF energy in order to implement a gradual voltage ramp (75). In this example, the electrosurgical system can instruct the electrosurgical generator to cause the RF energy to ramp gradually increasing from a predefined initial value (e.g., 35 V) to a maximum value (e.g., 45V) over a predefined time period (e.g., 500 ms). It should be noted that the predefined initial value is less than the maximum value measured for the tissue undergoing the sealing process (or similar tissue that previously underwent the sealing process) in order to minimize the possibility of overheating the tissue.

During the modification of the RF energy (in 75), the electrosurgical system can monitor for a hold condition (76). For example, as the electrosurgical generator gradually ramps the voltage for the RF energy, the electrosurgical system can monitor for a hold condition (in 76) to indicate when the ramping of the voltage should stop. The electrosurgical system, in various embodiments, may be configured to measure, calculate, and/or monitor various parameters (e.g., phase, voltage, current, power and/or change/rate thereof) associated with the supplied RF energy and the tissue undergoing the sealing process. If the hold condition is met (e.g., a measured phase and/or current reaches, exceeds, or falls below a predetermined threshold or static value), the RF energy currently being provided to the tissue can be maintained by the electrosurgical generator at its current state. For example, if the electrosurgical system measures a phase that reaches or falls below a predetermined threshold value and measures a current that reaches or falls below a predetermined threshold value, the electrosurgical generator can be instructed that a hold condition is met. Once the hold condition is identified, the electrosurgical generator can be instructed to adjust the gradual voltage ramp of the RF energy to instead maintain a current voltage value (i.e. hold constant) (77). However, if the measured phase and current has not reached or crossed the predetermined threshold value, the electrosurgical generator can then be instructed to wait a predefined time period while continuing to supply the RF energy in the gradual ramping fashion (in 75) all while still monitoring for the hold condition (in 76).

Once the electrosurgical generator is instructed to hold the RF energy constant (in 77), the electrosurgical system can be configured to monitor for and identify when an end condition (78) has been satisfied. When the end condition is detected, the electrosurgical system will determine that the sealing cycle has been completed to the current tissue being sealed. For example, some end conditions may correspond to a pre-determined period of time that lapses after the hold condition (in 77) has been detected by the electrosurgical system. Other end conditions may be met when one or more parameters (e.g. current, power, voltage, phase) are measured by the electrosurgical system as reaching, exceeding, or falling below pre-determined thresholds. In any case, once the end condition has been determined to have been satisfied by the electrosurgical system, the electrosurgical system can initiate termination procedures that will end the sealing process being performed on the tissue. The termination instructions carried out by the electrosurgical system may include terminating/stopping the supply of RF energy that was being generated by the electrosurgical generator to the tissue (79).

It may be possible, prior to the start of the sealing cycle (e.g., before 71), that the electrosurgical system can be configured to measure an impedance at the electrosurgical instrument to determine whether an electrical short or open circuit condition is detected. Such determination can be performed by the electrosurgical system using a low voltage measurement signal delivered from the electrosurgical generator to the connected electrosurgical instrument. The measured impedance can be used by the electrosurgical system to determine if the tissue grasped by the electrosurgical instrument is within the operating range (e.g., 2-2000) thereby indicating that a sufficient amount (e.g., volume) of the tissue is grasped. If this initial impedance check is passed, the electrosurgical generator can be instructed to begin supplying RF energy to the electrosurgical instrument. However, if the initial impedance check fails, the electrosurgical system can output an error signal and inform the user (e.g., surgeon). In this way, the user can be informed to re-adjust the electrosurgical instrument to grasp a larger amount (e.g., volume) of the tissue. Once the RF energy is being supplied to the electrosurgical instrument (71) from the electrosurgical generator, the impedance/resistance need not be measured again.

While the above generally describe the electrosurgical system and how the electrosurgical system can be implemented with the sealing process of tissue, there are various scenarios that may also need to be considered when using the electrosurgical system with tissues having different characteristics such as different types, thickness, and/or condition (e.g., double/repeat seal). The following sections of the disclosure will describe the details and processes that can be considered and implemented by the electrosurgical system to more accurately identify the type, thickness, and/or condition of the tissue being sealed. Based on the identification, the RF energy can be better adjusted by the electrosurgical system to perform the sealing process on different tissues.

One detail that the electrosurgical system may need to identify to properly carry out the sealing process is the thickness of the tissue being sealed. The thickness of the tissue can influence the amount of RF energy needed to perform the sealing process. Furthermore, the thickness of tissue can also influence other parameters (e.g., voltage profile, current) of the RF energy being applied to the tissue. In an example, thick tissue (such as muscle and fat) tend to draw less current than thinner tissue (such as mesocolon or mesentery). Therefore, the sealing cycle for thicker tissue may tend to take longer to complete than thinner tissue. Furthermore, the amount of RF energy during the sealing cycle needed by the thicker tissue may also be greater than thinner tissue as there may be more fluid/water to vaporize in the former thicker tissue. Therefore, providing a way for the electrosurgical system to identify the tissue thickness early in the sealing process can allow for better configuration of the electrosurgical system such that an optimal amount of RF energy can be used to carry out the sealing process.

Figure 6:
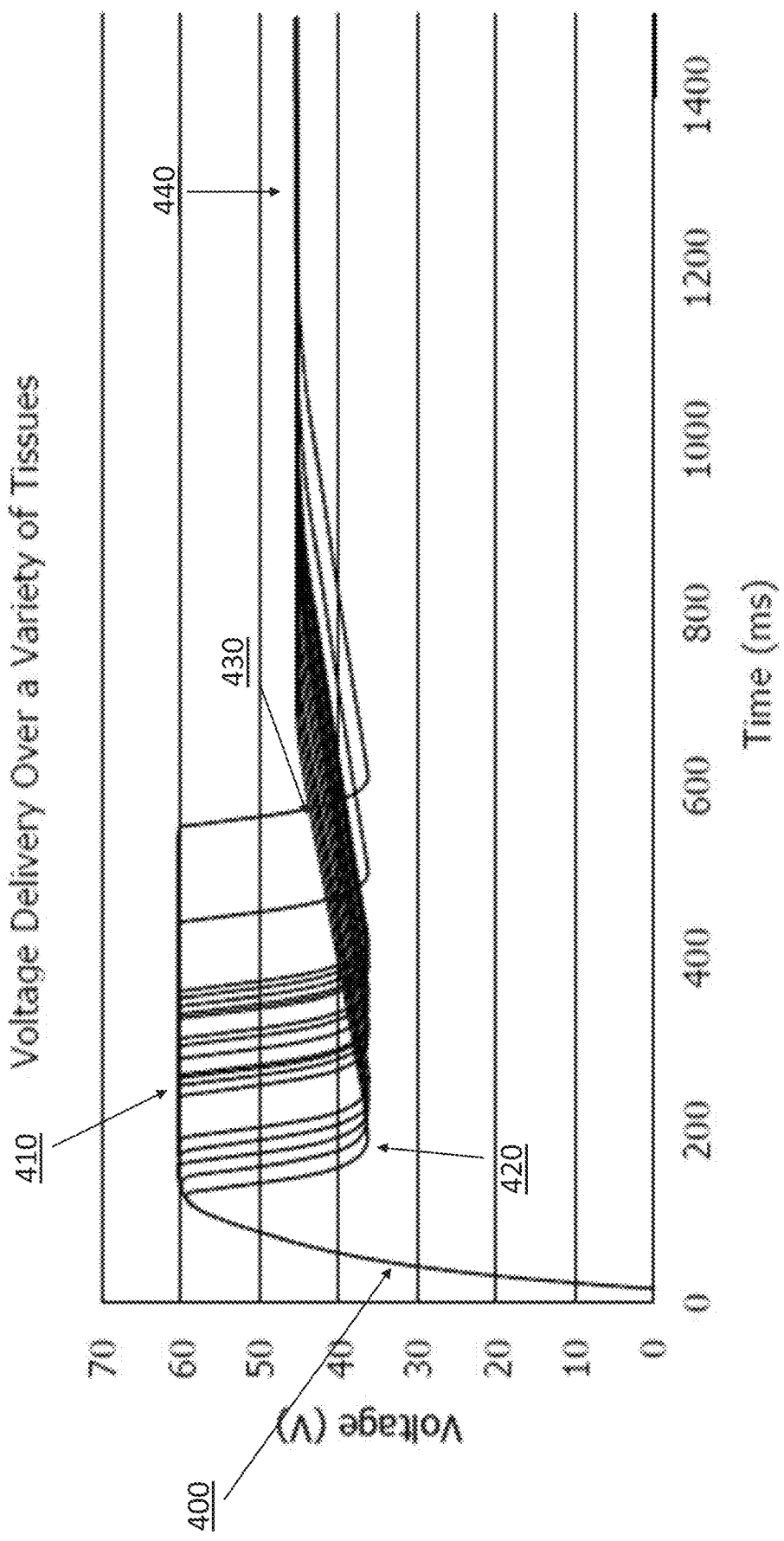
FIG. 6 to FIG. 9 are graphical representations of sample data pertaining to a sealing process or aspects thereof in connection with the electrosurgical system in accordance with various embodiments of the present invention.
Figure 7:
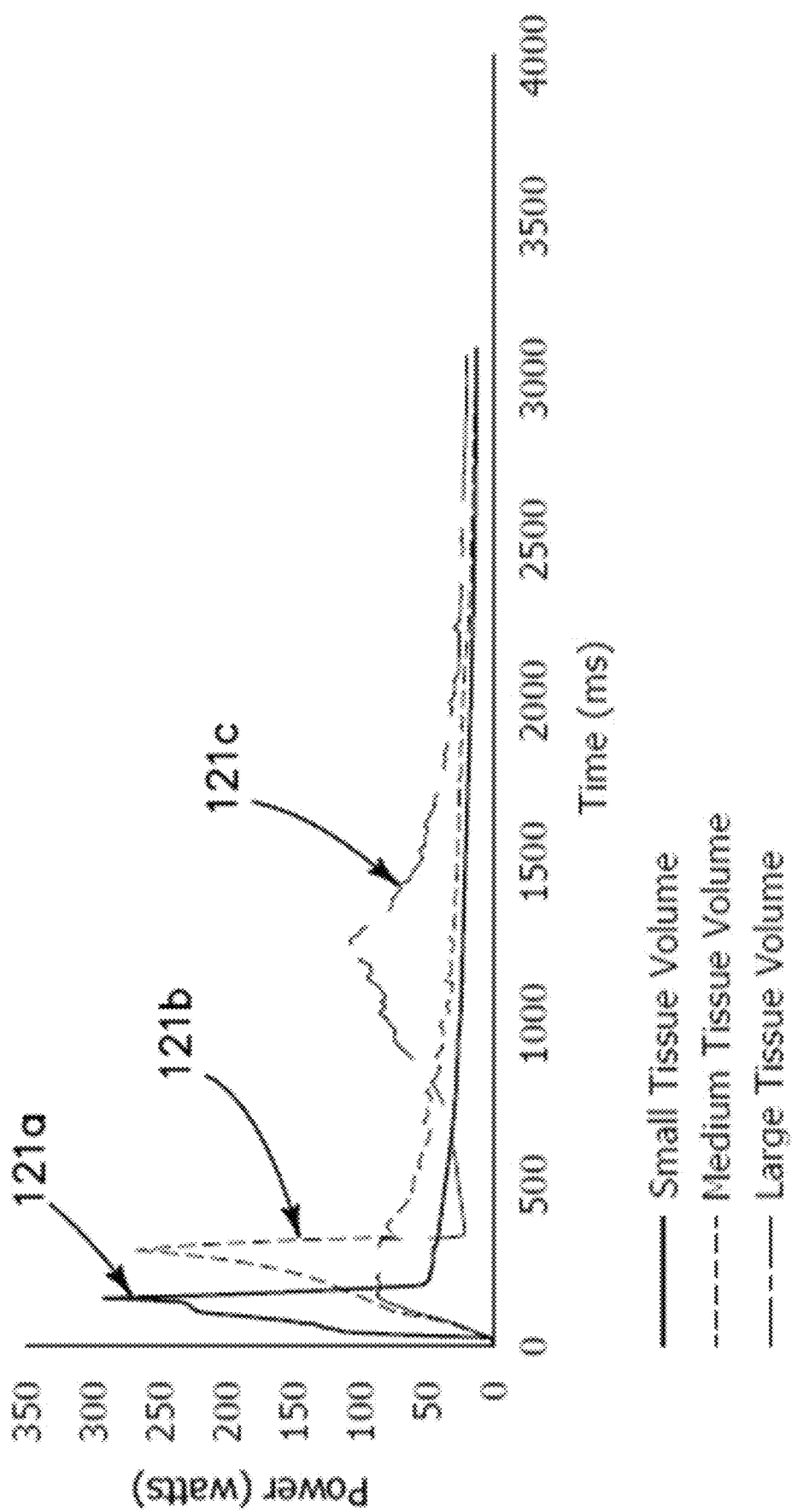

FIG. 6 and FIG. 7 are graphical representations of sample experimental data pertaining to a sealing process or aspects thereof in connection with the electrosurgical system in accordance with various embodiments of the present invention. Specifically, the sample experimental data illustrates various voltage profiles for the RF energy being applied to tissue having different thicknesses.

In each example, the electrosurgical system (e.g., electrosurgical generator) supplies RF energy that will be used to seal or fuse tissue (of varying thicknesses) via the electrosurgical instrument. The electrosurgical system is configured to control/modify the RF energy being supplied by the electrosurgical generator to the electrosurgical instrument. On one hand, the electrosurgical system needs to provide enough RF energy to the electrosurgical instrument so the electrosurgical instrument can properly heat the tissue to vaporize the fluid/water in the tissue and subsequently maintain the appropriate temperature adequate to complete the seal. However, the electrosurgical system also needs to ensure that the tissue is not exposed to excess amounts of RF energy to minimize or prevent damage to the tissue undergoing the sealing process.

FIG. 6 illustrates example voltage profiles associated with the RF energy being used by the electrosurgical system to heat the tissue to the appropriate temperatures used to seal different tissue thicknesses. Each voltage profile represents the voltage associated with the RF energy being applied to tissues of varying thicknesses by the electrosurgical system.

The electrosurgical system implement a similar/same initial stage of the RF energy having a quickly increasing voltage (400) for a seal cycle regardless of the type of tissue being sealed. The quickly increasing voltage (400) corresponds to the RF energy having a voltage that increases over a minimal time period thereby resulting in a steep voltage slope (or rate of change). A measured maximum voltage level (410) can be used to identify when the tissue being sealed is heated to a sufficient temperature for initiating desiccation (e.g., fluid/water vaporization in the tissue). The aim of the initial stage of the seal cycle (associated with the steep voltage ramp) is to have the tissue heated to the temperature that corresponds to when desiccation can occur as quickly as possible. In some embodiments, the electrosurgical system implementing the initial voltage ramp (also referred to as voltage pulse) may customize the duration. For example, the electrosurgical system may have the duration of the initial voltage ramp be based on the type of tissue in contact with the electrosurgical instrument, rather than be or based on a static, fixed, or predefined value.

By identifying how long the maximum voltage level (410) will be applied to the tissue, the electrosurgical system can tailor the subsequent voltage profile (420, 430, 440) accordingly based on the tissue (e.g., thickness) being sealed to ensure that the vaporization for the tissue can continue at a controlled rate. Failure by the electrosurgical system to identify when vaporization begins can result in longer seal cycles as well as weaker burst pressures, more thermal spread and/or tissue adhesion because less than optimal amount of RF energy will be used. For example, if adjustments are made by the electrosurgical system to the voltage profile of the RF energy (corresponding to 420-440) too early before vaporization actually begins, the tissue may not have been heated to a temperature that would be appropriate to remove fluid/water from the tissue. Subsequent applications of RF energy will still be used for heating the tissue rather than being used mainly for removing fluid/water thereby resulting in some fluid/water that would remain in the tissue when the sealing cycle is terminated (e.g., timing condition). On the other hand, if adjustments by the electrosurgical system are made to the voltage profile of the RF energy (corresponding to 420-440) too late after vaporization begins, the tissue may be exposed to still increasing or high amounts of RF energy. The overexposure of RF energy to the tissue may overheat and damage the tissue thereby negatively impacting the tissue and the seal quality.

As illustrated in the figure, the application of the maximum voltage for the RF energy can vary in duration based on thickness of the tissue. Thinner tissues may reach the vaporization point faster than thicker tissue (e.g., thinner tissue may have less to heat up as well as less fluid/water to remove) thereby requiring a lesser duration of the maximum voltage. By comparing tissues that reach the same/similar vaporization point at the same time, the electrosurgical system can determine that these tissues have similar thicknesses.

Alternatively, identifying tissue having similar thicknesses can also be determined by the electrosurgical system based on calculating a ratio that compares a total time it takes the tissue to reach a temperature where vaporization begins and a measured current value at that point in time. Accordingly, thinner tissues will have a lower ratio value while thicker tissue will have a higher ratio value. These ratios can be stored in memory (e.g., template) so that the electrosurgical system can, for example, provide the appropriate voltage profile for the RF energy to the tissue being sealed based on what was provided to past tissue having a similar ratio.

In an embodiment, the electrosurgical system can store (within the memory module or any other data storage device) instructions identifying how the RF energy may need to be identified based on different characteristics associated with the tissue being sealed. For example, tissue having a first thickness may need to be provided a particular voltage profile while a different tissue having a second different thickness may need to be provided a different voltage profile. The relationships between different tissue types, thickness, and/or conditions (e.g., repeat seals) and corresponding instructions that the electrosurgical system can execute (e.g., alter/modify RF energy, terminate RF energy) can be stored as a template and utilized by the electrosurgical system as needed. The template can be customized and updated by any number of different entities such as the manufacturer (of the electrosurgical generator and/or the electrosurgical instrument), the user (e.g., surgeon), or some other party (e.g., administrator). The template for the electrosurgical system can be downloaded on a separate computing device, transferred to the electrosurgical system via, for example, external memory device (USB), and stored in the memory module.

In some cases, the template can be stored in the electrosurgical instrument (e.g., via a memory module). Different electrosurgical instruments may interact with tissue and/or operate differently from other electrosurgical instruments (e.g., electrode size and electrode contact relative to the tissue). Therefore, data (e.g., operational instructions, templates) that can be used by the electrosurgical system to specially configure the operation of the electrosurgical system to be compatible with the specific electrosurgical instrument may also be useful. When the electrosurgical instrument is connected to the electrosurgical generator, the template associated with the electrosurgical instrument can then be provided and stored at the electrosurgical generator for use immediately as well as in subsequent future operations.

Other possible reasons for the difference in the implementation of the maximum voltage may also be based on the type of tissue undergoing sealing and/or the amount (i.e., volume) of tissue grasped by the electrosurgical instrument being sealed. As with thickness, other templates can also be provided to the electrosurgical system that categorizes other types of tissues (e.g., fat, muscle) so that electrosurgical system can utilize in providing the appropriate RF energy once the type of tissue has been identified.

With the electrosurgical system aiming to obtain the RF output peak condition for each of the different types of tissue being sealed, the amount of time the electrosurgical system (or specifically the electrosurgical generator) can then supply the RF energy can be made to vary. For example, as illustrated in FIG. 7, the RF output peak conditions occur at different times with tissue of different volumes. Other factors that could influence the timing of when the RF output peak condition occurs also can include thickness of the tissue and/or whether the tissue has undergone the sealing process in the past.

Generally, RF output peak condition occurs later in the seal cycle for thicker tissue because thicker tissues take longer to heat up compared to thinner tissue. As an example, FIG. 7 illustrates that the RF output peak condition for small tissue volume can occur around 250 ms (121*a*). Meanwhile, the same figure shows that the RF output peak condition for large tissue volume could occur as late as 1250 ms (121*c*) into a seal cycle. As noted above, the RF output peak condition corresponds to the point in time where enough RF energy has been provided to the tissue to heat the tissue to a temperature when vaporization of the fluid/water in the tissue begins. Accordingly, the height of the peak at the RF output peak condition can be determined based on a surface area of the tissue undergoing sealing because tissues with larger surface areas having higher peak values corresponding to having more "stuff" being or acting as electrically parallel resistance with respect to the electrosurgical instrument.

Independent of the volume and/or thickness of the tissue undergoing the seal cycle, the amount of time for sealing the tissue can be limited to a pre-determined maximum time threshold or limit. The pre-determined maximum time threshold or limit can be established as a means of minimizing or preventing situations where a user (e.g., surgeon) may apply RF energy to tissue for longer than necessary. The downside of setting the pre-determined maximum time threshold (e.g., static time period) without actually reaching the RF output peak condition could lead to scenarios where either the electrosurgical system applies RF energy longer than necessary (e.g., for small tissue volumes) or where the electrosurgical system does not apply enough RF energy (e.g., for large tissue volumes). Therefore, a dynamic voltage ramp can be implemented by the electrosurgical system to balance performance on each end (e.g., applying RF energy for too long and not applying RF energy long enough) by allowing for a close-to-ideal or optimal RF energy dosage. By having the electrosurgical system configured to rapidly achieve the RF output peak condition, the electrosurgical system can optimize overall sealing of tissue and reduce the time to seal the tissue without losing or reducing tissue integrity.

As described above, the electrosurgical system is configured to provide an initial high voltage ramp or pulse to bring the tissue to the RF output peak point quickly (as the RF output peak condition represents or corresponds to a water vaporization point or condition). The water vaporization point or condition occurs when the tissue temperature is highest and immediately prior to water vaporization occurring in the tissue. In an example sealing process, the electrosurgical system can instruct the electrosurgical generator to modify the voltage of the RF energy to be high (e.g., 40% or greater than a pre-determined maximum) with a quickly increasing rate of change (e.g., at a rate 10 volts per millisecond). The increase in voltage of the RF energy is performed to provide the dynamic voltage ramp or pulse used to achieve the RF output peak condition quickly.

The RF output peak condition can be observed visually by the user (e.g., surgeon) when steam starts being generated from the tissue being sealed. However, such visual observation can be unreliable. For example, if the RF output peak condition is not properly identified prior to moving on the seal cycle, the tissue can become under-pulsed. Specifically, if the vaporization or peak point is not reached during the initial voltage ramp or pulse (e.g., under-pulsing), then the subsequent drop in voltage and gradual ramp-up can slow down the vaporization of the fluid/water in the tissue as the seal cycle progresses. Tissue that is under-pulsed starts its effective seal cycle (e.g., removal of water) much later than anticipated thereby resulting in less total water being removed in the same time period. Therefore, properly and accurately identifying when the RF output peak condition occurs (e.g., desiccation begins) in tissue can be important.

By using a dynamic ramp methodology, the electrosurgical system can ensure that tissue (regardless of volume) can be brought to its optimal RF output peak condition point quickly before progressing further into the seal cycle. In doing so, the likelihood of under-pulsing (or not providing sufficient RF energy to have the tissue reach the RF output peak condition) is dramatically reduced. Furthermore, by reducing the likelihood of under-pulsing, the average RF delivery after the dynamic voltage ramp or pulse can be shortened in time or lowered in power without affecting seal quality. That is because once the RF output peak condition can be established, the focus or attention of the electrosurgical system can be directed to removing fluid/water from the tissue efficiently, rather than variability associated with heating tissue.

Determining by the electrosurgical system regarding when the RF output peak condition occurs can be difficult, particularly in real-time. A variety of factors (such as noise or similar fluctuations, imprecision in measurement of the RF energy output) may obscure or delay the determination of the RF output peak condition by the electrosurgical system. In some embodiments, the electrosurgical system can implement smoothing or filtering such imprecisions, which can assist in enhancing how the electrosurgical system can detect or determine the RF output peak condition. However, the delays associated with the electrosurgical system implementing filter processing and the like can delay the real-time determination of the RF output peak condition. One downside of delaying the real-time determination of the RF output peak condition is that the electrosurgical system could over-pulse (i.e., provide too much RF energy) the tissue.

To avoid or reduce the delay or a potential over-pulsing of the tissue, the electrosurgical system can utilize one or more state-based thresholds. The state-based thresholds can be used to identify different conditions or states during the sealing process based on a predicted maximum current value corresponding to the RF output peak condition. In an embodiment, the state-based thresholds can be a percentage of the predicted maximum measured current (e.g., 80% of the predicted maximum current value or window). In other embodiments, the state-based thresholds can be static offsets (e.g., 400 mA or 30 W below or within a predicted maximum value or window). In some embodiments, the state-based thresholds can incorporate a combination of both a percentage and a static offset based on the predicted measured maximum current.

In various embodiments, the state-based thresholds can be based on various parameters associated with the outputted RF energy such as current, voltage, power. However, for the purposes of this application, embodiments described herein will utilize current as the parameter (although the other parameters are also possible). The electrosurgical system will monitor the parameters associated with the outputted RF energy to detect when one or more of the state-based thresholds have been reached or crossed. By using the state-based thresholds, the electrosurgical system can determine when to move onto the next step/stage of the sealing process for the tissue.

In an example, state-based thresholds can be used to monitor when the vaporization of the fluid/water (i.e. desiccation) occurs in tissue. In one embodiment, once the maximum current value has been obtained, the electrosurgical system can calculate a percentage-based state-based threshold (e.g., 80%) using the maximum measured current that corresponds to when desiccation started. The state-based threshold used by the electrosurgical system can also be based on past collected data and correlation between the maximum measured current value and the maximum current value when desiccation generally occurs for other similar tissue. When the electrosurgical system detects that the measured current reaches and/or crossed the percentage-based state-based threshold, the electrosurgical system can make a determination regarding whether desiccation has occurred in the tissue. In this way, the electrosurgical system may determine not to move onto the next step of the sealing process (e.g., adjust the voltage level of the outputted RF energy) until this percentage-based state-based threshold has been reached. The electrosurgical system can use the state-based thresholds to ensure that desiccation has occurred by monitoring and detecting whether the measured parameter (e.g., current) reached or crossed the state-based threshold before the next step in the sealing process is performed (e.g., voltage is adjusted).

Accordingly, the lower (or greater offset) the state-based threshold is based on the maximum measured value, the longer the quickly increasing voltage of the RF energy output may need to be applied to the tissue. However, the increase duration of implementing the increasing voltage by the electrosurgical system may result in the possibility of over-pulsing the tissue. Accordingly, the electrosurgical system may be less likely to prematurely halt or drop the voltage of the RF output before desiccation has actually occurred (e.g., under-pulse) due to external factors such as noise.

The above describes an embodiment where a state-based threshold (based on maximum measured current value) is used to identify one of the steps/stages of the sealing process (e.g., the start of desiccation in the tissue). Other state-based thresholds can also be used to identify other steps/stages in the sealing process (e.g., when the output of RF energy should be terminated).

In various embodiments, the electrosurgical system may record or store a predicted maximum value (e.g., voltage, current) for use in calculating the state-based thresholds. However, to ensure that the recorded/stored value is an actual maximum value, the electrosurgical system can continue to monitor for subsequent measurements that exceed the stored predicted maximum value. In various embodiments, the electrosurgical system monitors or records parameters associated with the outputted RF energy at set intervals (e.g., every 50 ms) for a pre-determined period of time. During this time period, the electrosurgical system compares the recently monitored parameter against the stored maximum value to determine if a new maximum has occurred. When this occurs, the current monitored value is stored as the "new" maximum value. If no new maximum value is detected once the pre-determined period of time expired, the previous recorded maximum value is used.

As described above, the electrosurgical system can use the state-based thresholds to define when different steps/stages for the sealing process can occur. For example, the sealing process can be characterized by a series of different steps/stages with exit conditions (e.g., thresholds). As RF energy is applied and the value of interest changes (e.g., power, voltage, and/or current increases), the series of different steps or states are progressed through or cascaded. By increasing the number of states, the resolution of the cascade increases. However, depending on the resolution of the cascade, some accuracy can also be lost in determining the RF output peak condition. By using a cascade or similar progression of states or stages, the computational resources required from the electrosurgical system may be less intensive. Furthermore, the electrosurgical system may not require (or at least minimize) the use of the stored variables (e.g., measured maximum value) which also provides a way to reduce the computational resources required by the electrosurgical system in determining and managing the RF energy being applied to the tissue.

In accordance with various embodiments described herein, the electrosurgical system can utilize the state-based threshold (associated with a parameter such as voltage or current) that is calculated from a predicted or measured maximum value by multiplying the predicted value by a percentage (e.g., 80%). Higher predicted maximums may require a larger drop in the interested value (e.g., current or power) to trigger or to identify specific events (e.g., when desiccation has occurred). In some embodiments, the state-based threshold can be calculated by introducing a static offset value (e.g., −0.5V, 30 W, 400 mA). Depending on the predicted or measured maximum value, the static offsets can result in smaller or larger values than a percentage calculation. In any case, static offsets can be useful when the amplitude of noise or similar imprecision in the electrosurgical system are known because static offsets can be set to account for the specific imprecision (e.g., set higher than the amplitude of the noise). In various embodiments, the electrosurgical system utilizes a combination of both the static offset and percentage calculation acting in parallel, serially, and/or varying the order to enhance the identification or determination of the RF output peak condition and/or for calculation of state-based thresholds. Such combination of both static offsets and percentages may be useful in different situations to account for known imprecisions or when the predicted or measured maximum value reaches a specific threshold where a larger drop in the interested value to trigger a state-based threshold is not desired.

As the electrosurgical system monitors a rate of change of the interested value (e.g., current, voltage, and/or power), the electrosurgical system can then anticipate and detect the occurrence of the RF output peak condition. In addition, the electrosurgical system can also monitor and calculate the derivative or rate of change associated with the interested value. The derivative calculation is useful to identify whether the RF output peak condition is associated with a true peak or if the true peak is near or close to occurring subsequent a current detected peak (especially in situations where there are multiple peaks). As referred to herein, a true peak corresponds to the absolute maximum measured value for a parameter (e.g., current) obtained by the electrosurgical system during the sealing process—specifically during the initial voltage ramp. The true peak corresponds to the point during the seal cycle whereby the entirety of the tissue (especially in situations where the tissue being sealed has sections of varying thicknesses) is heated to a temperature sufficient to begin desiccation.

In various embodiments, the electrosurgical system is configured to adjust/modify parameters (e.g., current, voltage) of the RF output to determine whether a detected peak corresponds to the RF output peak condition. For example, the electrosurgical system (via instructions to the electrosurgical generator and/or RF amplifier) can gradually ramp up a parameter (e.g., current) associated with the RF energy being applied to tissue being sealed. The electrosurgical system can also place the electrosurgical generator into a state of current regulation. When a current regulation value exceeds the ability of the tissue being sealed in taking more current, the electrosurgical system may no longer be current regulated thereby resulting in a sharp increase in voltage as the electrosurgical system switches regulation. The sharp increase in voltage described above can be used as an indication or determination of the RF output peak condition. As such, the electrosurgical system can use this method or mechanism as another way to obtain a predicted maximum value based on a parameter of interest (e.g., current, voltage) that would correspond to the RF output peak condition.

In various embodiments, if an error or an unexpected result occurs, the electrosurgical system can terminate steps associated with the sealing process being performed (e.g., supplying RF energy to the tissue being sealed). In various embodiments, example errors detected by the electrosurgical system may include detection of an electrical short or an open circuit.

A detected electrical short circuit error can be determined by the electrosurgical generator when a measured phase angle of the supplied RF energy by the electrosurgical generator equals or exceeds a predetermined phase value (e.g., sixty degrees). A detected open circuit error can be determined by the electrosurgical generator when a measured current of the supplied RF energy equals or is below a predetermined value (e.g., 100 milliamps) and/or a measured voltage of the supplied RF energy equals or exceeds a predetermined value (e.g., 50 volts). The predetermined values for detecting the electrical short circuit and/or open circuit error can be customized based on various factors (e.g., type of electrosurgical device, area of the jaw).

If the electrosurgical system did not detect any error conditions during the sealing process, this can be used as an indication that the tissue was successfully sealed. A successful tissue seal, in accordance with various embodiments, is recognized as the tissue seal being able to withstand a predetermined range of burst pressures or a specific threshold pressure.

Returning back to the discussion regarding the sealing process, tissue seal formation may be dependent on denaturization and cross linkage of the native collagen present in vasculature extra cellular matrix (which may start at about 60° C.) of the tissue being sealed. Furthermore, the strength of the vasculature extra cellular matrix may be dependent on desiccation of the seal site (i.e., portion of the tissue undergoing the sealing process). As referred to herein, vaporization or removal of fluid/water present in the tissue undergoing sealing can also be referred to as desiccation. At temperatures of at least 80° C., the bonds between the denatured collagen and other living tissues can be created. However, collagen degrades in response to being exposed to elevated temperatures for an extended period of time rather than being exposed for a short period of time but having a peak temperature. As such, exposing tissue to high temperature conditions (e.g., 100° C.), for a short duration corresponding to a short seal cycle does not impact the structure of the collagen but still allows for vaporization of water/fluids within the tissue.

The total time needed to properly seal tissue may be based on how high and how fast the tissue is heated. In particular, the tissue may be exposed to high temperatures (e.g., 100° C.) in order to vaporize water/fluids within the tissue quickly so that the denatured collagen crosslinks and bonds to other living tissues. Furthermore, the quick vaporization of water/fluids is provided to limit situations where collagen-water hydrogen bonding can occur. To optimize seal time, an embodiment may aim to expose tissue to a temperature of 100° C. as quickly as possible in order to begin the desiccation process as soon as possible.

Referring back to FIG. 6, once the dynamic voltage ramp 400 has been completed (i.e., the RF output peak condition 410 has been detected), the electrosurgical system reduces the voltage to a predetermined voltage level 420 and gradually ramps up the voltage of the supplied RF energy 430. The RF output peak condition 410 generally corresponds to a point in time where the vaporization of fluid/water in tissue begins. While the gradual voltage ramp 430 is occurring, the electrosurgical system is ensuring that enough RF energy is still being applied to the tissue to maintain a temperature sufficient for desiccation of the tissue. The gradual voltage ramp 430 allows for continuous fluid/water vaporization at a rate that does not cause seal structural failures or damage to the tissue (e.g., if too much heat is applied to the tissue) while still enhancing vessel sealing performance.

Applications of high voltage levels to tissue may cause the affected tissue undergoing the sealing process to adhere to the active electrodes on the jaws of the electrosurgical instrument. As such, termination of the gradual voltage ramp at a lower peak voltage and holding that voltage output constant 440 at the end allows for continued RF energy application for desiccation while reducing the possible occurrence of tissue adherence to the jaws/electrode of the electrosurgical instrument associated with applying too much voltage across the tissue. Determination by the electrosurgical system as to when to terminate the gradual voltage ramp may be conducted by monitoring various parameters associated with the RF energy being supplied (e.g., current, voltage, phase). For example, as tissue desiccates, the phase associated with the tissue may become more capacitive thereby drawing less current. By terminating the gradual voltage ramp at a fixed current value as the current falls and when the phase is capacitive, the desiccation level of the tissue can be categorized (i.e. a determination how much fluids/water has been removed from the tissue can be estimated). This allows for the electrosurgical system to better configure the seal cycle being carried out in order to provide the appropriate amount of RF energy based on, for example, electrical and structural differences in tissues being sealed. In other words, the electrosurgical system is capable of customizing how the seal cycle is performed for different types of tissues.

Figure 8:
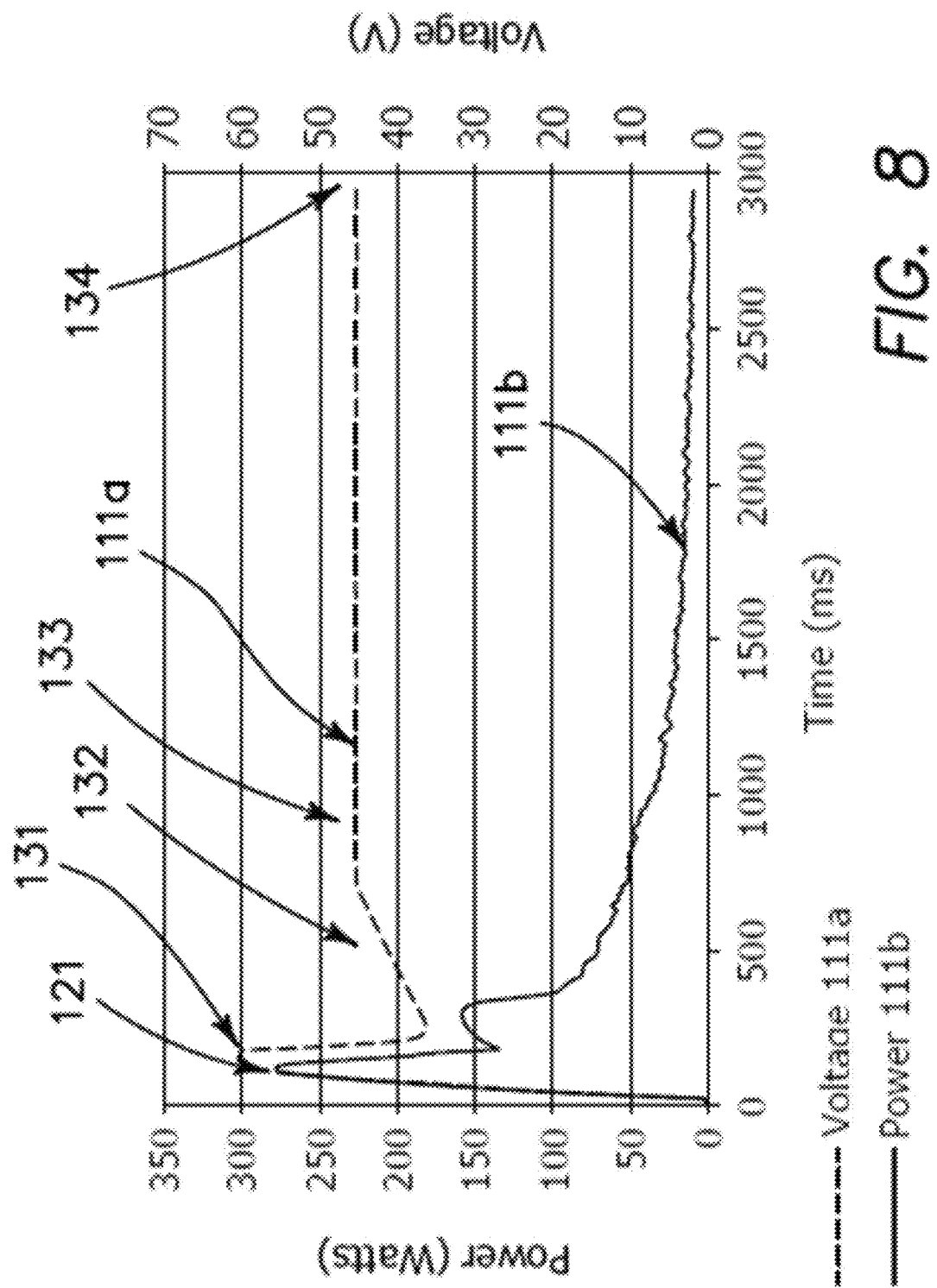
Figure 9:
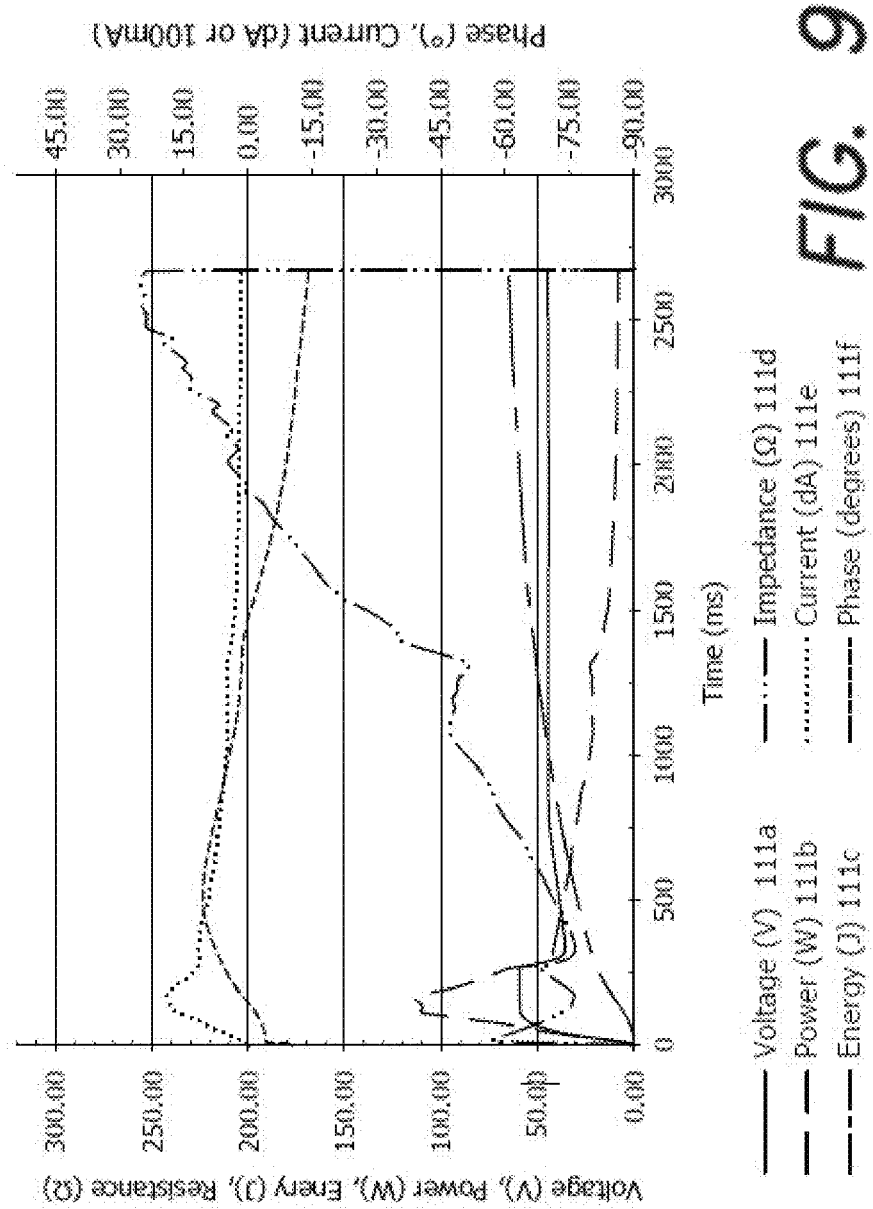

In various embodiments, state-based thresholds (e.g., percentage and/or static) based on the stored measured maximum value can also be used to identify when the gradual voltage ramp can be stopped, how long the RF energy should be held constant, and when the RF energy should be terminated. In order to achieve the appropriate tissue effect, the phase angle, current and/or power of the applied RF energy can be measured, calculated and/or monitored by the electrosurgical system. FIG. 8 and FIG. 9 are additional graphical representations of an exemplary seal cycle. As illustrated in the figures, voltage 111*a* is shown relative to other RF output readings or indicators that can be monitored by the electrosurgical system such as power 111*b*, impedance 111*c*, energy 111*d*, current 111*f* and phase 111*g*. In some embodiments, the electrosurgical generator may be configured to limit what indicators or readings can be measured or calculated to reduce operational costs, power costs, consumptions and/or the number of parts (e.g., sensors) of the electrosurgical generator. The embodiments illustrated in FIG. 8 and FIG. 9 are provided as an example for contextual purposes. In other embodiments, the electrosurgical generator may also be configured to limit what indicators or readings should be measured or calculated based on accuracy and practicality (i.e. measurements that are not practical or not accurate will not be taken). For example, instead of voltage, other parameters such as current, power, and/or phase may be used.

As illustrated in FIGS. 8 and 9, the voltage of the RF energy output 111*a* is increased for an initial period of time associated with the seal cycle. This initial period of time is short compared to the total seal time of the tissue. During this initial period of time, the electrosurgical system is implementing the initial dynamic voltage ramp or pulse for the RF energy 131 that will be used to bring the temperature of the tissue to the point where desiccation begins (i.e. the RF output peak condition).

In an embodiment, the electrosurgical system determine when the RF output peak condition 121 is detected/reached. Once the RF output peak condition is detected (corresponding to the beginning of desiccation), the voltage of the RF energy is reduced and gradually ramped up relative to the initial voltage pulse performed during the initial period of time. The slow (or gradual) voltage ramp 132 by the electrosurgical system seeks to maintain the temperature of the tissue between the jaws close to 100° C. to control the boiling rate/vaporization of water/fluid in the tissue.

As the tissue undergoes desiccation, the electrosurgical system can monitor any number of different parameters of the RF energy (e.g., voltage, phase angle, current, and power) to determine when the voltage of the RF energy can then be held constant 133 (i.e., termination of the gradual voltage ramp 132). By recognizing the appropriate amount of RF energy to apply to the tissue for desiccation, the electrosurgical system can ensure that no more RF energy is applied to the tissue than what is needed to vaporize the water/fluids in the tissue. A benefit to controlling the amount of RF energy being applied to tissue in this manner is that there is a reduction in the possible tissue adherence between the tissue being sealed and the electrode/jaw of the electrosurgical instrument (which occurs when tissue is heated for longer than necessary).

Once the electrosurgical system detects that a seal cycle has been completed (whether the detection is based on waiting for a pre-determined time period or identifying that the corresponding state-based thresholds has been reached/crossed), the electrosurgical system can then terminate the RF energy supply being provided to the electrosurgical instrument used to seal the tissue. The termination of the RF energy supply generally refers to halting, disrupting, or stopping the supply of RF energy generated by the electrosurgical generator 134. In some embodiments, the electrosurgical system may automatically terminate the supply of the RF energy to the tissue after waiting a pre-defined period of time after the end of the previous gradual voltage ramp of RF energy 132.

To detect possible errors, the electrosurgical system can be configured to identify unintended current draw. As an example, some tissues may appear to draw the maximum current or power that can be supplied by the electrosurgical generator. While the electrosurgical system is under such a current condition, the supply of RF energy required to seal the tissue 1) may not be sufficient or 2) may not be efficiently supplied by the electrosurgical system. To handle such a condition, the electrosurgical system may be configured to determine if the current of the RF energy output is greater than a pre-determined threshold (e.g., 90% of the allowable maximum current or 4500 mA). If the detected current is equal or greater than the pre-determined threshold, the electrosurgical system may pause or incorporate a delay to ensure that the detected current has sufficiently dropped indicating that sufficient desiccation of the tissue has occurred. If, after the implemented pause or delay, the current has not sufficiently dropped, the electrosurgical system may raise an error and/or halt supplying the RF energy to the tissue. However, if the electrosurgical system detects that the current has sufficiently dropped below the pre-determined threshold (e.g., 4100 mA), a determination can be made by the electrosurgical system that the current condition has ceased and/or the tissue has reached the RF output peak condition (e.g., achieved a point where vaporization has begun).

Figure 10:
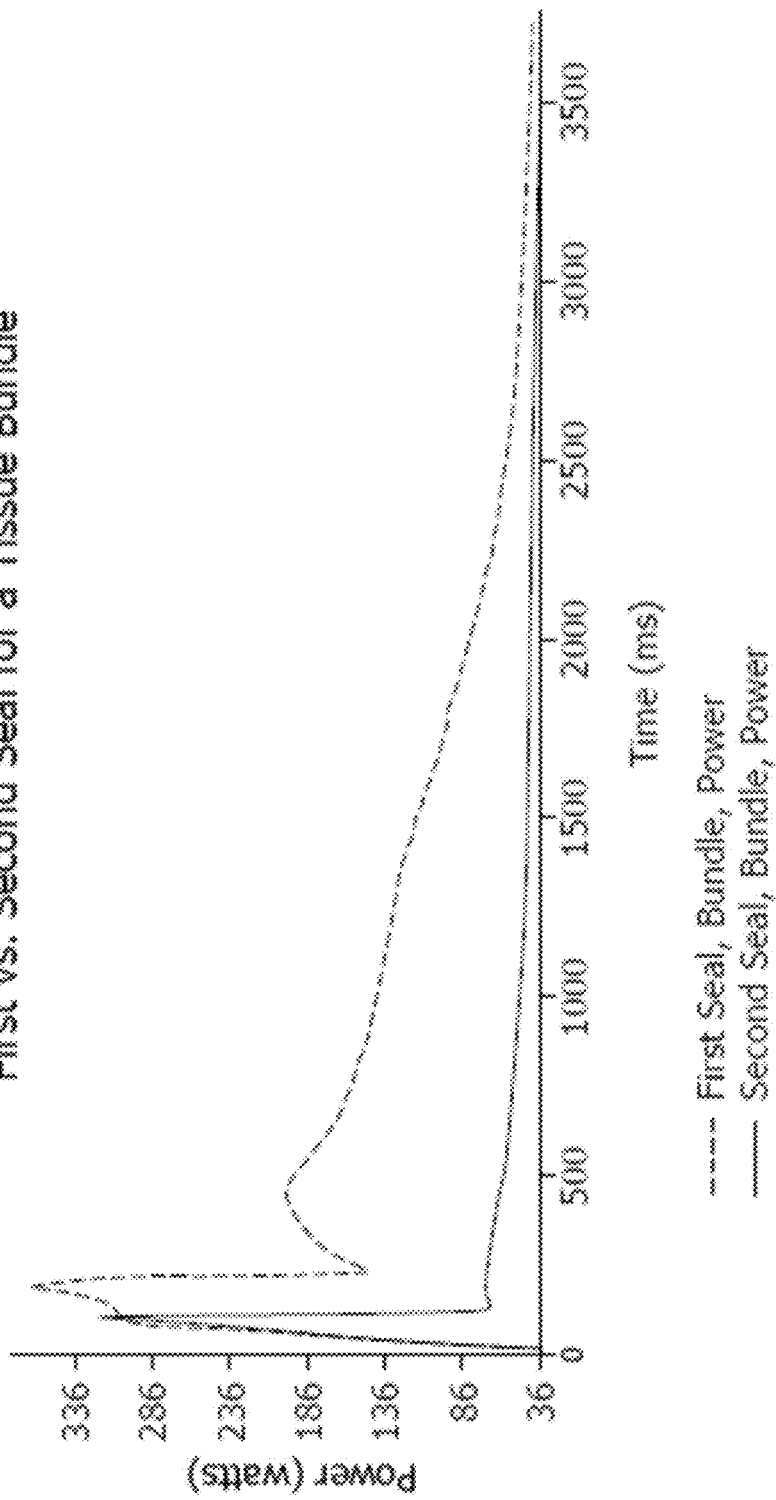
FIG. 10 is a graphical representation of sample data for a sealing process or aspects thereof with an electrosurgical system in accordance with various embodiments of the present invention.

FIG. 10 illustrates a graphical representation of samples of experimental data for a sealing process or aspects thereof with an electrosurgical system. After the initial dynamic voltage ramp, there may be situations where the tissue being sealed is found to draw a relatively low amount of current or power, is small in volume, or may be already highly desiccated. In the case of highly desiccated tissue, such tissues can be commonly encountered in a double or repeated seal situation (e.g., when a surgeon activates the instrument to supply RF energy a second time after a first seal cycle or an already completed seal cycle without moving the instrument or positioning the instrument on a different portions of the tissue or an entirely different tissue). The scenarios where the tissue has undergone double or repeated seals results in additional applications of RF energy to the tissue and thereby increases the possibility that some negative effects could occur such as potential eschar buildup, thermal spread, and/or adhesion associated with overheating the tissue. In various embodiments, the electrosurgical system is capable of reducing or preventing the output of RF energy having high voltage when such repeated seals are detected.

In some embodiments, the electrosurgical system is configured to identify or determine a desiccation level of tissue in contact with the electrosurgical instrument. Some ways the electrosurgical system detects the desiccation level involves the electrosurgical system employing low levels of current or power, employing high levels of impedance, employing low phase angles, employing low energy delivery, and/or detecting steam associated with water vaporization during the seal cycle. Once the desiccation level of the tissue has been identified, the electrosurgical system can modify the RF output accordingly, such as providing RF energy for a limited time period or modifying a voltage level if the tissue has been determined to be sufficiently desiccated. In various embodiments, static thresholds can be used for any of these values (e.g., current, power, impedance, phase angles) to trigger conditions (e.g., 500 mA). Alternatively, thresholds can also be based on percentage calculations based on a predicted maximum (e.g., 20% below a predicted maximum current).

In various embodiments, the electrosurgical system can also implement one or more of the state-based threshold values (associated with one or more of current, power, impedance, phase angles) to specifically distinguish situations where already-sealed tissue is present. The electrosurgical system can then be adapted to trigger early in the seal cycle and progress through to the later steps of the seal cycle. At the end of the seal cycle, first activations and subsequent activations can look very similar with the tissue being sufficiently desiccated in both cases. However, at the beginning of the seal cycle, first activations will draw much more current or power since water is still present in the tissue while subsequent seals will not draw as much current or power since the water has been previously removed (e.g., vaporized). In addition, as tissue undergo a first sealing cycle, the current or power drawn can change substantially. In contrast, subsequent activations on already-sealed tissue will have a much lower rate of change regarding current or power drawn.

In various embodiments, the electrosurgical system may be configured to track a phase of the RF output (e.g., at the beginning of a seal cycle) to identify/detect situations where the tissue has undergone repetitive seals and/or detect if the tissue is thin. For example, tissue that has undergone double seals tend to have phase values of greater than 20 degrees. Once a repeated seal or piece of thin tissue is identified, an alternate RF energy output (e.g., voltage profile) for sealing that tissue can be provided that is better adapted for that previously sealed or thin tissue.

In various embodiments, the electrosurgical system uses a cascade of phase values which adjusts the RF output depending on the magnitude of the initial phase. For example, if the measured phase is between 20 and 25 degrees, the electrosurgical system can apply a modest reduction of RF energy. However, if the phase is between 25 and 30 degrees, the electrosurgical system may be able to determine with more certainty the type or condition of the tissue in contact with the electrosurgical instrument and thus reduce further (or more aggressively) the RF energy. A detected phase angle over 30 degrees would have the electrosurgical system provide the largest or most aggressive reduction in RF energy. It should be noted that other parameters (e.g., current) could be monitored to identify/detect the type of tissue and/or state of the tissue as well as adjust the RF energy being applied to tissue.

Once highly desiccated or thin tissue has been identified, any change in RF output that results in less heat being applied results in a better sealing effect for the tissue. In contrast, additional RF energy or no reduction in RF energy on highly desiccated or thin tissues can result in various negative outcomes such as additional thermal spread, eschar, adhesion, and/or a longer procedure time without providing further benefits to hemostasis.

Thus, in various embodiments, the electrosurgical system is configured to detect situations where double/repeat seals occur by using a threshold value or range of threshold values to detect repeat seal situations and/or to stop a voltage ramp. This method or mechanism may then provide a lower hold voltage through the sealing process, use a threshold value to terminate or halt RF output, and/or end the seal cycle earlier. In various embodiments, the electrosurgical system is also able to use a threshold value to immediately leave a state (e.g., current step in the sealing process) rather than reaching a timeout value (e.g., pre-determined period of time associated with the current step) that can reduce the total seal time for the tissue.

In various embodiments, the maximum current or power value can be static or predetermined. This maximum value can be stored in memory or provided/set through external inputs (e.g., user interface on the electrosurgical generator) to the electrosurgical system. In accordance with various embodiments, the maximum current or power value is determined by the electrosurgical system through the application of the RF energy and having the electrosurgical system monitor the current and/or power of the supplied RF energy to detect a peak condition associated with the monitored current or power. In various embodiments, the maximum current or power value represents a vaporization point (i.e., when desiccation starts) for the tissue in contact with the electrosurgical instrument. In various embodiments, the electrosurgical generator provides a steep ramping voltage profile in order to bring the temperature of the tissue to a water vaporization point quickly.

In accordance with various embodiments, a maximum phase value is determined by the electrosurgical system through the application of the RF energy and monitoring the phase to determine a peak condition associated with the monitored phase. In various embodiments, a temperature sensor or detection system (e.g., thermocouple) is provided with the electrosurgical instrument to monitor tissue temperature and potentially identify a rapid rise of temperature occurring until water vaporization begins. In some embodiments, the temperature sensor or detection system (e.g., thermocouple) can be embedded on the surface of a jaw associated with the electrosurgical instrument. Once the point of water vaporization beginning has been detected, the electrosurgical system can implement a state change that would stop the rise in temperature. As noted above, the point of water vaporization can correspond to an RF output peak condition.

In accordance with various embodiments, a minimum impedance can be determined by the electrosurgical system through the application of the RF energy and monitoring the tissue impedance to determine an impedance floor representing an RF output peak floor. As such, the thresholds for detecting different conditions associated with the sealing process by the electrosurgical system may appear inverted with a minimum value or window being determined rather than a maximum (as in the case with current, power, or phase described above).

In accordance with various embodiments, the electrosurgical generator can be configured to provide additional regulation of various parameters or functions related to the output of the RF energy (e.g., voltage, current, power and/or phase). The electrosurgical generator can also configure the operations engine to utilize the various parameters or functions to adjust the output of RF energy being provided to the electrosurgical instrument accordingly. In one exemplary embodiment, the control circuitry of the electrosurgical generator provides additional regulation controls for direct regulation of phase in which voltage, current and/or power output would be adjusted to satisfy specified phase regulation set points provided by the operations engine.

In accordance with various embodiments, the electrosurgical generator also utilizes the monitored, measured and/or calculated values (e.g., voltage, power, current and/or phase) as control indicators in order to recognize a current state of the tissue and identify what needs to be executed next for the sealing process (e.g., adjusting the amount of RF energy being applied to the tissue). In various embodiments, additional measurements or calculations based on the measured values related to RF output regulation circuitry are provided via a script or an operations engine that can be used to recognize and act upon additional or different events related to or triggered by the additional measurements or calculations. The additional measurements described above may include error signals in combination with a pulse width modulation (PWM) duty cycle that is used to regulate various RF energy output parameters (e.g., voltage, current and/or power). Different or additional events or indicators that could be identified and triggered in various embodiments could be used as transitions from one regulation control to another regulation control (e.g. changing from current regulation to power regulation).

In various embodiments, the electrosurgical generator can be configured to utilize many states, control points, feedback, or checks to identify a current parameter value (e.g., phase, current, or power) and whether the parameter value has a positive or negative trend. An error can be signaled if the electrosurgical generator does not identify an expected trend. The use of the multiple states, control points, feedback and checks increase or enhance the resolution associated with the electrosurgical generator in identifying an expected RF output trend over different types of tissue.

In various embodiments, the electrosurgical generator can also monitor the phase or current and/or rate of change associated with the phase or current to determine if there is an electrical open or short condition associated with the connected electrosurgical instrument. In one example, the electrosurgical generator identifies an electrical short condition of the connected electrosurgical instrument by monitoring the phase of the outputted RF energy. If the monitored phase is greater than a predefined maximum phase value, the electrosurgical generator can confirm that the electrical short condition is present. Similarly, the electrosurgical generator can also identify whether an electrical open condition is present in the connected electrosurgical instrument by monitoring the current of the outputted RF energy. If the monitored current is less than a predefined minimum current, the electrosurgical generator can confirm that an electrical open condition is present. For both scenarios, the detection of the short or open condition causes the electrosurgical generator to flag that an error is present. Furthermore, the electrosurgical generator can terminate/halt the RF energy being supplied to the connected electrosurgical instrument.

In various embodiments, the process associated with the electrosurgical system (as described throughout the application) may be loaded into a memory module embedded into a connector and, in one embodiment, is removably connected to a plug and/or cable connection associated with the electrosurgical instrument. In various embodiments, a device script or process is programmed onto an adapter PCBA contained within the device connector or hardwired into circuitry within the device connector or controller during manufacture/assembly. The script source file can be written in a custom text-based language and then compiled by a script compiler into a script database file that is only readable by the electrosurgical generator. The script file contains parameters specifically chosen to configure the electrosurgical generator to output a specific voltage (e.g., 100 v (RMS)), current (e.g., 5000 mA (RMS)), and/or power level (e.g., 300 VA). In various embodiments, a device key programmer device reads and then programs the script database file into the memory of the adapter PCBA.

As described throughout the application, the electrosurgical generator can be configured to supply RF energy to a connected electrosurgical instrument. The electrosurgical system ensures that the supplied RF energy from the electrosurgical generator does not exceed specified parameters via detection of faults or error conditions. In various embodiments, the electrosurgical instrument provides the commands or logic used to appropriately apply RF energy, for example, based on a surgical procedure and/or tissue type. The electrosurgical instrument may include memory having commands and parameters that dictate the operation of the electrosurgical instrument and/or electrosurgical generator. For example, in an embodiment, the electrosurgical generator can supply the RF energy but the connected electrosurgical instrument decides how much or how long the RF energy should be applied to the tissue. The electrosurgical generator may not allow the supply of RF energy to exceed a set threshold even if directed to by the connected electrosurgical instrument thereby providing a check or assurance against a faulty instrument command.

Further Embodiments

The above sections described different steps tied to the sealing process performed by the electrosurgical system. Specifically, the identification of the RF peak output condition is an important step in order to allow the electrosurgical system to manage the RF energy being supplied to the tissue. As described above, the RF peak output condition corresponds to the initial voltage ramp used to heat the tissue to a temperature where desiccation begins. The following embodiments are directed towards additional features that may be incorporated with or otherwise included with the electrosurgical system to better identify characteristics (e.g., type, thickness, condition) about the tissue undergoing the sealing process to address the possible issues with identifying the RF peak output condition. In this way, the electrosurgical system can also be configured to better and/or more efficiently calculate how much RF energy to provide to the tissue undergoing the sealing process and subsequently modify the generated RF energy accordingly in real-time.

A. Identifying Tissue

The identification of the type of tissue (as well as the current state of the tissue) can be useful for the electrosurgical system in managing the sealing process. Based on the identification of the thickness of the tissue being sealed or whether the tissue was previously sealed (e.g., repeat sealed), the RF energy output can be modified such that an appropriate amount of RF energy is provided. For example, the electrosurgical system can provide more RF energy for thicker tissues as thicker tissues may require more energy to heat up for desiccation to begin or more energy to remove the requisite amount of fluid/water from the tissue. In contrast, tissues that have been previously sealed or are on the thinner side may be provided less RF energy as less energy may be needed to heat up the tissue or remove the fluid/water from the tissue.

a. % Max to Identify Repeat Seals

By using a measured maximum current value, the electrosurgical system can calculate a variety of different threshold values. These threshold values based on the measured maximum current values can be used by the electrosurgical system to correspond to different conditions related to the tissue undergoing the sealing process. One threshold that can be implemented may be used to identify whether the tissue previously underwent the sealing process (e.g., repeat seals).

Tissue that was previously sealed may have a significant amount of fluid/water removed in the prior sealing cycle. As such, if the previously sealed tissue was again exposed to the same high amounts of RF energy, the tissue can experience negative effects such as sticking, thermal spread and jaw heat. Therefore, there is a need for the electrosurgical system to identify repeat seal scenarios in order to minimize and reduce the amount of RF energy being applied to tissues that were previously sealed.

Generally, tissues that underwent sealing before have little remaining fluid/water content. Therefore, any fluid/water remaining in the tissues will vaporize quickly when the tissue undergoes the sealing process again. The speed by which the little remaining fluid or water content vaporizes in the previously sealed tissues can correspond to a sharp drop in current relative to a maximum current measured immediately prior with that tissue. This behavior for the measured current is much different compared to if RF energy is applied to tissue that was not previously sealed. Thus, by using a threshold (e.g., a low % of the maximum current) corresponding to this sharp drop in measured current from the maximum measured current, the electrosurgical system can be configured to detect and identify if and when a repeat seal condition is present (e.g., if the measured current reaches the low % threshold within a pre-determined period of time from when the maximum current was measured). Accordingly, the electrosurgical system can then modify the RF energy being delivered to the previously sealed tissue to be different, compared to if that same tissue was not previously sealed.

b. Identifying Tissue Thickness Based on Maximum Current

Figure 11A:
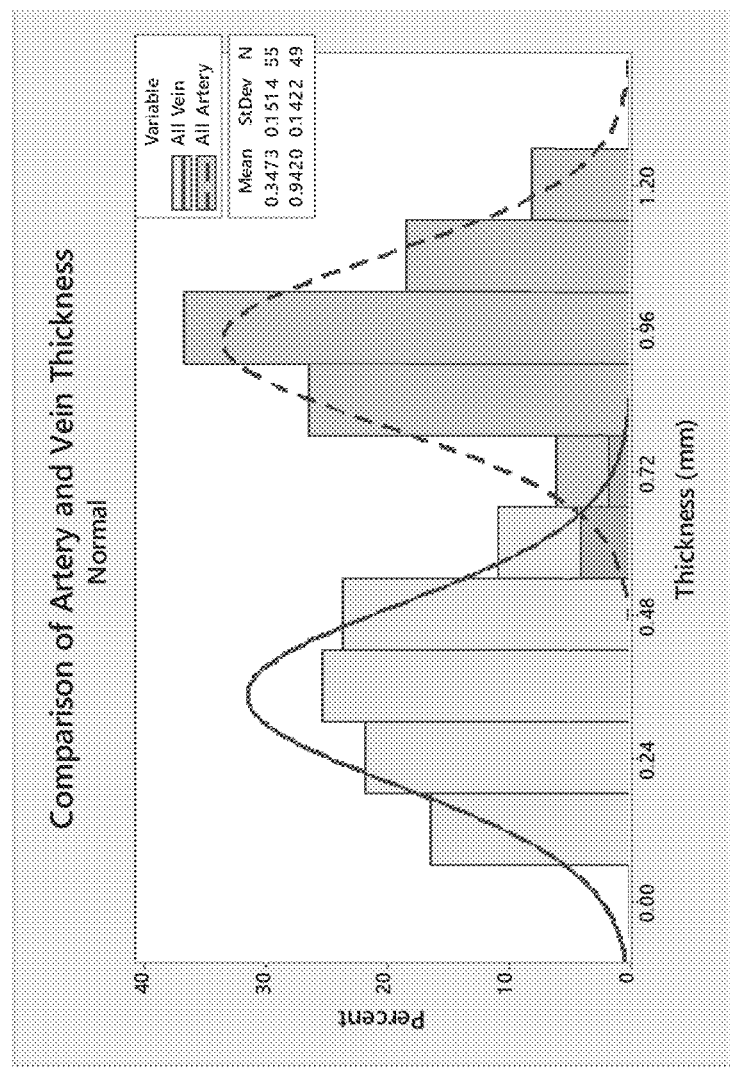
FIG. 11A-FIG. 11D are graphical representations comparing characteristics associated with tissues having different thicknesses—specifically between veins and arteries—in accordance with various embodiments of the present invention.
Figure 11B:
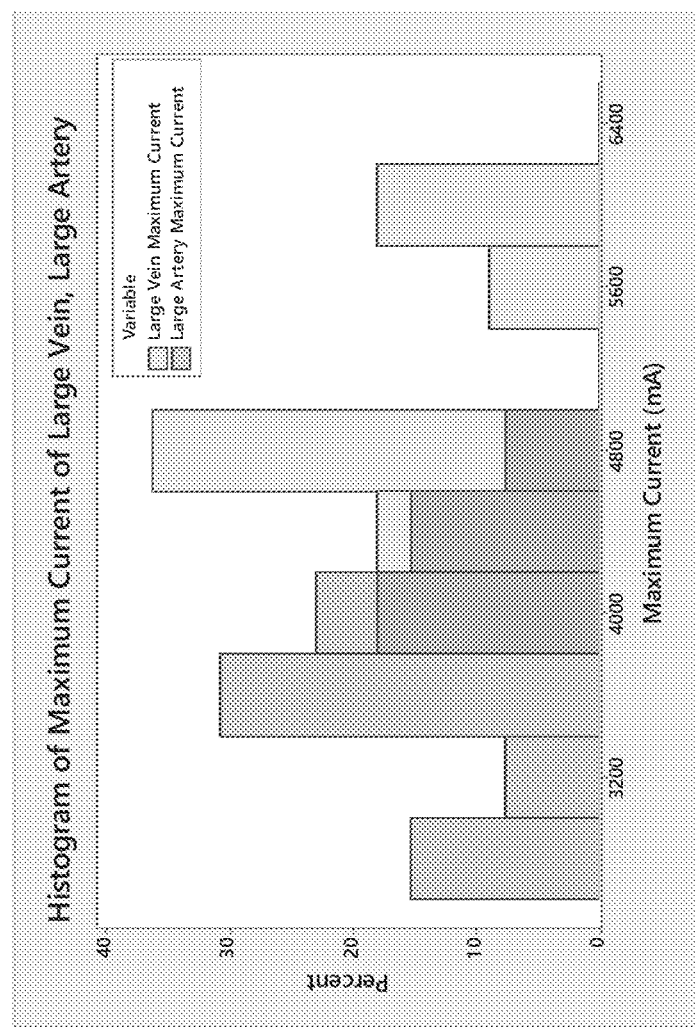

With a maximum current measurement, the electrosurgical system can determine information about tissue that can be used to manage the RF energy being used in the sealing process. In one embodiment, the electrosurgical system can calculate a thickness of the tissue being sealed based on information related to the maximum current measurement. An example illustration (see FIG. 11A) shows a comparison of thickness between different tissue types (e.g., veins and arteries) of similar diameters. Generally, maximum current is inversely proportional to tissue thickness. This assumes, however, that the area and conductivity of the tissue undergoing the sealing process is constant/same across different samples being sealed. In the case of an electrosurgical instrument, the length of the load is the thickness of the tissue captured in the jaw of the electrosurgical instrument. The relationship between maximum current and tissue type and/or thickness can further be seen in FIG. 11B, which compares large arteries to veins for the same area with different thicknesses in connection with the amount of current being drawn. Arteries typically having thick walls reinforced with smooth muscle. As such, arteries are generally characterized as being thicker than veins.

Because different types of tissue can have different thicknesses, the electrosurgical system can be configured to identify the type of tissue being sealed based on the measured maximum current (and in turn the calculated thickness) and use that information to modify the RF energy subsequently used in the sealing process. For example, the thickness of arteries is different from the thickness of veins (presuming that each of the arteries and veins being sealed have similar diameters). Therefore, tissue thickness can be seen as corresponding to the conductivity of the tissue (i.e., conductivity is higher for thinner tissues). The following equation can be used to summarize this relationship:

$$\text{Tissue Thickness} \propto \frac{1}{\text{Maximum Current}}$$

Accordingly, the electrosurgical system can modify the amount and manner the RF energy is being generated by the electrosurgical generator in order to accommodate the thickness of the tissue being sealed.

Figure 11C:
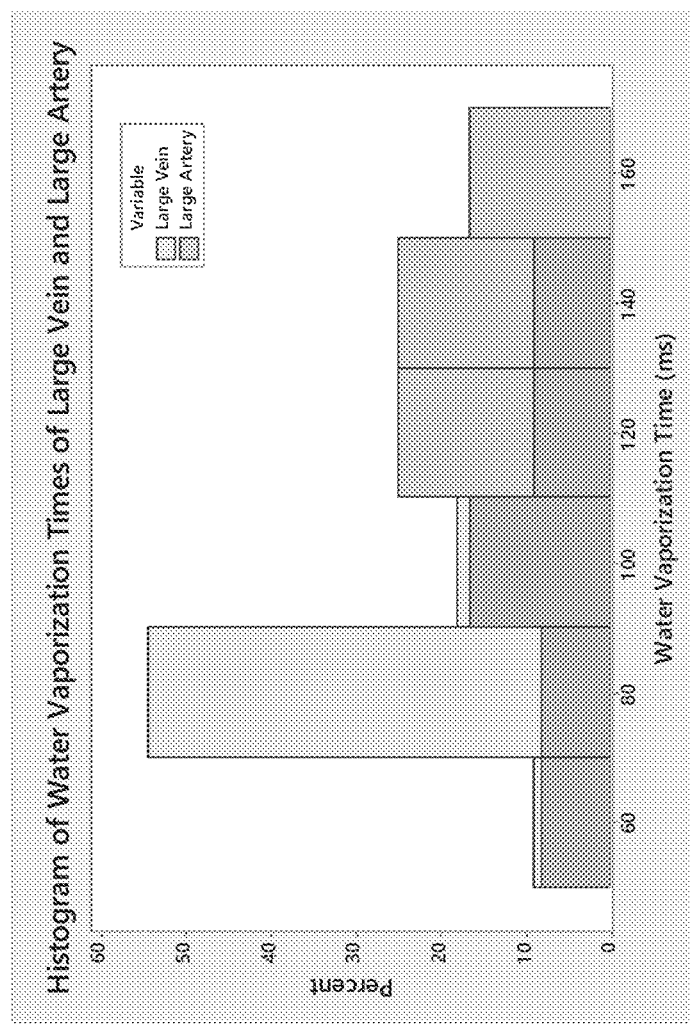

Tissue thickness could also be identified by the electrosurgical system based on monitoring a time needed for the tissue undergoing the sealing process to reach the point where fluid or water content begins to vaporize. Generally, thicker tissues will take a longer time to reach the water vaporization point compared to thinner tissue (presuming similar area and conductivity) as thicker tissue may need more energy to heat up a larger amount of tissue to the appropriate temperature for vaporization. This relationship can be seen in FIG. 11C where the water vaporization time is generally longer for large arteries compared to large veins as arteries are typically thicker than veins. The following equation can be used to summarize this relationship:

$$\text{Tissue Thickness} \propto \text{Water Vaporization Time}$$

Since tissue thickness has correlations with both measured maximum current and water vaporization time, the combination of these two relationships could be used to better distinguish between different tissue thicknesses. The following equation for tissue thickness combines the two earlier relationships.

$$\text{Tissue Thickness} \propto \frac{\text{Water Vaporization Time}}{\text{Maximum Current}}$$

Figure 11D:
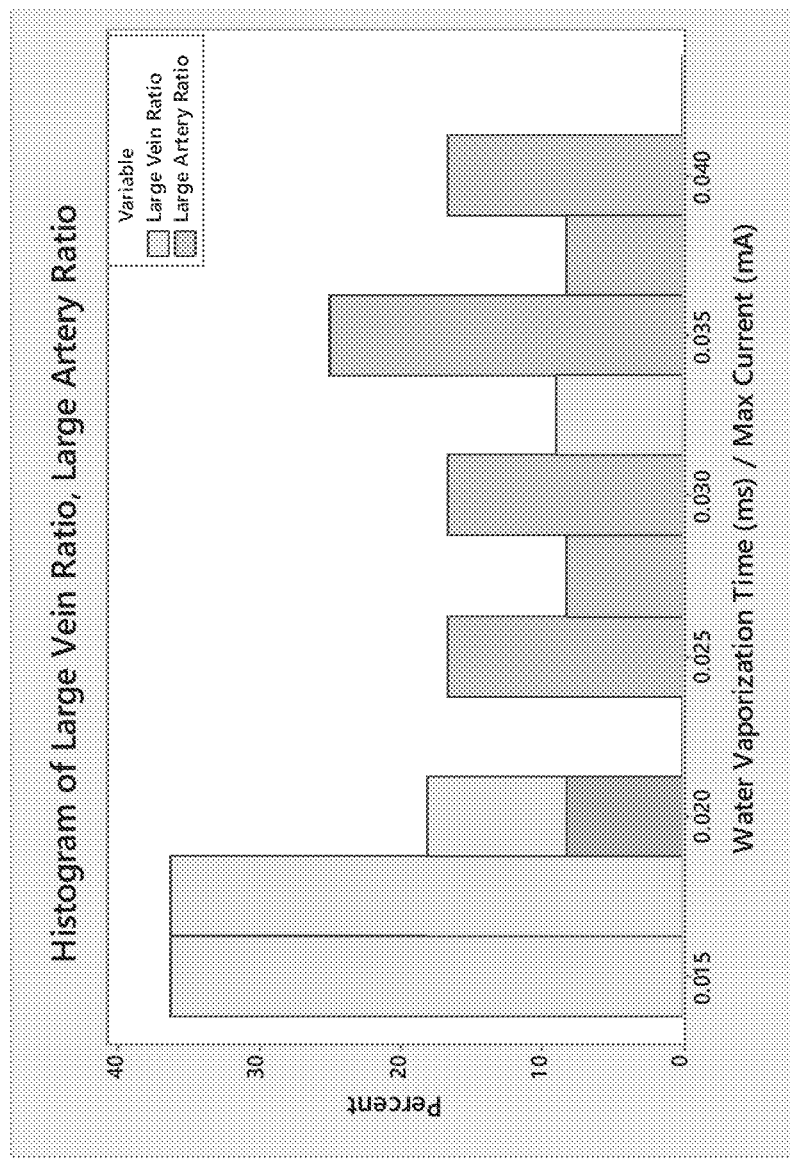

Furthermore, FIG. 11D illustrates how the data shows the distinction/separation between the ratio of water vaporization time and max current corresponds to the two different tissue thicknesses.

Because data about both the water vaporization time and the maximum current for the tissue can be obtained early during the sealing process by the electrosurgical system, the electrosurgical system is thus able to calculate and determine the possible tissue thickness of the tissue being sealed using the measured water vaporization time and measured maximum current. In doing so, the electrosurgical system can subsequently modify the RF energy being generated by the electrosurgical generator so the amount or method of RF energy delivery to the tissue can be made to be based on the thickness of the tissue being sealed.

Figure 12A:
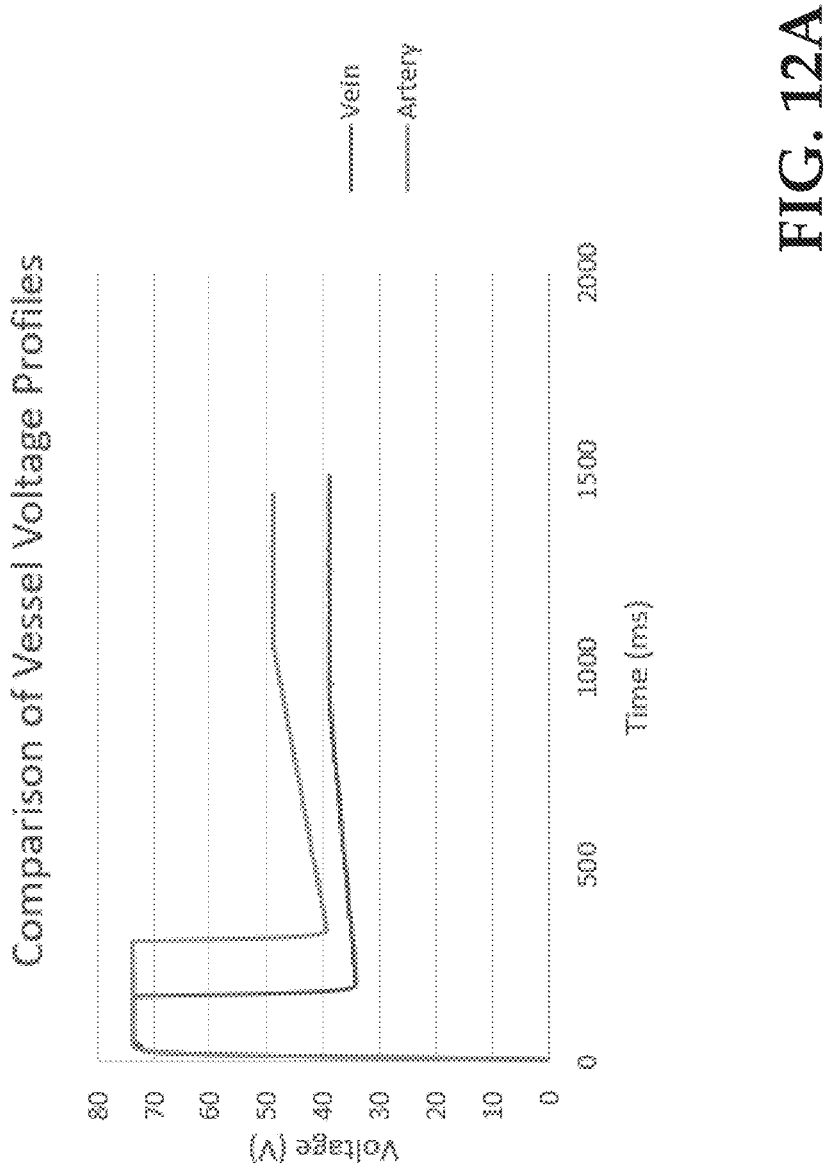
FIG. 12A-FIG. 12C are graphical representations showing how tissue thickness can affect the delivery of RF energy during the sealing process in accordance with various embodiments of the present invention.

Finding out the thickness of the tissue can be useful in how the electrosurgical system can modify the amount and delivery of the RF energy during the sealing process. For example, the electrosurgical system can control the voltage ramp that defines the fluid/water vaporization rate and the temperature of the tissue after vaporization begins. The difference can be seen in FIG. 12A.

As illustrated in the figure, the beginning of the voltage ramp is the same for both different types of tissues (e.g., arteries and veins). The use of the initial voltage ramp is important because it is at this point the tissue (that presumably hasn't been previously sealed) still has all of its fluid/water content. Therefore, the electrosurgical system is configured to heat the tissue to a high enough temperature to begin vaporization of the fluid/water. However, as the fluid/water is vaporized, steam will be generated from the tissue. The electrosurgical system can monitor the rate at which the tissues are heated in order to detect situations where excessive steam generation can damage the seal being formed.

Once the appropriate temperature has been reached, the electrosurgical system can then modify the voltage of the RF energy to drop to a lower voltage amount and subsequently gradually rise the voltage level in order to maintain the temperature of the tissue (and in turn control the vaporization of the fluid/water in the tissue at a controlled rate). For thinner tissue with a lower ratio value, the electrosurgical system can use a lower voltage start value to lower the water vaporization rate. On the other hand, the electrosurgical system can retain a higher voltage start value for thicker tissue as more energy may be needed to heat the temperature of the tissue for the rate of water vaporization to be maintained. Another benefit of retaining a higher start value for thicker tissue may also be that a lower voltage may cause the temperature to drop too much for thicker tissue which interferes with the vaporization process that is already in progress.

As the tissue desiccates, the volume of the tissue may decrease thereby making it easier for the electrosurgical system to increase the temperature of the tissue. A continuous increase in voltage will eventually result in the tissue reaching high temperatures (e.g., 200-220° C.), which can damage the collagen structure of the seal, resulting in lower seal reliability. Therefore, stopping the gradual voltage ramp when the tissue temperature is within acceptable or predetermined limits can be useful in optimizing the seal being produced on the tissue. Similar to the initial voltage ramp, the ratio value is used to set higher ramp endpoints for thicker tissue and lower ramp endpoints for thinner tissue.

The ratio value allows the electrosurgical system to adapt the RF energy output to be optimized for different types of tissues (e.g., tissues having different thicknesses). Without this identification and the ability to accurately modify the voltage profile of the RF energy, a single voltage profile would need to be used by an electrosurgical generator for all tissue types which results in some tissue either being heated too hot or not heated hot enough during the seal cycle.

Figure 12B:
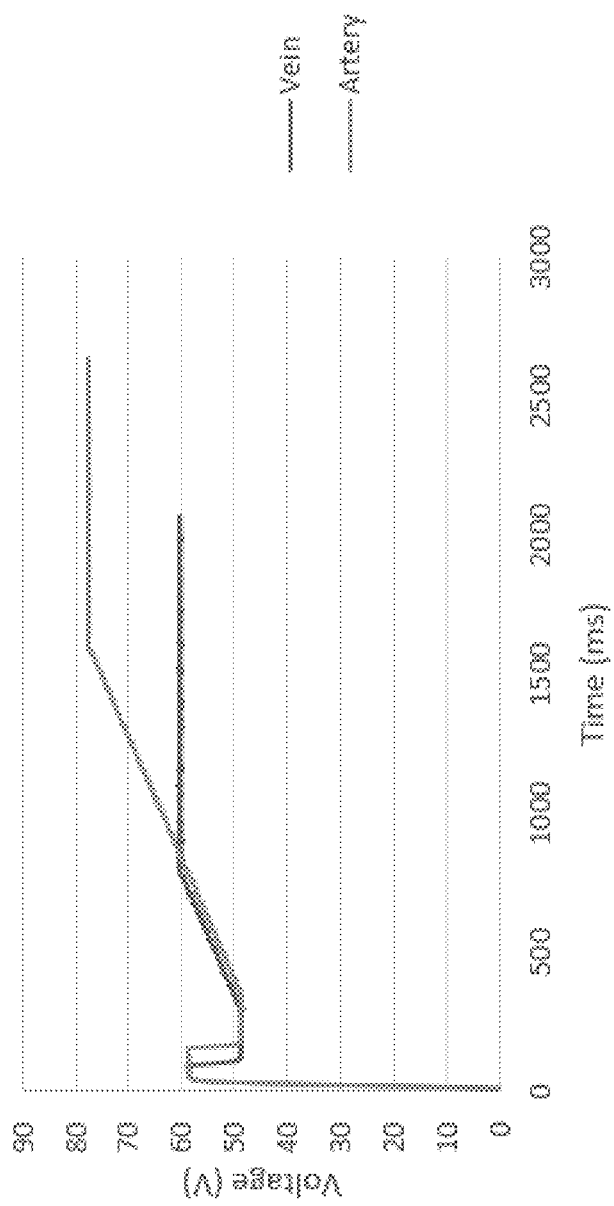

FIG. 12B illustrates how tissue thickness can also be used by the electrosurgical system to calculate when the gradual voltage ramp for the RF energy should be terminated. Depending on a variety of different factors detected by the electrosurgical system, such as sealing properties of the electrosurgical instrument being used, the electrosurgical system may initially utilize the same gradual voltage ramp starting voltage and ramp rate for different types of tissues. However, the ratio value for different tissue thicknesses can be used by the electrosurgical system to modify when a hard shutoff point for the gradual voltage ramp can be implemented. Thicker tissue can receive a higher voltage in the gradual voltage ramp before ending, while the gradual ramp for thinner tissue is ended at an earlier voltage. In this case, the gradual voltage ramp start point and ramp slope may be the same for all seals being performed on different types of tissue but the gradual voltage ramp endpoint and total duration can vary.

Figure 12C:
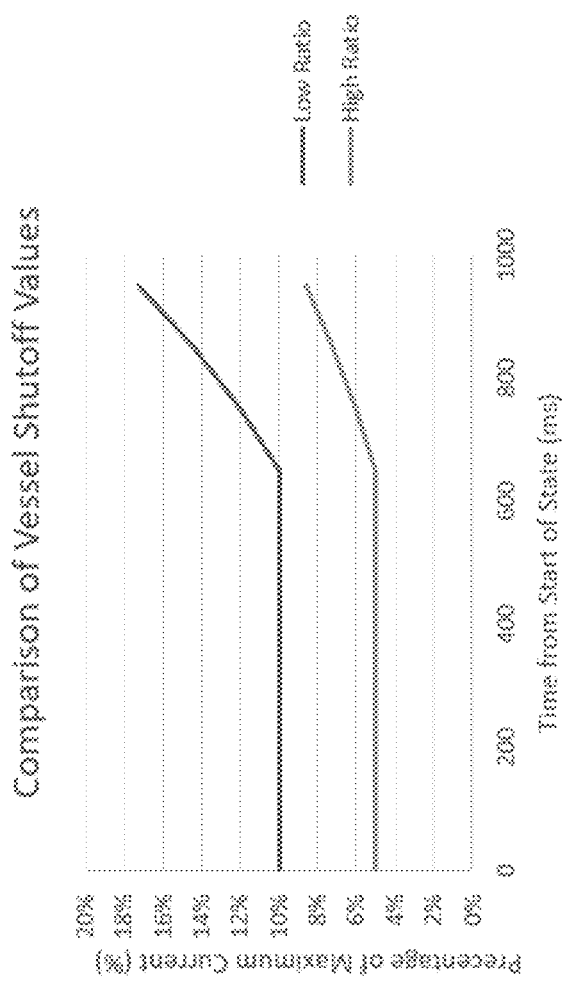

Last, FIG. 12C illustrates how the tissue thickness can also be used by the electrosurgical system to identify when the seal cycle for the tissue being sealed should be ended. In particular, the ratio value associated with the tissue can be used by the electrosurgical system to set the endpoint (e.g., based on a % of the measured maximum current) of the seal cycle. Thinner tissue with a low ratio value generally desiccates quicker (depending on how the voltage is set). Furthermore, thinner tissue will also have a higher current value for the same level of desiccation (compared to thicker tissue). For this reason, it can be desirable to have the electrosurgical system set seal-cycle endpoints earlier and/or at higher % thresholds (in relation to the maximum current) for thinner tissue based on the low ratio values.

On the other hand, thicker tissue with a higher ratio value may draw less current for the same level of desiccation (compared to thinner tissue). As such, thicker tissue may take longer to seal (depending on how the voltage is set). To account for the additional needed RF energy, the electrosurgical system may set the endpoints for the seal-cycle at lower % thresholds (in relation to the maximum current) or later in the seal cycle.

B. Identifying Maximum Current Peaks

Predicting and/or identifying when the RF output peak condition (e.g., maximum current) has occurred for different tissues can be difficult. As noted above, the electrosurgical system can use the identification of the RF output peak condition for the tissue being sealed as an indicator that fluid/water vaporization has at least begun. Furthermore, once the RF output peak condition is detected, the electrosurgical system can be configured to modify an amount and/or delivery of the RF energy to the tissue in order to minimize or prevent damage to the tissue caused by overexposure of high amounts of RF energy.

However, there may be situations where the RF output peak condition (e.g., maximum current) is not obvious to the electrosurgical system. For example, there may be multiple measured current peaks detected by the electrosurgical system within a period of time. These current peak values can be caused by a variety of different factors such as noise, fluids still existing in the tissue, or having multiple different types and/or thicknesses of tissues being sealed using the same electrosurgical instrument. Furthermore, situations where a true RF output peak condition that is achieved much later in the seal cycle may be missed if the electrosurgical system instead chooses to erroneously use any number of prior maximum peaks as the maximum peak.

Use of an earlier (i.e., lower) maximum rather than the later (higher) maximum peak by the electrosurgical system may cause issues with the sealing process. Some problems may include not properly heating the tissue to the predetermined temperature for vaporization of the fluid/water to being and failing to remove all the fluid/water from the tissue. Such issues may result in longer sealing times and/or incomplete seals.

To better identify situations where multiple peaks may be detected, the electrosurgical system may implement one or more features described as follows. First, the electrosurgical system can utilize an initial window that lasts for a pre-determined time period. This initial window can be seen in example graphical representations illustrated in FIG. 13A—FIG. 13C (which corresponds to the portion of the graph to the left of the vertical dotted line). Each of the figures (FIG. 13A-FIG. 13C) illustrate how the electrosurgical system can detect a maximum current in relation to the initial window. Generally, the electrosurgical system will be looking for measured maximum current value peaks located after the initial window as these peaks tend to be associated with the maximum RF output peak conditions.

The pre-determined time period associated with the initial window can be pre-set or customized based on the surgical procedure or type of tissue being operated on. In some embodiments, the initial window will be set by the electrosurgical system to correspond to a pre-determined period of time where a maximum current value would not generally be expected to be detected based on, for example, the tissue being sealed or the electrosurgical instrument being used. If the electrosurgical system detects a maximum current value during the initial window, the electrosurgical system can be instructed to continue monitoring for a pre-determined amount of time for subsequent maximums. If no other maximums are detected once the pre-determined amount of time elapsed, the original detected maximum may then be used.

Figure 13A:
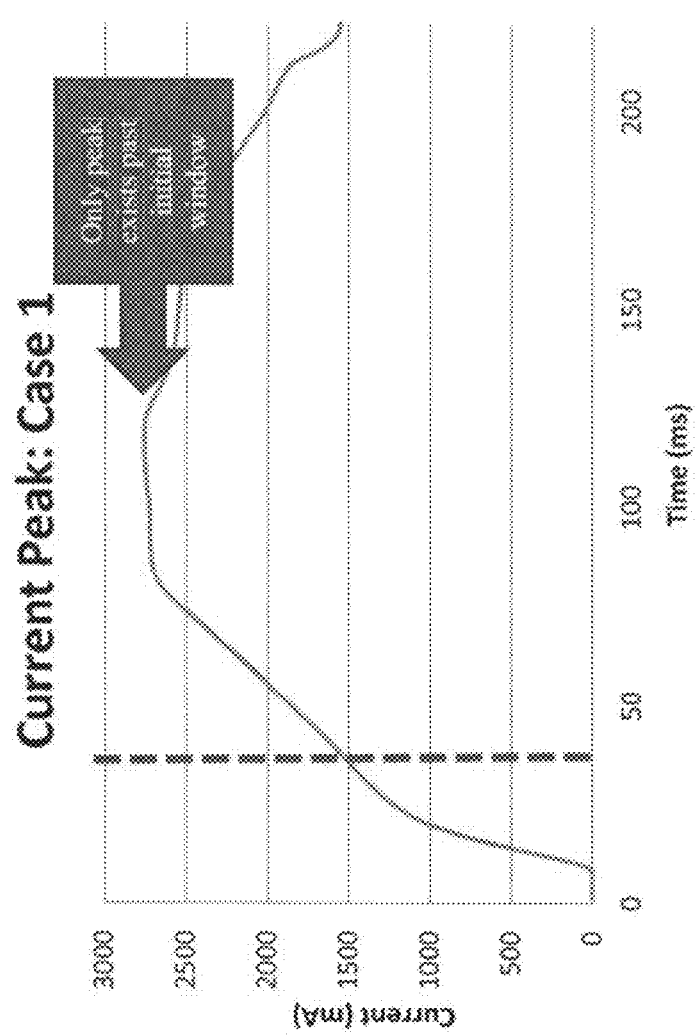
FIG. 13A-FIG. 13C are graphical representations illustrating the detection of a maximum current in accordance with various embodiments of the present invention.

In one embodiment, as illustrated in FIG. 13A, the electrosurgical system detects one maximum peak. The detected maximum peak is located when the electrosurgical system detects a maximum current measurement after the initial window. Upon detecting the maximum peak, the electrosurgical system can continue looking for a subsequent maximum for a pre-determined period of time or until the measured current associated with the tissue drops below a pre-determined threshold (e.g., the pre-determined threshold may correspond to a percentage of the measured maximum).

Figure 13B:
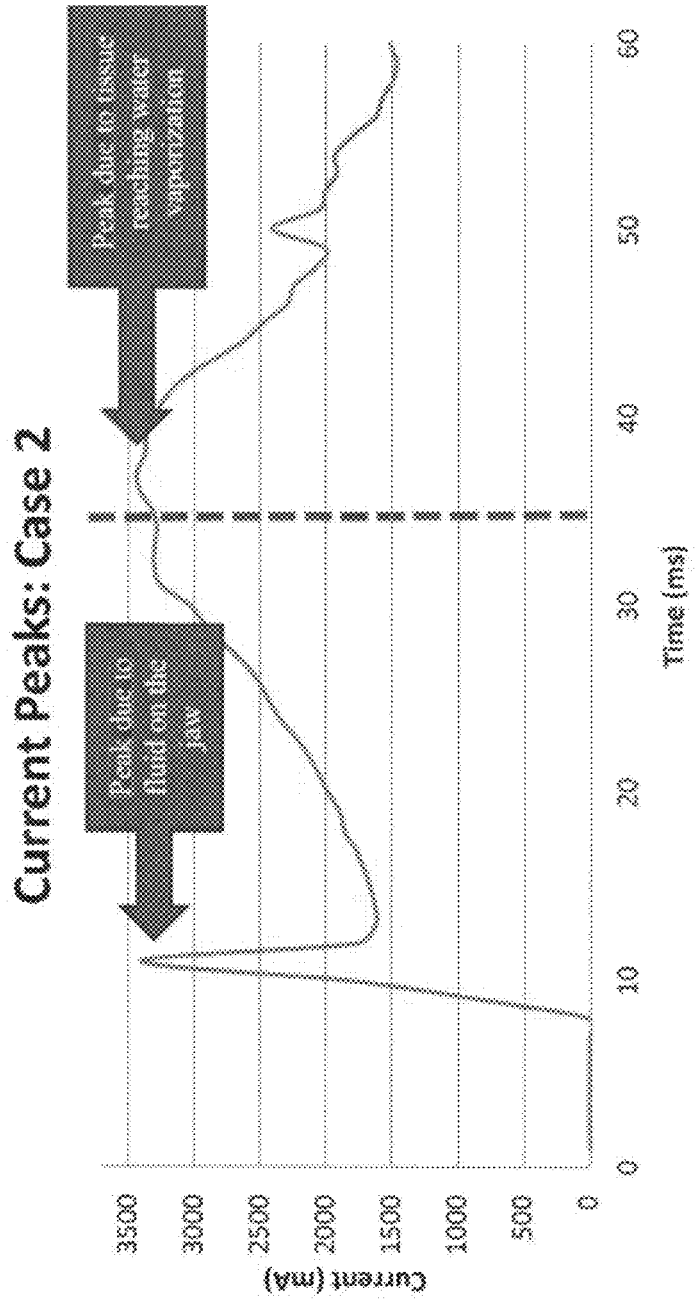

In a second embodiment, as illustrated in FIG. 13B, the electrosurgical system may detect multiple peaks in measured current associated with the tissue. In particular, the figure shows that a first peak is detected during the initial window while a later peak is also detected after the initial window. As noted above, the initial window can be used to indicate when water vaporization is generally supposed to occur in tissue at the earliest point in time. Therefore, the detection of a peak during the initial window may be used to identify that another issue may have caused a maximum peak to be detected that does not correspond to the tissue reaching the water vaporization point. For example, vaporization of fluid/water on the jaw can cause the electrosurgical system to falsely identify a peak as potentially being associated with the tissue reaching the water vaporization point.

Instead of just relying on the first maximum peak that is detected, the electrosurgical system can continue to monitor the measured current of the RF energy at the tissue until a later maximum current is detected. This later maximum current, since it is after the initial window, can be used to correspond to the RF maximum output condition and indicate that water vaporization for the tissue has begun. In this way, the electrosurgical system can better ensure that the tissue has been sufficiently heated and that fluid/water in the tissue has begun to vaporize. As described above, the electrosurgical system is configured to modify the RF energy being provided to the tissue based on the determination that vaporization for the fluid/water in the tissue has begun.

Figure 13C:
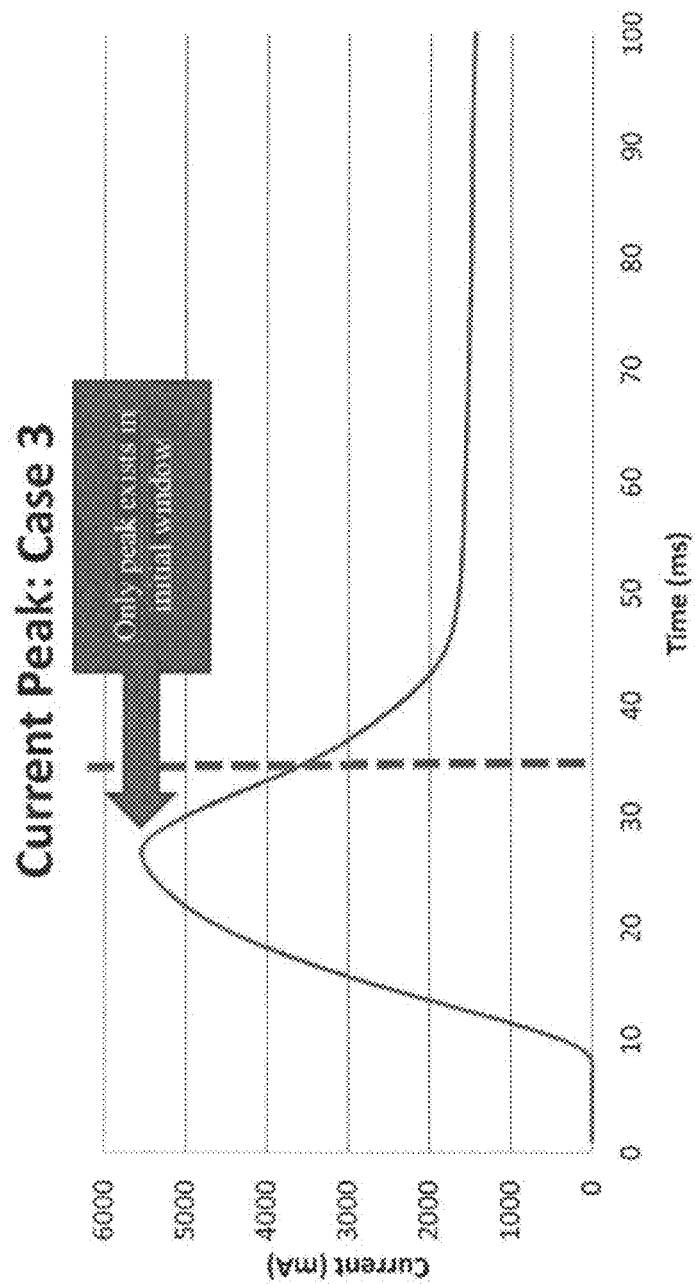

Although the initial window may generally correspond to a time period where vaporization is not expected to occur, it may also be possible for the electrosurgical system to decide that the maximum current detected during the initial window corresponds to the RF maximum output condition. For example, as illustrated in FIG. 13C, if the detected maximum is detected during the initial window and no subsequent maximum was detected for a pre-determined period of time after the initial window elapsed (i.e., the measured current is still lower than the previously measured maximum), the electrosurgical system can then use the previously measured maximum. The early maximum detected within the initial window can occur, for example, if the initial window being used by the electrosurgical system doesn't correspond to the thickness of the tissue being sealed (e.g., the tissue is thinner) or if the tissue underwent prior sealing.

C. Concavity Check

As noted above, vaporization of fluid/water in the tissue can be recognized by the electrosurgical system when the system detects an increase in current up until a maximum value and a subsequent drop in the measured current (e.g., down to a pre-determined threshold). However, the determination that the fluid/water of the tissue has begun to vaporize is based on an assumption that the tissue that is grasped by the electrosurgical instrument is a single circuit having a uniform state (e.g., type, thickness) in terms of electric field, compression, and/or temperature. Therefore, situations where multiple different types of tissues are all being sealed at the same time using the same electrosurgical instrument may pose challenges in properly identifying when the fluid/water of the different tissues have all begun to vaporize (e.g., scenario where portions of both veins and arteries are being grasped within the electrosurgical instrument). Relying on the first measured maximum current can result in only a portion of the tissue reaching the necessary temperatures to properly start the vaporization of the fluid/water. If the entirety of the tissue is not heated to the appropriate temperature needed to start the vaporization, subsequent removal of the fluid/water may not be efficiently carried out. As a result, the sealing time of the tissue may be extended or the resultant seal may be inconsistent or weak.

Figure 14A:
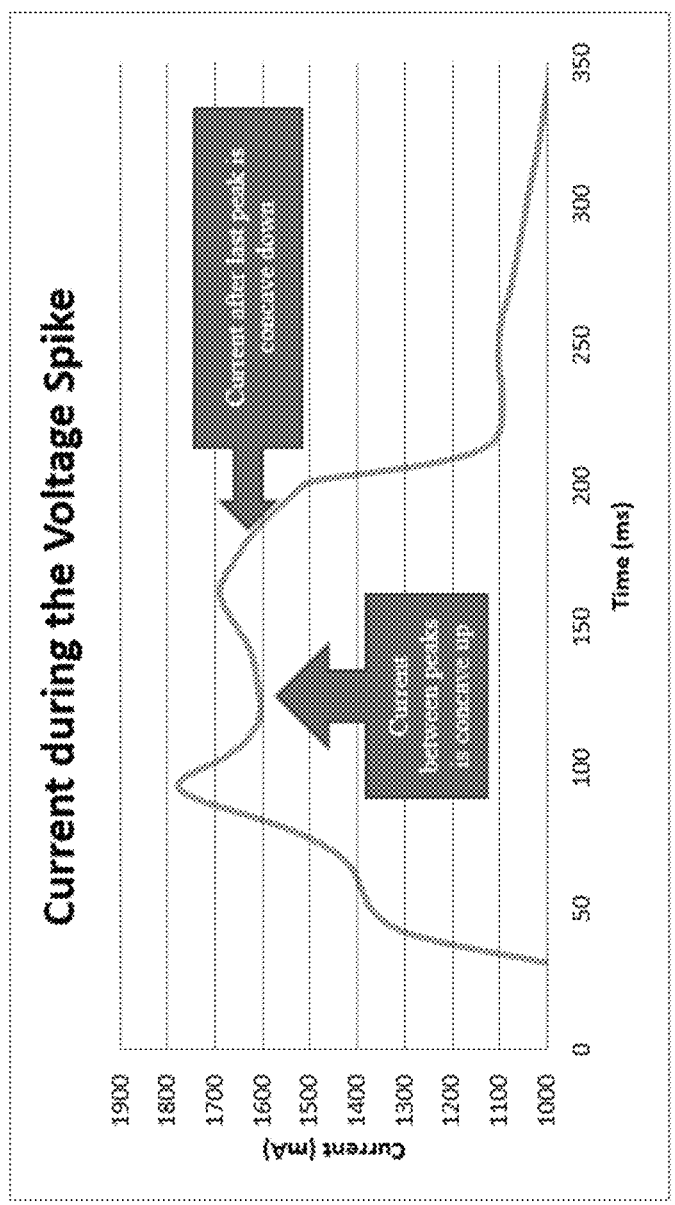
FIG. 14A and FIG. 14B are graphical representations associated with a concavity check performed by the electrosurgical system in accordance with various embodiments of the present invention.

An example scenario is illustrated in FIG. 14A where two different peaks are detected by the electrosurgical system. The two different peaks can correspond to at least two different tissues (e.g., thin tissue such as a vein and thicker tissue such as arteries). In one embodiment, the electrosurgical system may initiate steps in modifying the RF energy after the first maximum current was detected (in connection with the thin tissue) and the subsequent current measurements dropped below a pre-determined threshold (e.g., % based on the maximum current). However, in doing so, the electrosurgical system may have identified that the fluid/water in the thin tissue has begun to vaporize but failed to take into account the thicker tissue that is also being sealed. The thicker tissue that is also being sealed has not yet reached the necessary temperature to begin vaporizing the fluid/water content. Changes to the RF energy at this point by the electrosurgical system may affect the ability of the electrosurgical system to vaporize the fluid/water in the thicker tissue thereby impacting the quality of the seal produced in connection with the thicker tissue.

To determine whether a subsequent peak may be present, the electrosurgical system can perform calculations based on the speed in which the current measurement drops from the detected maximum for a pre-determined period of time. For example, if the drop in the measured current (detected by the electrosurgical system) slows down prior to flatlining and then increases, this behavior can be used by the electrosurgical system to indicate that a subsequent peak may be occurring if the heating of the tissue continues. If there is a possibility that a second peak can occur, the electrosurgical system may maintain the initial increase in voltage (i.e. initial voltage spike) to the tissue for the purposes of heating the tissue to the temperature sufficient for vaporizing fluid/water in the tissue. By having the electrosurgical system monitor for this pattern (e.g., drop, flatline, and rise in measured current), the electrosurgical system can make predictions as to when subsequent peaks may be possible. If subsequent peaks in current are anticipated, the electrosurgical system may or may be instructed to continue the initial voltage spike so that other portions of the tissue can be heated.

Figure 14B:
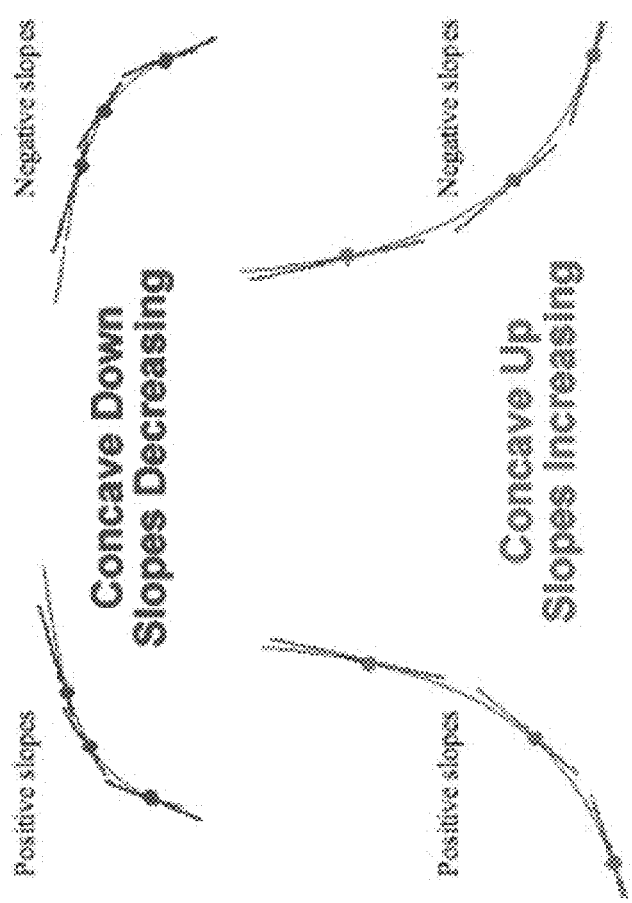

To determine whether subsequent peaks are potentially occurring, the electrosurgical system can be configured to calculate second derivatives of the measured current and compare the output to the concavity of the rate of change of the current. FIG. 14B illustrate example concavity checks where the second derivative of the measured current is compared. Depending on whether the second derivative of the measured current is positive or negative while the rate of change is concave up, the electrosurgical system can determine whether the initial voltage spike should be continued. If the second derivative is positive while the rate of change is concave up, the electrosurgical system can continue the initial voltage ramp for a pre-determined period or until the second derivative is negative for a pre-determined period of time. This continued voltage ramp can be maintained by the electrosurgical system even if the measured current crosses one or more pre-determined thresholds associated with a previous maximum current measurement. By maintaining the initial voltage ramp for the above conditions, the electrosurgical system allows for all portions of the tissue (which may include different tissue types or tissue thicknesses) to be heated by the electrosurgical system to appropriate temperatures that begins the vaporization of the fluid/water in the corresponding portions of the tissue.

Detecting and measuring concavity of the measured current via the electrosurgical system can have various challenges. For example, derivatives have more inherent noise than their parent signals. Furthermore, the events that are detected by the electrosurgical system using the derivatives can occur within short time intervals (e.g., 5-50 ms) which may be difficult to identify and distinguish with the noise. To account for the noise, in one embodiment, is by implementing an approximation of the second derivative by comparing the drop in the measured current over a time interval and the drop in the measured current over the previous time interval. Each time interval can be set to be relatively short (e.g., 4 ms). By having the electrosurgical system compare two adjacent time intervals and determine if the most recent drop is smaller than the previous drop, then the electrosurgical system can determine if the rate of change in the current is slowing down thereby indicating that the current is concave-up. In contrast, if the electrosurgical system detects that the most recent drop is equal to or greater than the previous drop, then the electrosurgical system can determine that the rate of change for the current may not to be concave-up.

By using the above approximation mechanism, the result of this computation by the electrosurgical system can then be stored as a variable. Generally, if the measured current is below the threshold value, the electrosurgical system can instruct the electrosurgical generator to end the initial voltage spike and move onto the next step/stage of the sealing process (e.g., dropping the voltage level down to a pre-determined threshold). However, with the concavity checks, the electrosurgical system makes additional checks to see if the initial voltage spike should be extended for a further period of time. If the variable (associated with the rate of change of the current) is zero (or linear) or negative (or concave-down), the electrosurgical system can terminate the initial voltage spike. However, if the variable is found to be positive (or concave-up), the initial voltage spike should not be ended at the current time. Instead, the electrosurgical system will maintain the initial voltage spike until a voltage termination condition is met (e.g., pre-determined time period), or a new next maximum is found. The concavity check cycle repeats & recalculates each time interval until the initial voltage spike is terminated.

Once fluid/water vaporization begins, the conductivity of tissue generally decreases. As such, it is not expected for the conductivity of the tissue to increase at any point as the RF energy is being applied to the tissue. Therefore, the electrosurgical system then tracks the measured current associated with the tissue in connection with various pre-determined thresholds (e.g., based on the maximum current). The pre-determined thresholds can be used to trigger an event with the electrosurgical system if a substantial increase in current (that is not expected) is detected. Triggering these pre-determined thresholds provides a way for the electrosurgical system to determine if the seal cycle is progressing in the opposite direction of what is expected. The triggering of these pre-determined thresholds informs the electrosurgical system that fluid/water vaporization in the tissue has not likely occurred in all parts of the tissue currently undergoing sealing.

Small and/or temporary increases may be allowed by the electrosurgical system in order to account for some tissue variability and/or noise. However, the pre-determined thresholds are generally a pre-determined percentage above the maximum peak of the measured current corresponding to when vaporization is detected. The percentages used by the electrosurgical system for the pre-determined thresholds can vary for various different situations. For example, the pre-determined thresholds can be set higher or lower based on how long the initial voltage spike has used or whether the pre-determined threshold has been previously triggered.

If the electrosurgical system detects that the pre-determined threshold has been crossed by the measured current, the electrosurgical system can enter a wait state which monitors for a maximum (i.e. peak) current followed by a drop. As noted above, detection of a maximum and drop in measured current can be used by the electrosurgical system to identify that fluid/water vaporization has begun in the tissue. If detected, the electrosurgical system can progress through the seal cycle to the next steps (e.g., after the voltage spike when desiccation begins in the tissue) which generally includes the voltage drop, gradual voltage ramp, and hold (as discussed above in steps 73-76 of FIG. 5).

The wait state (with the monitoring of the current) allows the electrosurgical system the capability to continuously check for the state of fluid/water vaporization in the tissue. If the fluid/water vaporization (i.e., desiccation) has not started, the electrosurgical system can perform various soft-resets in the sealing process in order to ensure that the RF energy being applied to the tissue properly heats the tissue (in order to properly create a seal that is not only quick but effective).

The use of the pre-determined threshold (to check that fluid/water vaporization has begun in the tissue) by the electrosurgical system can extend the overall duration of the seal cycle, which may cause some tissue to have some negative reactions to the increase RF energy exposure such as thermal spread, sticking, and jaw heat. However, the implementation of the pre-determined thresholds by the electrosurgical system are also beneficial as the thresholds will further ensure that the entirety of the tissue being sealed has been heated to a proper temperature sufficient for desiccation.

Desiccation is highly desired for creating an optimal seal and can therefore be afforded a high priority. Without the pre-determined threshold, the electrosurgical system may not be able to detect whether additional heating time is needed. As such, the electrosurgical system may need to add additional heat (via extended RF energy exposure) to every seal in order to ensure that desiccation has begun to ensure an optimal seal is being created. By implementing the pre-determined thresholds, the electrosurgical system can check the status of the fluid/water vaporization occurring within the tissue. As such, the pre-determined thresholds allow for shorter seal times for most seals that progress through the seal cycle as intended (e.g., does not trigger the pre-determined threshold requiring extending the initial voltage spike), as only a minority of tissue seals will take advantage of the pre-determined threshold. In this way, the electrosurgical system can balance between creating optimal seal strengths while minimizing outcomes associated with overexposure of the RF energy to the tissue (e.g., thermal spread, sticking, jaw temperature).

In addition to configuring the electrosurgical system to determine whether the tissue is being properly heated so that fluid/water vaporization occurs throughout the tissue, the above feature of monitoring the measured current can also be used by the electrosurgical system for other purposes as well. For example, the electrosurgical system can also detect events, such as the addition of water or saline to the seal site (e.g., surgical irrigation or immersing the jaw into fluid) or short circuits. These events can slow or stop desiccation (or fluid/water vaporization) occurring at the tissue. In one embodiment, the electrosurgical system is placed into a wait state until the events (e.g., short circuit or immersion of the jaw in fluid) are no longer present.

D. Using % Max to Progress Through the Sealing Process

When tissue has a voltage applied to it, the conductivity of the tissue increases as the ions and fluid/water in the tissue heats up. When the temperature of the tissue rises high enough, vaporization of the fluid/water in the tissue begins. Steam coming from the tissue as well as the loss of fluid/water from the tissue decreases the conductivity of the tissue. Therefore, as water vaporization begins, the current stops increasing and instead starts decreasing. This corresponds to a measured "peak" or maximum current at a point in time with the tissue, which can be identified by the electrosurgical system.

Threshold values (based on the measured maximum current) can then be used to detect the magnitude of the current drop after the measured maximum. However, variations in the composition or geometry of the tissue, or the presence of electrical noise in the signal may result in the electrosurgical system detecting a local maximum and momentary drop prior to other peaks or maximums which may correspond to the true maximum (i.e. a maximum current that can be used to indicate that the entire tissue has been heated to a sufficient temperature for fluid/water vaporization). Thus to identify a true maximum, the electrosurgical system utilizes threshold values that may be set as high as possible, yet low enough to reliably detect the true water vaporization point. The threshold values may be carefully balanced to minimize "overpulsing" of the tissue (corresponding to an application of high voltage too long after water vaporization begins), while preventing "underpulsing" of the tissue (corresponding to not providing enough RF energy to the tissue such that the temperature of the tissue is not sufficient for desiccation) by dropping the voltage prior to water vaporization begins in all areas of the tissue.

a. Break Values

Figure 15A:
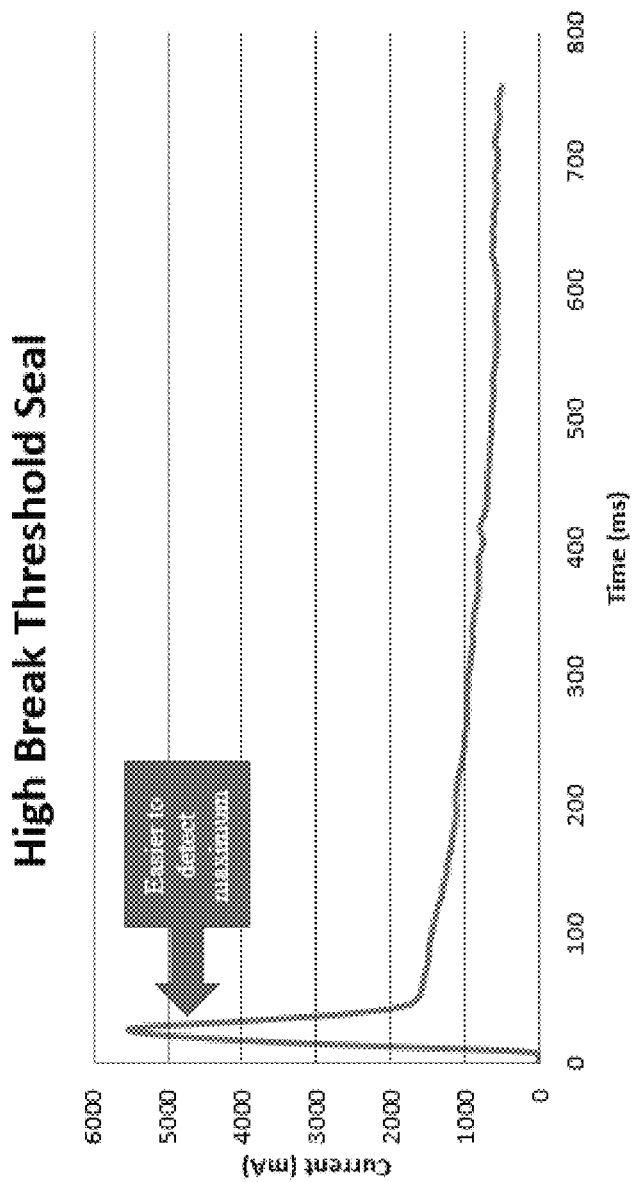
FIG. 15A-FIG. 15C are graphical representations associated with high, low and linear threshold values used by the electrosurgical system in accordance with various embodiments of the present invention.
Figure 15B:
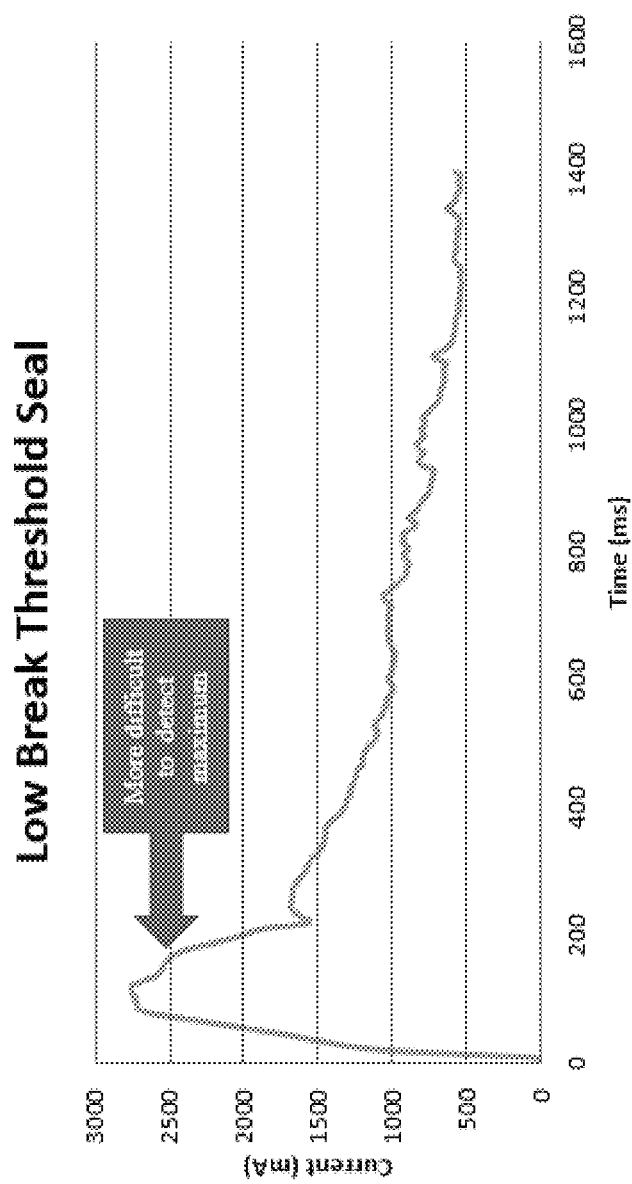

The threshold value used by the electrosurgical system can vary based on the properties of the tissue being sealed, as the tissue may have variations in composition or geometry. In addition, noise (such as being more likely at the beginning of the sealing process) and amplitude (e.g., A consistent 200 mA of noise has a better signal to noise ratio if the signal is 5 A compared to 3 A) can vary over time. In one scenario, a higher threshold value (such as 90% or 95% of the maximum current), as illustrated in FIG. 15A, is most effective for pieces of tissue which draw high amounts of current. Due to the high current draw, noise is a smaller percentage of the signal. In addition, the nature of high current draw makes it more likely that the tissue is thinner since conductivity in inversely proportional to the length of the conductor (i.e., thickness of the tissue). As such, thin tissue reaches the water vaporization point faster thereby making a shorter response time (via a smaller drop) more important. In contrast, a lower threshold value (such as 70% or 85% of the maximum current), as illustrated in FIG. 15B, can be more effective for tissue which draws less current (e.g., thicker tissue).

Furthermore, using the lower percentage based on the maximum value may result in a lower total drop. Because noise may become a larger percentage of the signal, more confidence is required to determine that the measured peak is the true maximum. Lower current draws indicate the tissue is more likely to be thicker. Particularly in the case of thicker tissue, it is possible, due to closure of the jaws, that certain parts of the tissue heat faster than other parts. Accordingly, the water vaporization point can occur at several different times for different areas of the tissue. Therefore, by having the electrosurgical system require to detect a larger drop in current via reducing the threshold value with a lower percentage (associated with the maximum current), is more likely to ensure that all portions of the tissue have reached the water vaporization point before ending the voltage spike.

Figure 15C:
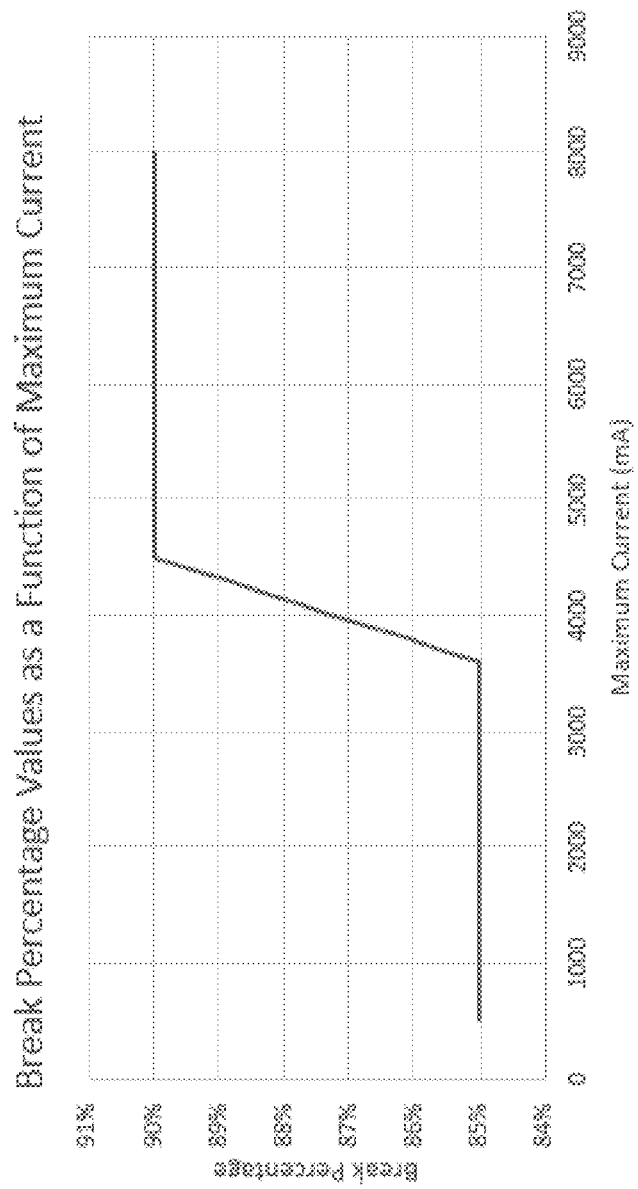

In between a higher threshold (such as 90%-95%) and a lower threshold values (70%-85%), a sliding linear threshold value can used by the electrosurgical system as illustrated in FIG. 15C. For example, if a 70% threshold is used for a maximum current of 3000 mA (70%*3000 mA=2100 mA), and a 90% break is used for a maximum current of 4000 mA (90%*4000 mA=3600 mA), all values between 3000 mA and 4000 mA could use a linear percentage between 70% and 90%. In that example, 3500 mA, being halfway between the two values, would use 85% (85%*3500 mA=3975 mA). The linear break percentage has two major advantages. The first advantage is consistency of output, so that small changes in maximum current (which may change due to variations in pressure, tissue moisture content, and contact resistance) do not result in substantially different behavior until there is a very large shift in maximum current. The linear threshold also allows for an area of overlap between different tissue types.

Continuing from the previous example, a possible scenario may have that the maximum current draw from arteries may generally be below 3000 mA but can rarely reach as high as 3600 mA. Furthermore, the maximum current draw from veins is generally above 4000 mA but the smallest veins can reach 3300 mA. Therefore, the linear break percentage between 3000 mA and 4000 mA allows for a compromise in the behavior of the algorithm, allowing the electrosurgical system to be optimized for both types of tissue (e.g., veins, arteries). Furthermore, the electrosurgical system can be more fully optimized in the range where there is generally no overlap of maximum current.

In addition to changing the break percentage based on the maximum current value, the break percentage used by the electrosurgical system can also be time-dependent. For a given type and amount of tissue, the time required for tissue to be heated to a temperature high enough for starting fluid/water vaporization may be consistent. The fluid/water vaporization time may be minimized for the smallest volumes of the highest conductivity tissue (such as 40 ms). Knowing this lower limit allows for the electrosurgical system to be configured to have a much more conservative break percentage (such as 50%) under this minimum expected fluid/water vaporization time. This allows the electrosurgical system to be less likely to end the initial voltage spike before the expected period of time for tissue to reach the temperature needed to begin fluid/water vaporization.

The use of the linear break also allows the measurements performed by the electrosurgical system to be more resistant to noise caused by small amounts of fluid on the jaws (as the fluid can boil very rapidly and much sooner than fluid/water in the tissue), which can create a false positive (or peak). The more conservative break percentage can be used by the electrosurgical system during the very beginning of the sealing cycle to ensure that the tissue being sealed has actually reached the fluid/water vaporization point. Furthermore, the more conservative break percentages can be implemented to require a higher level of confidence that the vaporization point has been reach before being able to end the initial voltage spike.

b. % Max to Identify Ramp Termination

The gradual voltage ramp may be used by the electrosurgical system to gradually increase the strength of the electric field in order to maintain a power output at the tissue as the conductivity of the tissue falls when fluid/water vaporization begins. The maintaining of the electric field by the electrosurgical system is to ensure that the fluid/water vaporization continues at a controlled rate. Generally, the electric field for a given voltage is inversely proportional to the thickness of the tissue. Therefore, in one embodiment, it may be desirable for the electrosurgical system to modify the voltage so that a higher voltage is provided for thicker tissue whereas thinner tissues may only need a lower amount of voltage.

As such, it may not be necessary for all tissue types to complete the entire voltage ramp during the gradual ramp state (e.g., step 75 of FIG. 5). Because thinner tissues (such as small arteries or veins) or thin tissue bundles do not need a high voltage potential to create a strong enough electrical field to desiccate the tissue quickly, a different (e.g., lower) % max threshold can be used to minimize the situation where maintaining extended high voltage potential can actually cause damage to the thin tissue if the thin tissue is heated excessively. In contrast, thicker tissue can be provided a higher % max threshold. Therefore, by having the electrosurgical system monitor the current behavior with respect to the maximum current, the ramp state for any tissue can be terminated by the electrosurgical system after the voltage reaches an acceptable level for that tissue type.

By using a % threshold to identify when to terminate the gradual ramp, the electrosurgical system can set the maximum voltage that can be achieved during the gradual ramp stage of the seal cycle for each different type of tissue. For example, in situations where thicker tissues are present, the electrosurgical system can set a threshold that allows the tissues to achieve a higher voltage (via use of a higher % max threshold) which in turns allows for a higher power output and longer seal time (in order to ensure that the water/fluid has been properly vaporized from the tissue). On the other hand, for thinner tissues the electrosurgical system can set thresholds that allow a lower voltage to be achieved. With both these situations, the electrosurgical system can be configured to implement an optimal tissue temperature regulation based on the tissue being sealed.

c. % Max to Identify RF Done (Seal Cycle Completion)

Similar to terminating the initial voltage ramp using a % max threshold, the application of the RF energy for sealing the tissue can also be terminated by the electrosurgical system using a corresponding % max threshold. There may be situations where the electrosurgical system may determine that the application of the RF energy should be terminated sooner (e.g., for certain tissues which do not require additional time or heat to seal such as thin tissue or tissue that previously sealed). The electrosurgical system can detect when the application of RF energy could be terminated when there has been sufficient desiccation (which is indicated by the measured current associated with the tissue flatlining).

The identification of when the RF energy should be terminated can be detected by the electrosurgical system using a % max threshold value with respect to the maximum current recorded during the initial voltage spike state. Once this % max threshold value has been reached, the electrosurgical system can terminate the sealing cycle (via termination of the RF energy being provided to the tissue). Endpoints can vary greatly across tissue types as the current reacts differently based on the tissue thickness and surface area. Furthermore, seal times can also vary between vessel categories (e.g., arteries may need to undergo the sealing process longer than veins due to their thicker vessel wall). As such, the electrosurgical system can set conditions based on other information gathered about the tissue to better suit different tissue types in setting up when the RF energy should be terminated.

d. % Max to Identify Tip Seals

When small amounts of tissue are sealed at the tip of the electrosurgical instrument, the small surface area may lead to very low current draw (e.g., low maximum measured current). At the end of such a seal cycle, the current may fall low enough for the electrosurgical system to mistaken the measurement as corresponding to an open circuit. By using an appropriate % max threshold value with reference to the measured maximum current allows for a lower open condition threshold to be available for the electrosurgical system to identify this specific low current scenario. If the peak current is low (such as with a tip seal), the electrosurgical system can be adapted to recognize this situation and allow these smaller tissue bites to seal successfully without triggering an unnecessary alarm condition corresponding to an open circuit scenario.

e. % Max for Dynamic RF Shutoff/Termination

Figure 16:
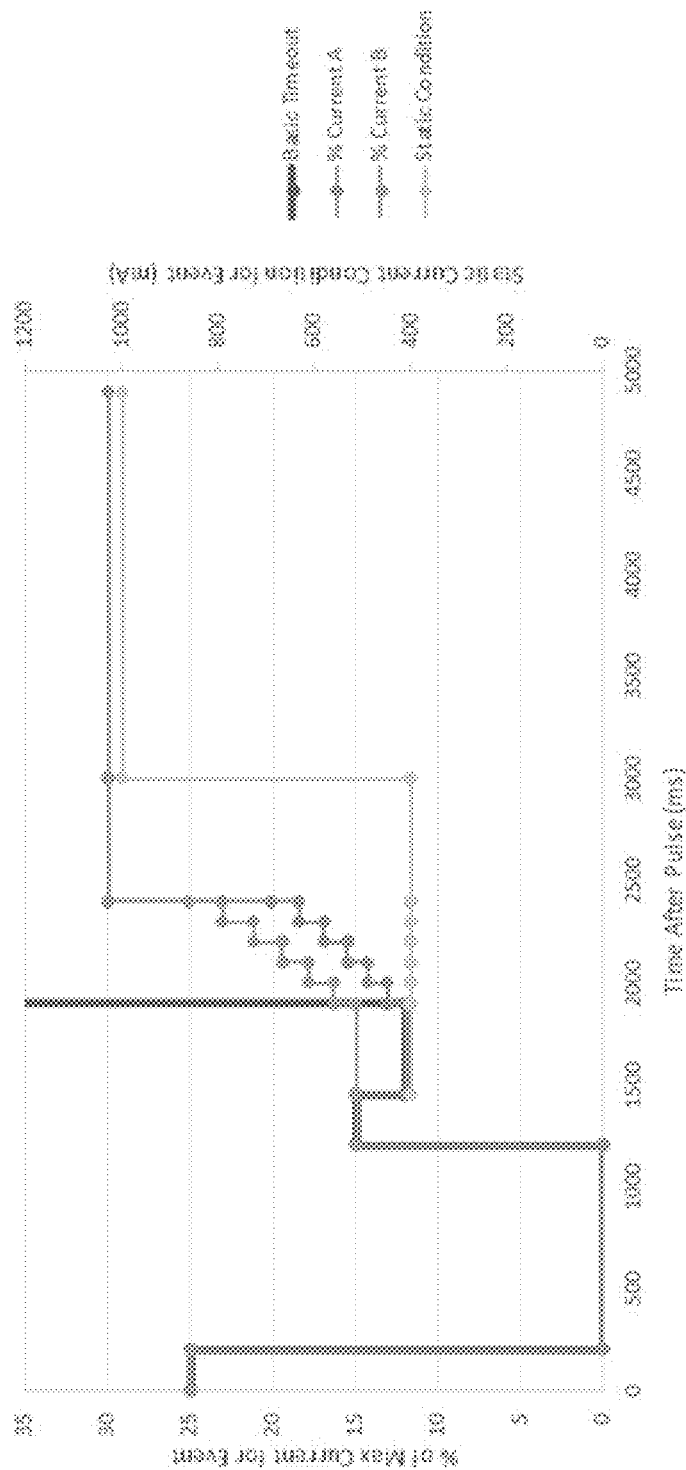
FIG. 16 is a graphical representation of using dynamic thresholds for RF shutoff in accordance with various embodiments of the present invention.

FIG. 16 is a graphical representation of the electrosurgical system using dynamic thresholds for RF shutoff. Similar to terminating the initial voltage ramp and RF energy using a static % value with reference to a maximum current value (as described above), the RF energy can also be terminated by the electrosurgical system using a dynamic shutoff curve that is based on real-time calculations made with respect to the maximum current value. If the electrosurgical system detects that the measured current meets or crosses one of the dynamic thresholds, this can be used by the electrosurgical system to indicate that the sealing process should be complete and that termination of the RF energy should be carried out.

In further embodiments, the dynamic threshold value, which triggers the end of the seal cycle, can also be incremented at a certain rate (1%, 10%, 15%, etc.) during or after a predetermined interval in a user state. The increase in the dynamic threshold value can also allow larger tissues to desiccate fully while allowing fast cooking (i.e. thinner) tissues to exit the seal cycle when they reach an acceptable % max current.

In further embodiments, time-based thresholds can also be used by the electrosurgical system to determine when to shutoff/terminate the RF energy. For example, if the tissue was not initially heated to a high enough temperature for desiccation to begin, the electrosurgical system may expose the tissue to RF energy for a longer than expected period of time. The time-based thresholds (e.g., time-out) can be used by the electrosurgical system to determine when to terminate the RF energy once the sealing process has elapsed longer than a pre-determined period of time (e.g., associated with a maximum time that tissue should be exposed to RF energy). The time-based thresholds can also be used by the electrosurgical system to identify possible issues with the current sealing process and inform the user (e.g., surgeon).

E. Detecting Water Vaporization Based on Voltage/Impedance Relationship

For a static resistor, the impedance of a circuit does not change as a function of the RF energy being applied to it. Nor does the impedance change as a function of how much power is flowing through the circuit. Neither of these characteristics are true for tissue as tissue impedance is variable. As RF energy is applied to tissue, the impedance of the tissue initially drops with increased ion conductivity as the tissue heats. Afterwards, an increase in the impedance of the tissue follows as fluid/water vaporization begins. The increase in impedance is due to both desiccation occurring with respect to the tissue (e.g., changing the composition of the tissue from approximately saline to approximately plastic) and the presence of steam in the tissue (which has a high impedance). The impedance-related trend generally exists for most tissue when the tissue is being sealed with an electrosurgical system and lasts several seconds (e.g., 2.5 seconds).

Figure 17A:
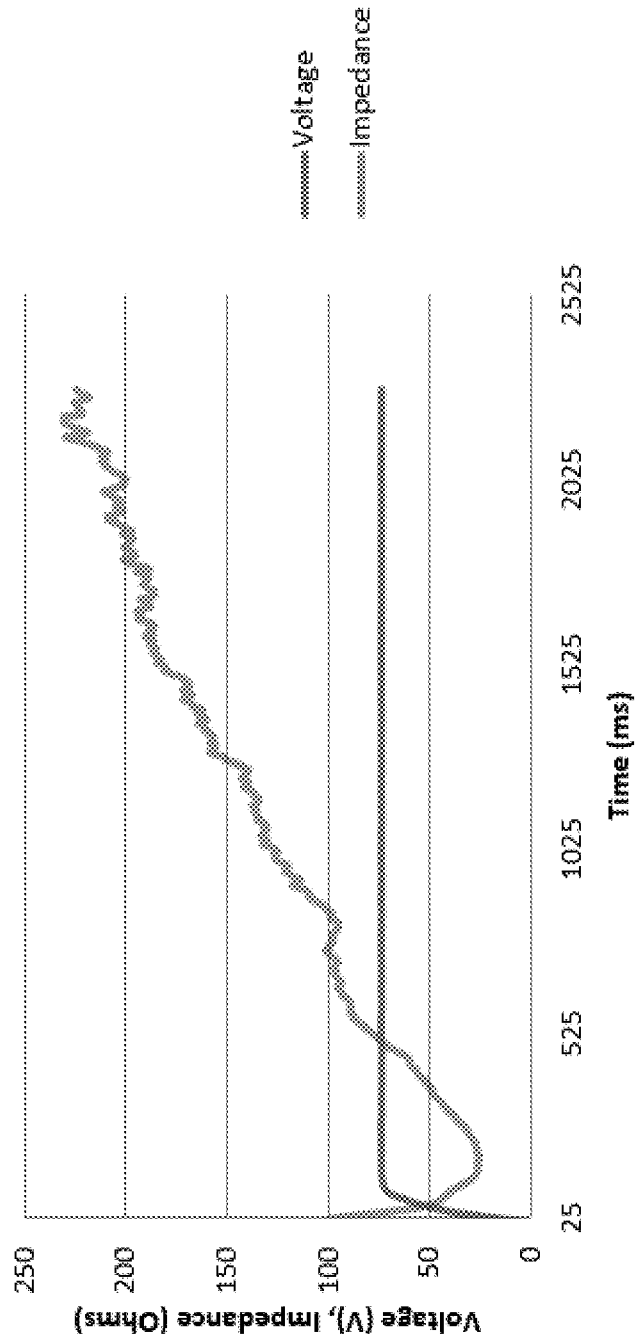
FIG. 17A-FIG. 17D are graphical representations illustrating relationship between voltage and impedance when detecting fluid/water vaporization in accordance with various embodiments of the present invention.
Figure 17B:
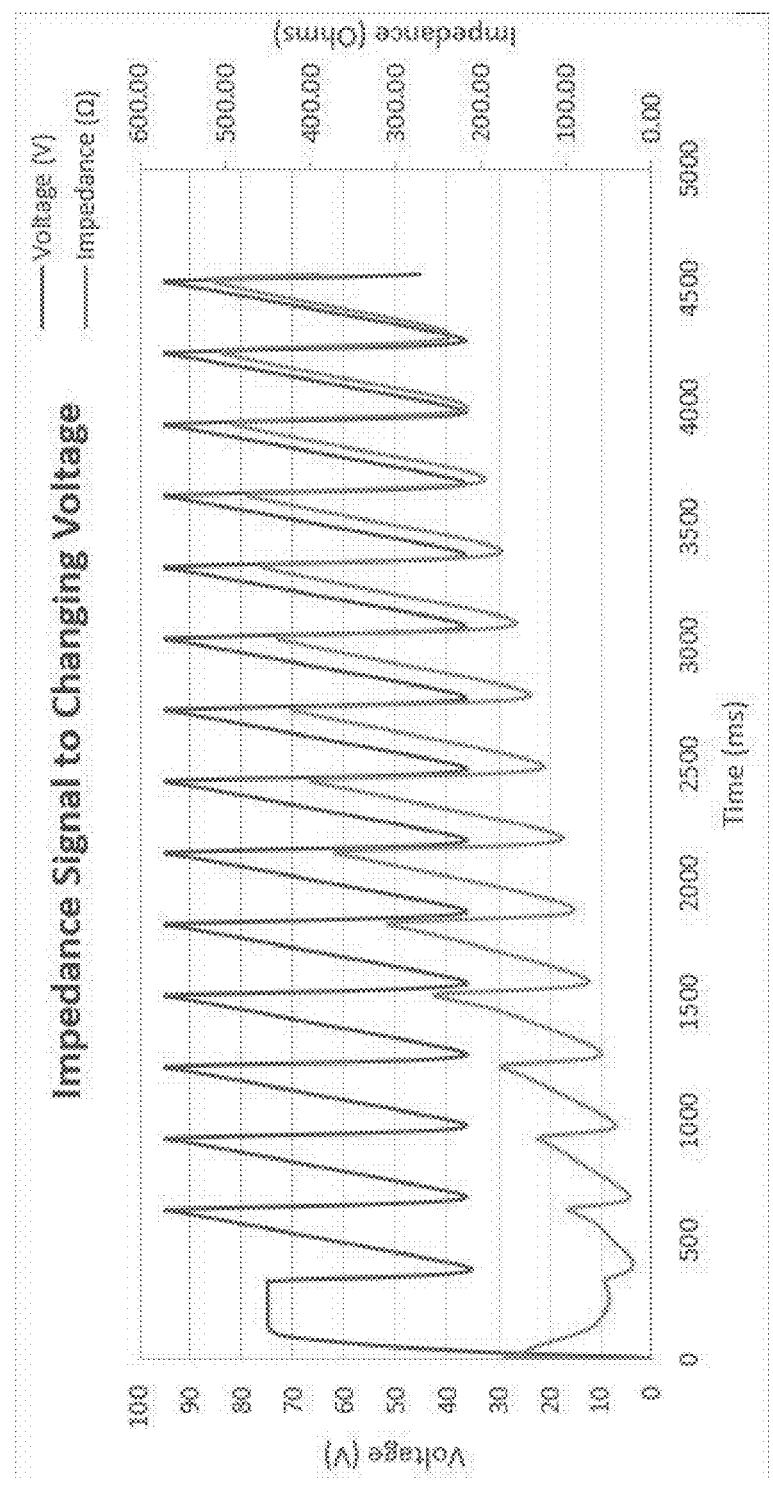
Figure 17C:
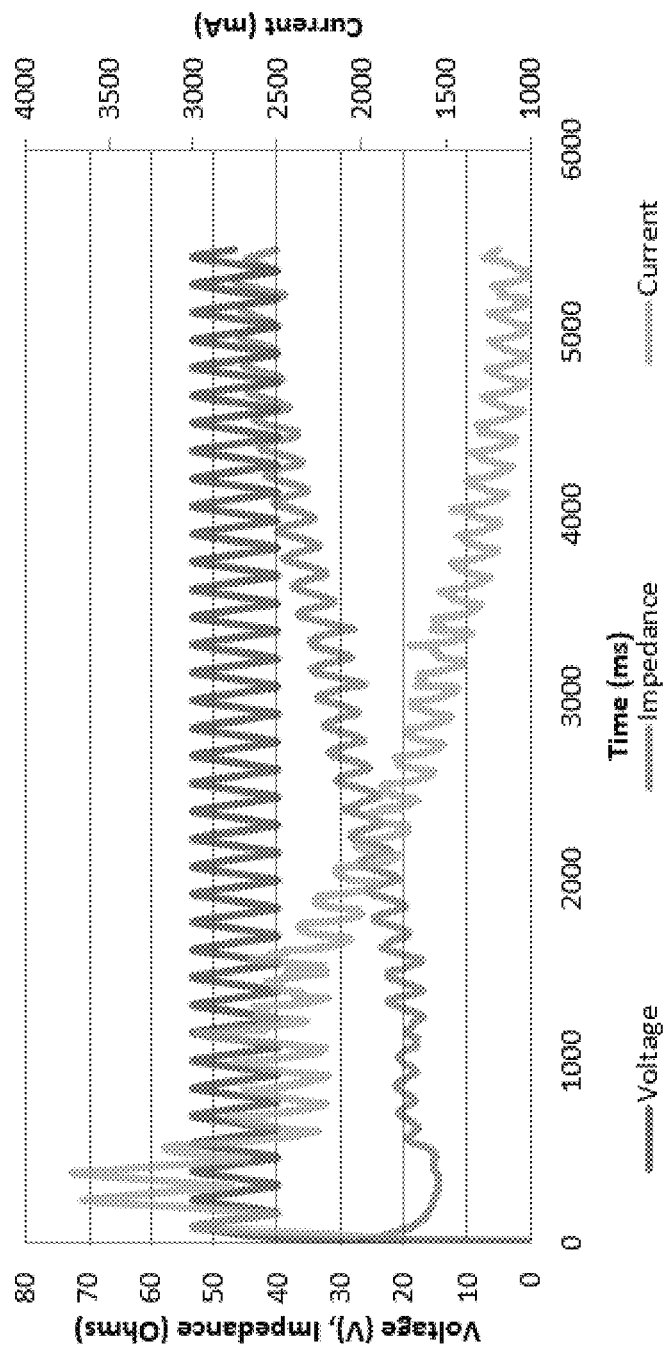

In various embodiments, the electrosurgical system can use the relationship between tissue impedance and voltage to detect when water vaporization occurs. Example relationships between impedance and voltage can be seen in FIG. 17A-FIG. 17C. Once water vaporization begins, the tissue begins emitting steam. The presence of steam in the tissue increases impedance of the tissue. If the heating rate is quickly changed by modifying the voltage applied to the tissue, the water vaporization rate will also change thereby creating either more or less steam. Sharp changes in the amount of steam in the tissue can create a shift in the impedance of the tissue, which is independent of the level of desiccation experienced by the tissue. The two impedance signals, one due to the RF energy being applied to the tissue and the other due to the voltage being applied to the tissue, both result in an overall circuit impedance associated with the tissue.

The sharp changes in impedance due to changing voltage (i.e. the end of the voltage spike) can be used by the electrosurgical system to verify that fluid/water vaporization has begun in the tissue. If the voltage is dropped prior to fluid/water vaporization, the amount of steam in the tissue may already be zero and therefore, cannot decrease (e.g., there is no immediate change in the tissue impedance). However, if fluid/water vaporization began via the use of a high voltage and the voltage is dropped, the amount of steam will decrease thereby resulting in an impedance drop. The relationship between the impedance and voltage can then be used by the electrosurgical system as a verification that fluid/water vaporization has begun in the tissue (corresponding to when the initial voltage spike ends as the measured current begins to drop) which subsequently indicates that the electrosurgical system should drop the voltage. The voltage drop causes the impedance of the tissue to drop thereby slowing down the creation of the steam. However, if the fluid/water vaporization in the tissue has not begun, the tissue must be heated further to reach the water vaporization point.

Figure 17D:
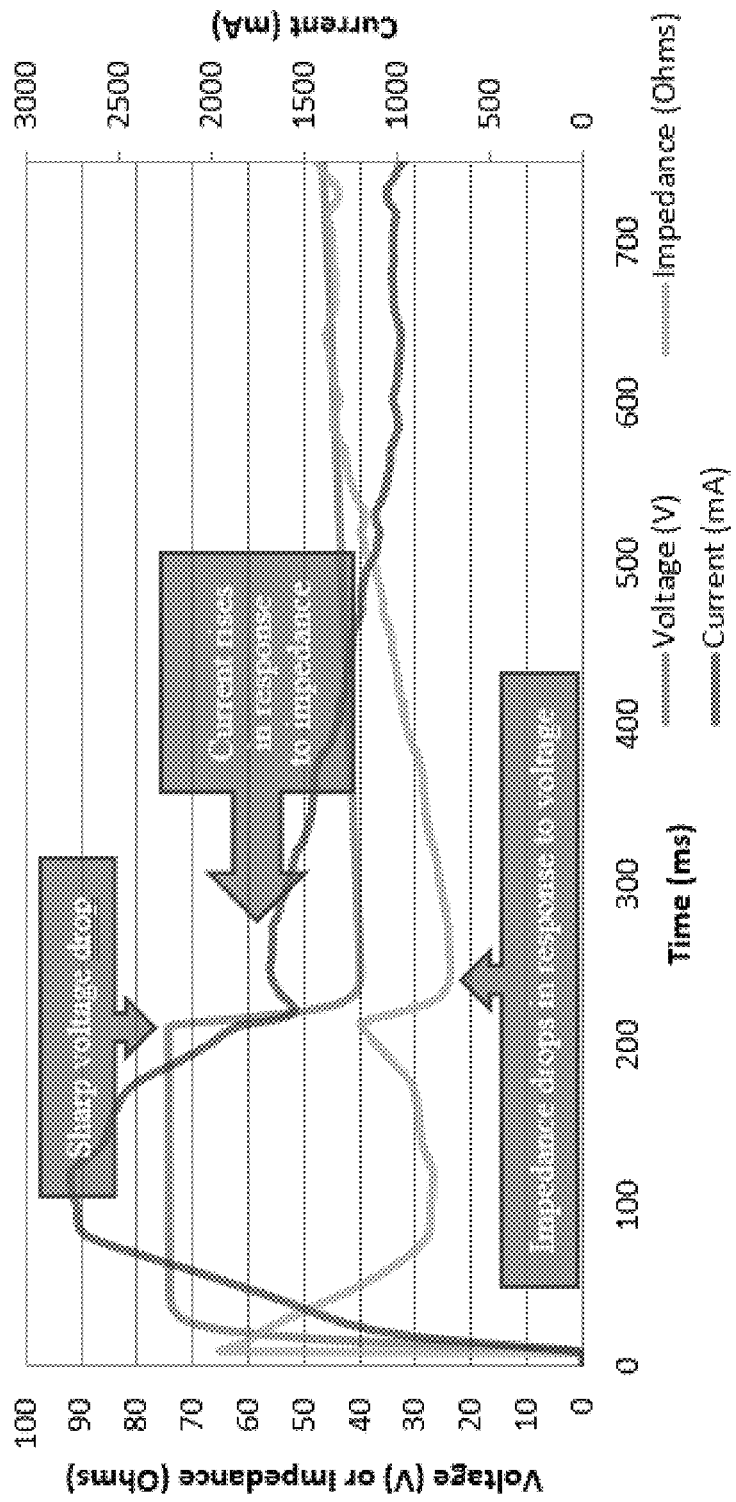

FIG. 17D illustrate a phenomenon whereby current increases or bounces after the voltage is dropped due to impedance drop. In other words, sharply dropping the voltage after fluid/water vaporization has begun can result in more current being transmitted through the tissue in the short term. The current rises because the impedance drops so sharply when the voltage is dropped that the current increases (a phenomenon that creates a current "bounce" in response to a voltage drop). However, shortly after the bounce, the impedance will return to its expected behavior in relation to the voltage. The electrosurgical system can be configured to detect and/or disregard the phenomenon.

As described generally above and described in further detail below, various electrosurgical instruments can be used in the electrosurgical systems described herein. For example, electrosurgical graspers, scissors, tweezers, probes, needles, and other instruments incorporating one, some, or all of the aspects discussed herein can provide various advantages in the electrosurgical system. Various electrosurgical instrument and electrosurgical generator embodiments and combinations thereof are discussed throughout the application. It is contemplated that one, some, or all of the features discussed generally throughout the application can be included in any of the embodiments of the instruments, generators and combinations thereof discussed herein. For example, it can be desirable that each of the electrosurgical instruments described include a memory for interaction with the generator as previously described and vice versa. However, in other embodiments, the instruments and/or generators described can be configured to interact with a standard bipolar radio frequency power source without interaction of an instrument memory. Further, although various embodiments may be described in terms of modules and/or blocks to facilitate description, such modules and/or blocks may be implemented by one or more hardware components (e.g., processors), Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Likewise, such software components may be interchanged with hardware components or a combination thereof and vice versa.

Further examples of the electrosurgical system, instruments, and connections there between and operations and/or functionalities thereof are also described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; Ser. No. 12/416,128, filed Mar. 31, 2009, entitled "Electrosurgical System"; and Ser. No. 14/848,116, filed Sep. 8, 2015, entitled "Electrosurgical System"; the entire disclosures of which are hereby incorporated by reference as if set in full herein. Certain aspects of these electrosurgical generators, instruments, and systems are also discussed herein, and additional details and examples with respect to various embodiments are described in US Provisional Application Nos. 61/994,215, filed May 16, 2014, entitled "Electrosurgical Fusion Device"; 61/944,185, filed May 16, 2014, "Electrosurgical Generator with Synchronous Detector"; 61/994,415, filed May 16, 2014, "Electrosurgical System"; and 61/944,192, filed May 16, 2014, entitled "Electrosurgical Generator", the entire disclosures of which are hereby incorporated by reference as if set in full herein.

The above description is provided to enable any person skilled in the art to make and use the surgical devices and perform the methods described herein and sets forth the best modes contemplated by the inventors of carrying out their inventions. Various modifications, however, will remain apparent to those skilled in the art. It is contemplated that these modifications are within the scope of the present disclosure. Additionally, different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth. Also, embodiments of the present invention should be considered in all respects as illustrative and not restrictive.

The following generally describes the subject matter that the present application covers:

An electrosurgical system for fusing or sealing tissue comprising:
  an electrosurgical instrument configured to:
    grasp tissue being sealed, and
    transmit RF energy to an area of the tissue being grasped to fuse or seal the tissue being grasped; and
  an electrosurgical generator that is connected to the electrosurgical instrument and provides the electrosurgical instrument with RF energy used to seal the tissue, wherein the electrosurgical generator comprises:
    sensors configured to measure current associated with the tissue responsive to the RF energy being transmitted to the tissue being grasped;
    an RF amplifier that generates RF energy, transmits the RF energy to the electrosurgical instrument, and modifies the RF energy based on instructions received from a controller,
    a controller that:
      receives, from the sensors, the measured current,
      identifies a maximum current value from the measured current during a pre-determined period of time, wherein a time associated with the maximum current value corresponds to a beginning of vaporization of fluid in the tissue being grasped,
      generates thresholds based on the maximum current value, wherein the thresholds characterize different conditions or states associated with the fusing or sealing of the tissue being grasped,
      receives subsequent current measurements from the sensors,
      detects that the subsequent current measurements crossed at least one of the thresholds, and
      instructs the RF amplifier to modify the RF energy being generated based on the at least one of the thresholds that was crossed.

Some of the features of the electrosurgical system described above comprise:
  Identifying a maximum current peak corresponding when vaporization of water/fluids in tissue begin.
  Identifying a true maximum current value when two or more current peaks are detected within the pre-determined period of time.
  Identifying tissue thickness based on the maximum current value and modifying the RF energy based on the identified tissue thickness.
  Identifying tissue thickness based on how long it takes until the maximum current value is detected and modifying the RF energy based on the identified tissue thickness.
  Identifying whether the tissue being grasped has been previously sealed (i.e. double/repeat sealed tissue) and modifying the RF energy based on the determination that the tissue has been previously sealed.
  Generating static and/or dynamic thresholds based on the maximum current value to monitor a state of the sealing or fusing of the tissue
  Using the generated static and/or dynamic thresholds to manage the RF energy being applied to the tissue.

The invention claimed is:

1. An electrosurgical system for fusing or sealing tissue, the system comprising:
  an electrosurgical instrument configured to:
    grasp tissue being sealed, and
    transmit RF energy to an area of the tissue being grasped, wherein the transmitted RF energy is configured to fuse or seal the tissue being grasped; and
  an electrosurgical generator that is connected to the electrosurgical instrument, wherein the electrosurgical generator supplies the electrosurgical instrument with the RF energy used to seal the tissue, and wherein the electrosurgical generator comprises:
    a plurality of sensors configured to measure current associated with the tissue being grasped by the electrosurgical instrument, wherein the current being measured is responsive to the RF energy being transmitted to the tissue by the electrosurgical instrument,
    an RF amplifier that is configured to:
      generate an amount of RF energy as instructed by a controller, and
      transmit the RF energy that was generated to the electrosurgical instrument; and the controller that is configured to:
receive, from the plurality of sensors, the measured current for a pre-determined period of time, wherein the pre-determined period of time varies based on a type of the tissue undergoing sealing and is less than a total time required to seal the tissue,
identify a maximum current value and when the maximum current value occurred from the measured current over the pre-determined period of time,
generate a plurality of thresholds based on the maximum current value and when the maximum current value occurred that are used to characterize different conditions associated with the tissue, wherein each different condition dictates how much RF energy is needed to fuse or seal the tissue being grasped, and wherein each of the plurality of thresholds is calculated by the controller using a percentage of or a static offset from the measured maximum current value;
receive subsequent current measurements from the plurality of sensors, and
instruct the RF amplifier to modify the RF energy being generated based on the subsequent current measurements crossing one or more of the plurality of thresholds, the modified RF energy being generated corresponding to the condition of the tissue undergoing fusing or sealing configured to avoid excessive RF energy application to the tissue.

2. The electrosurgical system of claim 1, wherein the plurality of thresholds generated are based on one or more of type, volume, or thickness of the tissue being grasped by the electrosurgical instrument, type of electrosurgical instrument being used, or a surgical procedure being performed.

3. The electrosurgical system of claim 1, wherein modification of the RF energy comprises regulating one or more of a voltage, current, or power of the RF energy being generated by the RF amplifier.

4. The electrosurgical instrument of claim 1, wherein the electrosurgical instrument further comprises an indicator that conveys status information to a user, the indicator comprising one or more of audio, tactile, or visual indicators.

5. The electrosurgical system of claim 1, wherein the controller is configured to further:
identify a tissue thickness based on the identified maximum current value, and
instruct the RF amplifier to initially decrease the RF energy after the identified maximum current value has been detected, the RF energy decrease being smaller for the identified tissue thickness being thin compared to the identified tissue thickness being thick.

6. The electrosurgical system of claim 5, wherein the controller is configured to further instruct the RF amplifier to increase the RF energy from a dropped voltage point at the RF energy decrease to a voltage endpoint, wherein the voltage end point is higher for the identified tissue thickness being thick compared to the identified tissue thickness being thin.

7. The electrosurgical system of claim 5, wherein the RF energy decrease is 30% from the identified maximum current value for thin tissue, and wherein the RF energy decrease is 50% from the identified maximum current value for thick tissue.

8. The electrosurgical system of claim 1, wherein the plurality of sensors are further configured to measure a temperature of the tissue, and wherein the controller is configured to further instruct the RF amplifier to modify the RF energy being generated based on the measured temperature of the tissue.

9. The electrosurgical system of claim 1, wherein the identification of the maximum current value further includes determining whether two or more current peaks occur by monitoring changes in the measured current after detecting a first current peak and calculating a speed in which the measured current changes from the detected first current peak for a pre-determined time window, and the identification of the maximum current value is performed within the pre-determined time window.

10. The electrosurgical system of claim 1, wherein the identification of the maximum current value further comprises comparing with a predetermined max percentage threshold to identify that a user is performing a sealing of the tissue using a tip of the electrosurgical instrument.

11. The electrosurgical system of claim 1, wherein the plurality of sensors are further configured to detect an amount of steam associated with water vaporization, and wherein the controller is further configured to determine a state of desiccation of the tissue based on the detected amount of steam.

12. An electrosurgical system for fusing or sealing tissue, the system comprising:
an electrosurgical instrument configured to:
grasp tissue being sealed, and
transmit RF energy to an area of the tissue being grasped, wherein the transmitted RF energy is configured to fuse or seal the tissue being grasped; and
an electrosurgical generator connected to the electrosurgical instrument configured to supply RF energy to the electrosurgical instrument, comprising:
at least one sensor configured to measure at least one characteristic associated with the tissue being grasped for a pre-determined period of time,
an RF amplifier that is configured to generate an amount of RF energy for the electrosurgical instrument, and
a controller that is configured to:
calculate a plurality of thresholds based on the at least one characteristic measured by the at least one sensor, wherein each of the plurality of thresholds is calculated by the controller using both a percentage from the at least one measured characteristic and a static offset from the at least one measured characteristic,
determine that at least one threshold has been crossed by subsequent measurements from the at least one sensor, and
instruct the RF amplifier to modify the RF energy being generated responsive to the at least one threshold being crossed to avoid tissue complications caused from excessive RF energy application to the tissue,
wherein the RF amplifier initially generates RF energy in a ramping manner for an initial period of time, wherein the ramping manner is based on a type of tissue being fused or sealed, and wherein the at least one sensor monitors the at least one characteristic for a maximum value or peak during the initial period of time corresponding to an RF output peak, wherein an increase in the amount of RF energy corresponding to the ramping manner for a thicker tissue is measured at 2750 mA over a period of 100 milliseconds, and
wherein the increase in the amount of RF energy corresponding to the ramping manner of a thinner tissue is measured at 5500 mA over a period of 50 milliseconds.

13. The electrosurgical system of claim 12, wherein:
the at least one characteristic being measured by the at least one sensor includes measuring a current or a voltage associated with the RF energy being currently generated for the tissue being grasped, and
the controller further calculates a power measurement of the RF energy, or calculates a phase angle or difference between a RF output voltage and a RF output current during supply of the RF energy from the electrosurgical generator to the electrosurgical instrument grasping the tissue.

14. The electrosurgical system of claim 12, wherein the plurality of thresholds corresponds to different states of the tissue undergoing fusing or sealing, wherein the different states correspond to one or more steps in a seal cycle and corresponding conditions for determining when to transition from a current state to a next state.

15. The electrosurgical system of claim 14, wherein one of the different states includes when the tissue has reached a desiccation point.

16. The electrosurgical system of claim 14 wherein one of the different states includes determining that the tissue was previously sealed or is a repeat seal.

17. The electrosurgical system of claim 14, wherein one of the conditions for determining when to transition to the next state comprises a time interval whereby the transition occurs automatically after the time interval has elapsed, and another one of the conditions for determining when to transition to the next state comprises detecting whether an increase in current of the RF energy is detected, the increase in current being detected corresponding to an error state indicating that the tissue had not properly reached desiccation.

18. The electrosurgical system of claim 17, wherein another one of the conditions for determining when to transition to the next state comprises detecting that RF energy being generated for the tissue is at a pre-determined maximum percentage threshold, and wherein the controller subsequently instructs the RF amplifier to terminate generating RF energy.

19. The electrosurgical system of claim 12, wherein the controller implements a delay for a pre-determined period of time between determining whether at least one of the thresholds has been crossed and instructing the RF amplifier to modify the RF energy being generated for the electrosurgical instrument.

20. The electrosurgical system of claim 12, wherein the controller further calculates a change in the parameter obtained from the at least one sensor for different pre-determined periods of time to predict whether one of the plurality of thresholds will be crossed.

21. The electrosurgical system of claim 12, wherein the ramping manner for initially generating the RF energy corresponds to an initial predefined value of 35 V to a maximum value of 45 V over a predefined time period of 500 ms.

22. The electrosurgical system of claim 12, further detecting whether a sufficient amount of tissue has been grasped by the electrosurgical instrument, wherein the detection is performed by:
generating a low voltage measurement signal at the electrosurgical generator for the electrosurgical instrument, the low voltage measurement signal being transmitted to the tissue,
measuring an impedance of the tissue being grasped associated with the transmitted low voltage measurement signal at the electrosurgical instrument, and
determining whether the measured impedance is within an operating range.

* * * * *